US011766287B2

(12) United States Patent
Wiener et al.

(10) Patent No.: US 11,766,287 B2
(45) Date of Patent: *Sep. 26, 2023

(54) METHODS FOR OPERATING GENERATOR FOR DIGITALLY GENERATING ELECTRICAL SIGNAL WAVEFORMS AND SURGICAL INSTRUMENTS

(71) Applicant: Cilag GmbH International, Zug (CH)

(72) Inventors: Eitan T. Wiener, Cincinnati, OH (US); David C. Yates, Morrow, OH (US)

(73) Assignee: Cilag GmbH International, Zug (CH)

( * ) Notice: Subject to any disclaimer, the term of this patent is extended or adjusted under 35 U.S.C. 154(b) by 595 days.

This patent is subject to a terminal disclaimer.

(21) Appl. No.: 16/804,841

(22) Filed: Feb. 28, 2020

(65) Prior Publication Data

US 2020/0268433 A1 Aug. 27, 2020

Related U.S. Application Data

(63) Continuation of application No. 15/265,279, filed on Sep. 14, 2016, now Pat. No. 10,624,691.

(Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1445* (2013.01); *A61B 18/1482* (2013.01);
(Continued)

(58) Field of Classification Search
CPC ............ A61B 18/1206; A61B 18/1445; A61B 18/1482; A61B 2017/00017;
(Continued)

(56) References Cited

U.S. PATENT DOCUMENTS 969,528 A 9/1910 Disbrow
1,570,025 A 1/1926 Young
(Continued)

FOREIGN PATENT DOCUMENTS

CA 2535467 A1 4/1993
CN 2460047 Y 11/2001
(Continued)

OTHER PUBLICATIONS

Amoczky et al., "Thermal Modification of Conective Tissues: Basic Science Considerations and Clinical Implications," J. Am Acad Orthop Surg, vol. 8, No. 5, pp. 305-313 (Sep./Oct. 2000).
(Continued)

*Primary Examiner* — Michael F Peffley
*Assistant Examiner* — Amanda L Zink

(57) ABSTRACT

Disclosed is a method of generating electrical signal waveforms by a generator. The generator includes a processor and a memory in communication with the processor. The memory defines a first and second table. The processor retrieves information from the first table defined in the memory, where the information is associated with a first wave shape of a first electrical signal waveform for performing a surgical procedure. The processor retrieves information from the second table defined in the memory, where the information is associated with a second wave shape of a second electrical signal waveform for performing a surgical procedure. The processor combines the first and second wave shapes to create a combined wave shape of an electrical signal waveform for performing a surgical procedure and the combined wave shape electrical signal waveform for performing a surgical procedure is delivered to a surgical instrument.

19 Claims, 29 Drawing Sheets

Related U.S. Application Data

(60) Provisional application No. 62/235,368, filed on Sep. 30, 2015, provisional application No. 62/235,260, filed on Sep. 30, 2015, provisional application No. 62/235,466, filed on Sep. 30, 2015.

(51) Int. Cl.
| | | |
|---|---|---|
| *G06F 1/02* | (2006.01) | |
| *H03K 5/01* | (2006.01) | |
| *A61B 18/00* | (2006.01) | |
| *A61B 17/32* | (2006.01) | |
| *A61B 17/00* | (2006.01) | |
| *B06B 1/02* | (2006.01) | |

(52) U.S. Cl.
CPC ............. *G06F 1/022* (2013.01); *H03K 5/01* (2013.01); *A61B 2017/0015* (2013.01); *A61B 2017/00017* (2013.01); *A61B 2017/00137* (2013.01); *A61B 2017/320094* (2017.08); *A61B 2018/00642* (2013.01); *A61B 2018/00994* (2013.01); *A61B 2018/128* (2013.01); *A61B 2018/1273* (2013.01); *A61B 2018/1293* (2013.01); *B06B 1/0207* (2013.01)

(58) Field of Classification Search
CPC .. A61B 2017/00137; A61B 2017/0015; A61B 2017/320094; A61B 2018/00642; A61B 2018/00994; A61B 2018/1273; A61B 2018/128; A61B 2018/1293
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A | 4/1988 | Rexroth et al. |
| 4,761,871 A | 8/1988 | O'Connor et al. |
| 4,808,154 A | 2/1989 | Freeman |
| 4,819,635 A | 4/1989 | Shapiro |

(56) References Cited

U.S. PATENT DOCUMENTS

| | | |
|---|---|---|
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |

(56) References Cited

U.S. PATENT DOCUMENTS

| | | |
|---|---|---|
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tai et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |

(56) References Cited

U.S. PATENT DOCUMENTS

| | | |
|---|---|---|
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |

(56) References Cited

U.S. PATENT DOCUMENTS

| | | |
|---|---|---|
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |

(56) References Cited

U.S. PATENT DOCUMENTS

| | | |
|---|---|---|
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,988,649 B2 | 1/2006 | Shelton, IV et al. |
| 6,994,708 B2 | 2/2006 | Manzo |

(56) References Cited

U.S. PATENT DOCUMENTS

| | | |
|---|---|---|
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |

(56) References Cited

U.S. PATENT DOCUMENTS

| | | |
|---|---|---|
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |

(56) References Cited

U.S. PATENT DOCUMENTS

| | | | |
|---|---|---|---|
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,954,682 B2 | 6/2011 | Giordano et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,048,074 B2 | 11/2011 | Masuda |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Esky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |

(56) References Cited

U.S. PATENT DOCUMENTS

| | | |
|---|---|---|
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |

(56) References Cited

U.S. PATENT DOCUMENTS

| | | |
|---|---|---|
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,517,239 B2 | 8/2013 | Scheib et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,702 B1 | 4/2014 | Edwards et al. |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |

(56) References Cited

U.S. PATENT DOCUMENTS

| | | |
|---|---|---|
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,692 B2 | 5/2015 | Behnke, II et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |

(56) References Cited

U.S. PATENT DOCUMENTS

| | | |
|---|---|---|
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,333 B2 | 8/2015 | Konesky et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,266,310 B2 | 2/2016 | Krogdahl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch, Jr. et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |

(56) References Cited

U.S. PATENT DOCUMENTS

| | | |
|---|---|---|
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horiie et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,877,782 B2 | 1/2018 | Voegele et al. |
| 9,878,184 B2 | 1/2018 | Beaupre |
| 9,883,860 B2 | 2/2018 | Leimbach et al. |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,895,160 B2 | 2/2018 | Fan et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |

(56) References Cited

U.S. PATENT DOCUMENTS

| | | |
|---|---|---|
| 9,993,248 B2 | 6/2018 | Shelton, IV et al. |
| 9,993,258 B2 | 6/2018 | Shelton, IV et al. |
| 9,993,289 B2 | 6/2018 | Sobajima et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,347 B2 | 10/2018 | Weisshaupt et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter, III et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |

(56) References Cited

U.S. PATENT DOCUMENTS

| | | |
|---|---|---|
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |

(56) References Cited

U.S. PATENT DOCUMENTS

| | | |
|---|---|---|
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,275 B2 | 6/2021 | Boudreaux et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,406,382 B2 | 8/2022 | Shelton, IV et al. |
| 11,419,606 B2 | 8/2022 | Overmyer et al. |
| 11,424,027 B2 | 8/2022 | Shelton, IV |
| 11,426,167 B2 | 8/2022 | Shelton, IV et al. |
| 11,446,029 B2 | 9/2022 | Shelton, IV et al. |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,478,242 B2 | 10/2022 | Shelton, IV et al. |
| 11,484,310 B2 | 11/2022 | Shelton, IV et al. |
| 11,504,122 B2 | 11/2022 | Shelton, IV et al. |
| 11,517,309 B2 | 12/2022 | Bakos et al. |
| 11,529,137 B2 | 12/2022 | Shelton, IV et al. |
| 11,529,139 B2 | 12/2022 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |

(56) References Cited

U.S. PATENT DOCUMENTS

| | | |
|---|---|---|
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0133152 A1 | 9/2002 | Strul |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0176778 A1 | 9/2003 | Messing et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0143263 A1 | 7/2004 | Schechter et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0171533 A1 | 8/2005 | Latterell et al. |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0142656 A1 | 6/2006 | Malackowski et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1 | 9/2006 | Garito et al. |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1* | 3/2007 | Podhajsky ......... A61B 18/1402 606/34 |
| 2007/0067123 A1 | 3/2007 | Jungerman |
| 2007/0073185 A1 | 3/2007 | Nakao |

(56) References Cited

U.S. PATENT DOCUMENTS

| | | |
|---|---|---|
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1* | 12/2007 | Johnson ............... G06F 1/0321 708/270 |
| 2008/0005213 A1 | 1/2008 | Holtzman |
| 2008/0013809 A1 | 1/2008 | Zhu et al. |
| 2008/0015473 A1 | 1/2008 | Shimizu |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0167670 A1 | 7/2008 | Shelton et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0062786 A1* | 3/2009 | Garito ................... A61B 18/12 606/37 |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088745 A1 | 4/2009 | Hushka et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131934 A1 | 5/2009 | Odom et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0036373 A1 | 2/2010 | Ward |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |

(56) References Cited

U.S. PATENT DOCUMENTS

| | | |
|---|---|---|
| 2010/0187283 A1 | 7/2010 | Crainich et al. |
| 2010/0193566 A1 | 8/2010 | Scheib et al. |
| 2010/0204721 A1 | 8/2010 | Young et al. |
| 2010/0217258 A1* | 8/2010 | Floume ............... A61B 18/1445 606/41 |
| 2010/0222714 A1 | 9/2010 | Muir et al. |
| 2010/0222752 A1 | 9/2010 | Collins, Jr. et al. |
| 2010/0225209 A1 | 9/2010 | Goldberg et al. |
| 2010/0228249 A1 | 9/2010 | Mohr et al. |
| 2010/0228250 A1 | 9/2010 | Brogna |
| 2010/0234906 A1 | 9/2010 | Koh |
| 2010/0256635 A1 | 10/2010 | McKenna et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0305564 A1 | 12/2010 | Livneh |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101493 A1 | 4/2012 | Masuda et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143182 A1 | 6/2012 | Ullrich et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |
| 2012/0234893 A1 | 9/2012 | Schuckmann et al. |
| 2012/0253328 A1 | 10/2012 | Cunningham et al. |
| 2012/0253329 A1 | 10/2012 | Zemlok et al. |
| 2012/0265196 A1* | 10/2012 | Turner ............... A61B 18/1206 606/34 |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0103031 A1 | 4/2013 | Garrison |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0267874 A1 | 10/2013 | Marcotte et al. |
| 2013/0267943 A1* | 10/2013 | Hancock ............... H05B 6/806 606/33 |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0236152 A1 | 8/2014 | Walberg et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0303612 A1 | 10/2014 | Williams |
| 2014/0357984 A1 | 12/2014 | Wallace et al. |
| 2014/0373003 A1 | 12/2014 | Grez et al. |
| 2015/0014392 A1 | 1/2015 | Williams et al. |
| 2015/0025528 A1 | 1/2015 | Arts |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1 | 4/2015 | Steege |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0230796 A1 | 8/2015 | Calderoni |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |

(56) References Cited

U.S. PATENT DOCUMENTS

| | | |
|---|---|---|
| 2015/0272581 A1 | 10/2015 | Leimbach et al. |
| 2015/0272582 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2015/0374457 A1 | 12/2015 | Colby |
| 2016/0000437 A1 | 1/2016 | Giordano et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051314 A1 | 2/2016 | Batchelor et al. |
| 2016/0051316 A1 | 2/2016 | Boudreaux |
| 2016/0066909 A1 | 3/2016 | Swayze et al. |
| 2016/0066913 A1 | 3/2016 | Swayze et al. |
| 2016/0120601 A1 | 5/2016 | Boudreaux et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0331455 A1 | 11/2016 | Hancock et al. |
| 2016/0358849 A1 | 12/2016 | Jur et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0224332 A1 | 8/2017 | Hunter et al. |
| 2017/0224405 A1 | 8/2017 | Takashino et al. |
| 2017/0231628 A1 | 8/2017 | Shelton, IV et al. |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2017/0367772 A1 | 12/2017 | Gunn et al. |
| 2018/0014872 A1 | 1/2018 | Dickerson |
| 2018/0098785 A1 | 4/2018 | Price et al. |
| 2018/0132850 A1 | 5/2018 | Leimbach et al. |
| 2018/0146976 A1 | 5/2018 | Clauda et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1 | 7/2018 | Felder et al. |
| 2018/0221045 A1 | 8/2018 | Zimmerman et al. |
| 2018/0235691 A1 | 8/2018 | Voegele et al. |
| 2018/0250066 A1 | 9/2018 | Ding et al. |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0333179 A1 | 11/2018 | Weisenburgh, II et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000475 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0053818 A1 | 2/2019 | Nelson et al. |
| 2019/0104919 A1 | 4/2019 | Shelton, IV et al. |
| 2019/0105067 A1 | 4/2019 | Boudreaux et al. |
| 2019/0117293 A1 | 4/2019 | Kano et al. |
| 2019/0125384 A1 | 5/2019 | Scheib et al. |
| 2019/0125390 A1 | 5/2019 | Shelton, IV et al. |
| 2019/0175258 A1 | 6/2019 | Tsuruta |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0262030 A1 | 8/2019 | Faller et al. |
| 2019/0269455 A1 | 9/2019 | Mensch et al. |
| 2019/0274700 A1 | 9/2019 | Robertson et al. |
| 2019/0282288 A1 | 9/2019 | Boudreaux |
| 2019/0290265 A1 | 9/2019 | Shelton, IV et al. |
| 2019/0298350 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0030021 A1 | 1/2020 | Yates et al. |
| 2020/0054321 A1 | 2/2020 | Harris et al. |
| 2020/0054382 A1 | 2/2020 | Yates et al. |
| 2020/0078076 A1 | 3/2020 | Henderson et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0100825 A1 | 4/2020 | Henderson et al. |
| 2020/0100830 A1 | 4/2020 | Henderson et al. |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261086 A1 | 8/2020 | Zeiner et al. |
| 2020/0261141 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0338370 A1 | 10/2020 | Wiener et al. |
| 2020/0405296 A1 | 12/2020 | Shelton, IV et al. |
| 2020/0405302 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405439 A1 | 12/2020 | Shelton, IV et al. |

(56) References Cited

U.S. PATENT DOCUMENTS

| | | |
|---|---|---|
| 2020/0410177 A1 | 12/2020 | Shelton, IV |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0153927 A1 | 5/2021 | Ross et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196333 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |
| 2022/0304736 A1 | 9/2022 | Boudreaux |
| 2022/0313297 A1 | 10/2022 | Aldridge et al. |
| 2022/0346863 A1 | 11/2022 | Yates et al. |
| 2022/0387067 A1 | 12/2022 | Faller et al. |
| 2023/0038162 A1 | 2/2023 | Timm et al. |
| 2023/0048996 A1 | 2/2023 | Vakharia et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0576482 A | 3/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |

(56) References Cited

FOREIGN PATENT DOCUMENTS

| | | |
|---|---|---|
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| JP | 2013126430 A | 6/2013 |
| KR | 100789356 B1 | 12/2007 |
| KR | 101298237 B1 | 8/2013 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-02080793 A1 | 10/2002 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Hörmann et al., "Reversible and irreversible denaturation of collagen fibers." Biochemistry, 10, pp. 932-937 (1971).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191.asp (15 pages).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

Covidien Brochure, The LigaSure Precise™ Instrument, dated Mar. 2011 (2 pages).

AST Products, Inc., "Principles of Video Contact Angle Analysis," 20 pages, (2006).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C," Journal of Biomechanics, 31, pp. 211-216 (1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Moraleda et al., A Temperature Sensor Based on a Polymer Optical Fiber Macro-Bend, Sensors 2013, 13, 13076-13089, doi: 10.3390/S131013076, ISSN 1424-8220.

Leonard I. Malis, M.D., "The Value of Irrigation During Bipolar Coagulation," 1989.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Incropera et al., Fundamentals of Heat and Mass Transfer, Wiley, New York (1990). (Book--not attached).

(56) References Cited

OTHER PUBLICATIONS

F. A. Duck, "Optical Properties of Tissue Including Ultraviolet and Infrared Radiation," pp. 43-71 in Physical Properties of Tissue (1990).
Campbell et al., "Thermal Imaging in Surgery," p. 19-3, in Medical Infrared Imaging, N. A. Diakides and J. D. Bronzino, Eds. (2008).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and No. in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Kurt Gieck & Reiner Gieck, *Engineering Formulas* § Z.7 (7th ed. 1997).
Glaser and Subak-Sharpe,Integrated Circuit Engineering, Addison-Wesley Publishing, Reading, MA (1979). (book--not attached).
Covidien 501 (k) Summary Sonicision, dated Feb. 24, 2011 (7 pages).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).

\* cited by examiner

METHODS FOR OPERATING GENERATOR FOR DIGITALLY GENERATING ELECTRICAL SIGNAL WAVEFORMS AND SURGICAL INSTRUMENTS

CROSS-REFERENCE TO RELATED APPLICATIONS

This application is a continuation application claiming priority under 35 U.S.C. § 120 to U.S. patent application Ser. No. 15/265,279, titled TECHNIQUES FOR OPERATING GENERATOR FOR DIGITALLY GENERATING ELECTRICAL SIGNAL WAVEFORMS AND SURGICAL INSTRUMENTS, filed Sep. 14, 2016, now U.S. Pat. No. 10,624,691, which claims the benefit under 35 U.S.C. § 119(e) of U.S. Provisional Patent Application Ser. No. 62/235,260, titled GENERATOR FOR PROVIDING COMBINED RADIO FREQUENCY AND ULTRASONIC ENERGIES, filed Sep. 30, 2015, U.S. Provisional Patent Application Ser. No. 62/235,368, titled CIRCUIT TOPOLOGIES FOR GENERATOR, filed Sep. 30, 2015, and U.S. Provisional Patent Application Ser. No. 62/235,466, titled SURGICAL INSTRUMENT WITH USER ADAPTABLE ALGORITHMS, filed Sep. 30, 2015, the contents of each of which are incorporated herein by reference in their entirety.

TECHNICAL FIELD

The present disclosure generally relates to ultrasonic surgical systems, electrosurgical systems, and combination electrosurgical/ultrasonic systems for performing surgical procedures such as coagulating, sealing, and/or cutting tissue. In particular, the present disclosure relates to customized algorithms for performing such procedures based on the type of tissue being treated. More particularly, the present disclosure relates to a generator which digitally generates electrical signal waveforms for surgical instruments used to perform such procedures. The digital electrical signal waveforms are stored in a lookup table. The generator digitally generates multiple electrical signal waveforms to drive multiple ultrasonic transducers.

BACKGROUND

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical devices for applying electrical energy to tissue in order to treat and/or destroy the tissue are also finding increasingly widespread applications in surgical procedures. An electrosurgical device typically includes a handpiece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device also may include a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency (RF) energy that may be in a frequency range described in EN 60601-2-2:2009+A11: 2011, Definition 201.3.218—HIGH FREQUENCY. For example, the frequencies in monopolar RF applications are typically restricted to less than 5 MHz. However, in bipolar RF applications, the frequency can be almost anything. Frequencies above 200 kHz can be typically used for MONOPOLAR applications in order to avoid the unwanted stimulation of nerves and muscles which would result from the use of low frequency current. Lower frequencies may be used for BIPOLAR techniques if the RISK ANALYSIS shows the possibility of neuromuscular stimulation has been mitigated to an acceptable level. Normally, frequencies above 5 MHz are not used in order to minimize the problems associated with HIGH FREQUENCY LEAKAGE CURRENTS. However, higher frequencies may be used in the case of BIPOLAR techniques. It is generally recognized that 10 mA is the lower threshold of thermal effects on tissue.

In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

Other electrical surgical instruments include, without limitation, irreversible and/or reversible electroporation, and/or microwave technologies, among others. Accordingly, the techniques disclosed herein are applicable to ultrasonic, bipolar or monopolar RF (electrosurgical), irreversible and/ or reversible electroporation, and/or microwave based surgical instruments, among others.

A challenge of using these medical devices is the inability to control and customize the power output depending on the type of tissue being treated by the devices. It would be desirable to provide a surgical instrument that overcomes some of the deficiencies of current instruments. The surgical system described herein overcomes those deficiencies.

As disclosed herein, a generator may be configured to generate an output waveform digitally and provide it to a surgical instrument such that the surgical instrument may utilize the waveform for various tissue effects. The present disclosure provides for generator capabilities that promote tissue effects via wave-shaping and that drive RF and Ultrasonic energy simultaneously to a single surgical instrument or multiple surgical instruments.

Conventional generators for ultrasonic surgical instruments are configured to drive a single ultrasonic transducer. Shortcomings of such conventional ultrasonic generators is the inability to drive multiple ultrasonic transducers in one or more instruments simultaneously. Other shortcomings include the inability of ultrasonic generators to drive multiple vibration modes in one instrument to achieve longer active length at the tip of an ultrasonic blade to provide various tissue effects.

SUMMARY

As disclosed herein, a generator may be configured to generate an output waveform digitally and provide it to a surgical instrument such that the surgical instrument may utilize the waveform for various tissue effects. The present disclosure provides for generator capabilities that promote tissue effects via wave-shaping and that drive RF and Ultrasonic energy simultaneously to a single surgical instrument or multiple surgical instruments. The present disclosure also provides a generator configured to generate wave-shaping to protect electrical output components of the generator when driving simultaneous RF and Ultrasonic waveforms.

In one aspect, a method of generating electrical signal waveforms by a generator is provided. The generator comprises a digital processing circuit, a memory circuit in communication with the digital processing circuit, a digital synthesis circuit in communication with the digital processing circuit and the memory circuit, and a digital-to-analog converter (DAC) circuit. The memory circuit defines a lookup table. The method comprises storing, by the digital processing circuit, phase points of a digital electrical signal waveform in the lookup table defined by the memory circuit, wherein the digital electrical signal waveform is represented by a predetermined number of phase points, wherein the predetermined number phase points define a predetermined wave shape; receiving a clock signal by the digital synthesis circuit, and at each clock cycle: retrieving, by the digital processing circuit, a phase point from the lookup table; and converting, by the DAC circuit, the retrieved phase point to an analog signal.

In another aspect, a method of generating electrical signal waveforms by a generator is provided. The generator comprises a digital processing circuit, a memory circuit in communication with the digital processing circuit, a digital synthesis circuit in communication with the digital processing circuit and the memory circuit, and a digital-to-analog converter (DAC) circuit, where the memory circuit defines first and second lookup tables. The method comprises storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; receiving, by the digital synthesis circuit, a clock signal, and at each clock cycle: retrieving, by the digital synthesis circuit, a phase point from the first lookup table; retrieving, by the digital synthesis circuit, a phase point from the second lookup table; and determining, by the digital processing circuit, whether to switch between the phase points of the first and second electrical signal waveforms or to synchronize the phase points of the first and second electrical signal waveforms.

In yet another a generator for generating electrical signal waveforms is provided. The generator comprises a digital processing circuit; a memory circuit in communication with the digital processing circuit, the memory circuit defining a lookup table; a digital synthesis circuit in communication with the digital processing circuit and the memory circuit, the digital synthesis circuit receiving a clock signal; and a digital-to-analog converter (DAC) circuit. The digital processing circuit configured to store phase points of a digital electrical signal waveform in the lookup table defined by the memory circuit, wherein the digital electrical signal waveform is represented by a predetermined number of phase points, wherein the predetermined number phase points define a predetermined wave shape; and retrieve a phase point from the lookup table at each clock cycle; and the DAC circuit configured to convert the retrieved phase point to an analog signal.

In one aspect, a method of generating electrical signal waveforms by a generator is provided. The generator comprises a digital processing circuit, a memory circuit in communication with the digital processing circuit, the memory circuit defining first and second lookup tables, a digital synthesis circuit in communication with the digital processing circuit and the memory circuit, and a digital-to-analog converter (DAC). The method comprises storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; and receiving a clock signal by the digital synthesis circuit, and at each clock cycle retrieving, by the digital synthesis circuit, a phase point from the first lookup table; retrieving, by the digital synthesis circuit, a phase point from the second lookup table; combining, by the digital processing circuit, the phase point from the first lookup table with the phase point from the second lookup table to generate a combined phase point; and converting, by the DAC circuit, the combined phase point into an analog signal; wherein the analog signal is configured to drive a first and second ultrasonic transducer.

In another aspect, a method of generating electrical signal waveforms by a generator is provided. The generator comprises a digital processing circuit, a memory circuit in communication with the digital processing circuit, the memory circuit defining first and second lookup tables, a digital synthesis circuit in communication with the digital processing circuit and the memory circuit, and a digital-to-analog converter (DAC) circuit. The method comprises storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; and receiving a clock signal by the digital synthesis circuit, and at each clock cycle retrieving, by the digital synthesis circuit, a phase point from the first lookup table; retrieving, by the digital synthesis circuit, a phase point from the second lookup table; combining, by the digital processing circuit, the phase point from the first lookup table with the phase point from the second lookup table to generate a combined phase point; and converting, by the DAC circuit, the combined phase point into an analog signal; wherein the analog signal is configured to drive a plurality of ultrasonic operational modes of an ultrasonic device.

In yet another a generator for generating electrical signal waveforms is provided. The generator comprises a digital processing circuit; a memory circuit in communication with the digital processing circuit, the memory circuit defining a lookup table; a digital synthesis circuit in communication with the digital processing circuit and the memory circuit, the digital synthesis circuit receiving a clock signal; and a digital-to-analog converter (DAC) circuit; the digital processing circuit configured to: store phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; and store phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; at each clock cycle the digital synthesis circuit is configured to: retrieve a phase point from the first lookup table; retrieve a phase point from the second lookup table; the digital processing circuit configured to: combine the phase point from the first lookup table with the phase point from the second lookup table to generate a combined phase point; and the DAC circuit is configured to convert the combined phase point into an analog signal; wherein the analog signal is configured to drive a first and second ultrasonic transducer.

In one aspect, a method of generating electrical signal waveforms by a generator is provided. The generator comprises a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; receiving, by the digital synthesis circuit, a clock signal, and at each clock cycle; retrieving, by the digital synthesis circuit, a phase point from the first lookup table; retrieving, by the digital synthesis circuit, a phase point from the second lookup table; combining, by the digital processing circuit, the first and second digital electrical signal waveforms to form a combined digital electrical signal waveform; and modifying, by the digital processing circuit, the combined digital electrical signal waveform to form a modified digital electrical signal waveform, wherein a peak amplitude of the modified digital electrical signal waveform does not exceed a predetermined amplitude value.

In another aspect, a method of generating electrical signal waveforms by a generator is provided. The generator comprises a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape, wherein the second digital electrical signal waveform is a function of the first digital electrical signal waveform; receiving, by the digital synthesis circuit, a clock signal, and at each clock cycle; retrieving, by the digital synthesis circuit, a phase point from the first lookup table; retrieving, by the digital synthesis circuit, a phase point from the second lookup table; combining, by the digital processing circuit, the first and second digital electrical signal waveforms to form a combined digital electrical signal waveform; and modifying, by the digital processing circuit, the combined digital electrical signal waveform to form a modified digital electrical signal waveform, wherein a peak amplitude of the modified digital electrical signal waveform does not exceed a predetermined amplitude value.

In yet another a generator for generating electrical signal waveforms is provided. The generator comprises a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape, wherein the second digital electrical signal waveform is a function of the first digital electrical signal waveform; receiving, by the digital synthesis circuit, a clock signal, and at each clock cycle; retrieving, by the digital synthesis circuit, a phase point from the first lookup table; retrieving, by the digital synthesis circuit, a phase point from the second lookup table; modifying, by the digital processing circuit, a frequency of the first digital electrical signal waveform to form a frequency modified first digital electrical signal waveform; and combining, by the digital processing circuit, the frequency modified first digital electrical signal waveform and the second digital electrical signal waveform to form a combined digital electrical signal waveform.

FIGURES

The novel features of the described forms are set forth with particularity in the appended claims. The described forms, however, both as to organization and methods of operation, may be best understood by reference to the following description, taken in conjunction with the accompanying drawings in which:

Figure 33:
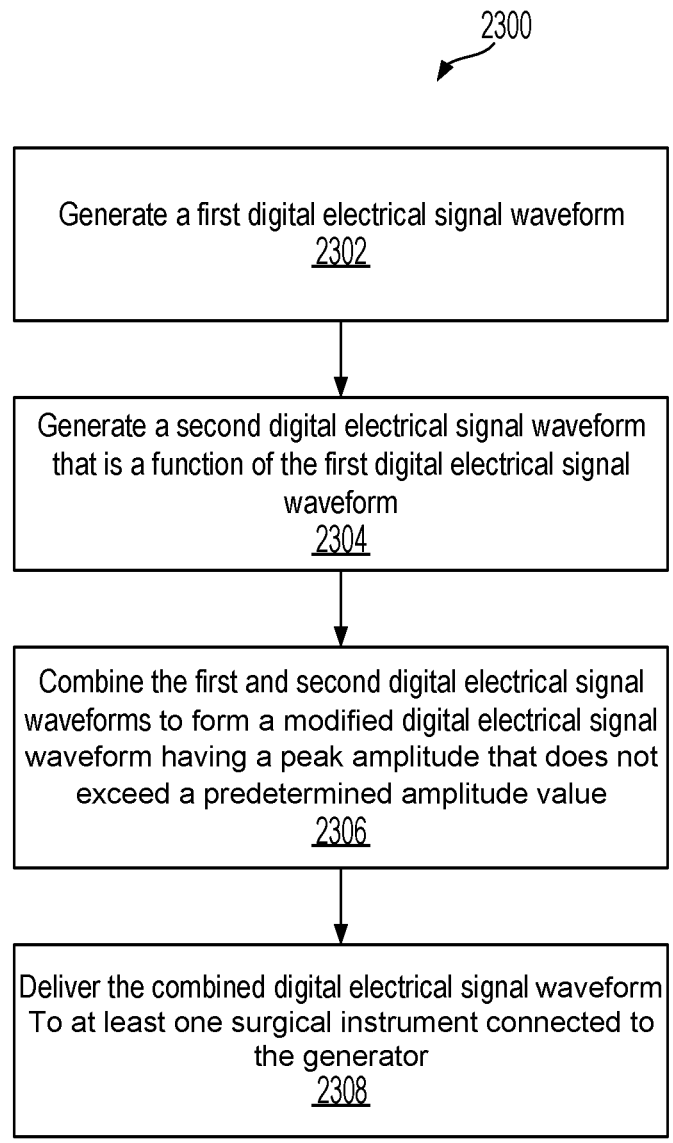
Figure 34:
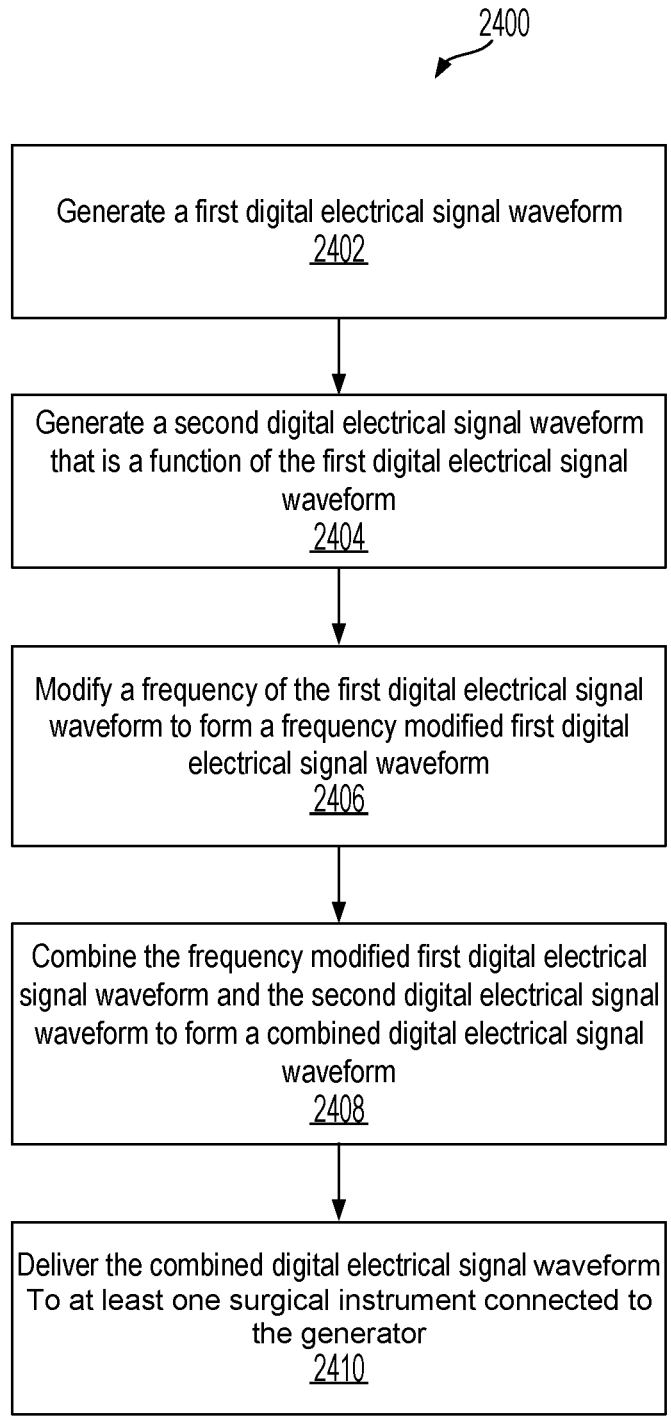

FIG. 33 is a logic flow diagram of a method of generating a electrical signal waveform configured to drive a surgical instrument and to protect output components of a generator according to another aspect; and FIG. 34 is a logic flow diagram of a method of generating a digital electrical signal waveform configured to drive a surgical instrument and to protect output components of a generator according to another aspect.

DESCRIPTION

Before explaining various forms of surgical instruments in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions employed herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Various forms are directed to improved ultrasonic and/or RF electrosurgical instruments configured for effecting tissue dissecting, cutting, and/or coagulation during surgical procedures. In one form, an ultrasonic and/or RF electrosurgical instruments may be configured for use in open surgical procedures, but has applications in other types of surgery, such as laparoscopic, endoscopic, and robotic-assisted procedures. Versatile use is facilitated by selective use of ultrasonic energy.

This application is related to the following commonly owned patent application filed Sep. 14, 2016:
U.S. patent application Ser. No. 15/265,293, titled TECHNIQUES FOR CIRCUIT TOPOLOGIES FOR COMBINED GENERATOR, by Wiener et al., now U.S. Patent Application Publication No. 2017/0086910.

This application also is related to the following commonly owned patent applications filed on Sep. 7, 2016:
U.S. patent application Ser. No. 15/258,570, titled CIRCUIT TOPOLOGIES FOR COMBINED GENERATOR, by Wiener et al., now U.S. Patent Application Publication No. 2017/0086908;
U.S. patent application Ser. No. 15/258,578, titled CIRCUITS FOR SUPPLYING ISOLATED DIRECT CURRENT (DC) VOLTAGE TO SURGICAL INSTRUMENTS, by Wiener et al., now U.S. Patent Application Publication No. 2017/0086911;
U.S. patent application Ser. No. 15/258,586, titled FREQUENCY AGILE GENERATOR FOR A SURGICAL INSTRUMENT, by Yates et al., now U.S. Patent Application Publication No. 2017/0086909;
U.S. patent application Ser. No. 15/258,598, titled METHOD AND APPARATUS FOR SELECTING OPERATIONS OF A SURGICAL INSTRUMENT BASED ON USER INTENTION, by Asher et al., now U.S. Patent Application Publication No. 2017/0086876;
U.S. patent application Ser. No. 15/258,569, titled GENERATOR FOR DIGITALLY GENERATING ELECTRICAL SIGNAL WAVEFORMS FOR ELECTROSURGICAL AND ULTRASONIC SURGICAL INSTRUMENTS, by Wiener et al., now U.S. Pat. No. 10,194,973;
U.S. patent application Ser. No. 15/258,611, titled GENERATOR FOR DIGITALLY GENERATING COMBINED ELECTRICAL SIGNAL WAVEFORMS FOR ULTRASONIC SURGICAL INSTRUMENTS, by Wiener et al., now U.S. Patent Application Publication No. 2017/0086912;
U.S. patent application Ser. No. 15/258,650, titled PROTECTION TECHNIQUES FOR GENERATOR FOR DIGITALLY GENERATING ELECTROSURGICAL AND ULTRASONIC DIGITAL ELECTRICAL SIGNAL WAVEFORMS, by Yates et al., now U.S. Patent Application Publication No. 2017/0086913;
each of which is incorporated herein by reference in its entirety.

This application also is related to the following commonly owned patent applications filed on Jun. 9, 2016:
U.S. patent application Ser. No. 15/177,430, titled SURGICAL INSTRUMENT WITH USER ADAPTABLE TECHNIQUES, now U.S. Patent Application Publication No. 2017/0000541;
U.S. patent application Ser. No. 15/177,439, titled SURGICAL INSTRUMENT WITH USER ADAPTABLE TECHNIQUES BASED ON TISSUE TYPE, now U.S. Patent Application Publication No. 2017/0000516;
U.S. patent application Ser. No. 15/177,449, titled SURGICAL SYSTEM WITH USER ADAPTABLE TECHNIQUES EMPLOYING MULTIPLE ENERGY MODALITIES BASED ON TISSUE, now U.S. Patent Application Publication No. 2017/0000553;
U.S. patent application Ser. No. 15/177,456, titled SURGICAL SYSTEM WITH USER ADAPTABLE TECHNIQUES BASED ON TISSUE IMPEDANCE, now U.S. Patent Application Publication No. 2017/0000542;
U.S. patent application Ser. No. 15/177,466, titled SURGICAL SYSTEM WITH USER ADAPTABLE TECHNIQUES EMPLOYING SIMULTANEOUS ENERGY MODALITIES BASED ON TISSUE PARAMETERS, now U.S. Patent Application Publication No. 2017/0000554;
each of which is incorporated herein by reference in its entirety.

The various forms will be described in combination with an ultrasonic instrument as described herein. Such description is provided by way of example, and not limitation, and is not intended to limit the scope and applications thereof. For example, any one of the described forms is useful in combination with a multitude of ultrasonic instruments including those described in, for example, U.S. Pat. Nos. 5,938,633; 5,935,144; 5,944,737; 5,322,055; 5,630,420; and 5,449,370, which are each incorporated by reference herein in their entirety.

As will become apparent from the following description, it is contemplated that forms of the surgical instruments described herein may be used in association with an oscillator unit of a surgical system, whereby ultrasonic energy from the oscillator unit provides the desired ultrasonic actuation for the present surgical instrument. It is also contemplated that forms of the surgical instrument described herein may be used in association with a signal generator unit of a surgical system, whereby RF electrical energy, for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One form of the present surgical apparatus is particularly configured for disposable use by virtue of its straightforward construction. However, it is also contemplated that other forms of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various forms of the presently described surgical instruments may be configured for single use and/or multiple use with either detachable and/or non-detachable integral oscillator and/or signal generator unit, without limitation, and all combinations of such configurations are contemplated to be within the scope of the present disclosure.

In one aspect, the desired wave shape may be digitized by 1024 phase points, which are stored in a table, such as, for example, a direct digital synthesis table with a field programmable gate array (FPGA) of the generator. The generator software and digital controls command the FPGA to scan the addresses in this table at the frequency of interest which in turn provides varying digital input values to a DAC circuit that feeds to power amplifier. This method enables generating practically any (or many) types of wave shapes fed into tissue. Furthermore, multiple wave shape tables can be created, stored and applied to tissue.

According to various aspects, a method comprises creating various types of lookup tables in memory such as lookup tables generated by direct digital synthesis (DDS) circuit and stored within FPGAs, for example. Waveforms may be stored in the DDS table or tables as particular wave shapes. Examples of wave shapes in the RF/Electrosurgery tissue treatment field include high crest factor RF signals, which may be used for surface coagulation in an RF mode, for example, low crest factor RF signals, which may be used for deeper penetration into tissue in an RF mode, for example, and waveforms that promote efficient touch-up coagulation, for example. In one aspect, the crest factor (CF) may be defined as the ratio of the peak signal to the root-mean-square (RMS) signal.

The present disclosure provides for the creation of multiple wave shape tables that allow for switching on the fly, either manually or automatically, between the wave shapes based on tissue effect desired. Switching could be based on tissue parameters, such as, for example, tissue impedance and/or other factors. In addition to a traditional sine wave shape, in one aspect a generator may be configured to provide a wave shape that maximizes the power into tissue per cycle. According to one aspect, the wave shape may be a trapezoid wave, a sine or cosine wave, a square wave, a triangle wave, or any combination thereof. In one aspect, a generator may be configured to provide a wave shape or shapes that are synchronized in such way that they make maximizing power delivery in the case that both RF and ultrasonic energy modalities are driven, either simultaneously or sequentially. In one aspect, a generator may be configured to provide a waveform that drives both ultrasonic and RF therapeutic energy simultaneously while maintaining ultrasonic frequency lock. In one aspect, the generator may contain or be associated with a device that provides a circuit topology that enables simultaneously driving RF and ultrasonic energy. In one aspect, a generator may be configured to provide custom wave shapes that are specific to a surgical instrument and the tissue effects provided by such a surgical instrument. Furthermore, the waveforms may be stored in a generator non-volatile memory or in an instrument memory, such as, for example, an electrically erasable programmable read-only memory (EEPROM). The waveform or waveforms may be fetched upon instrument connection to a generator.

Figure 1:
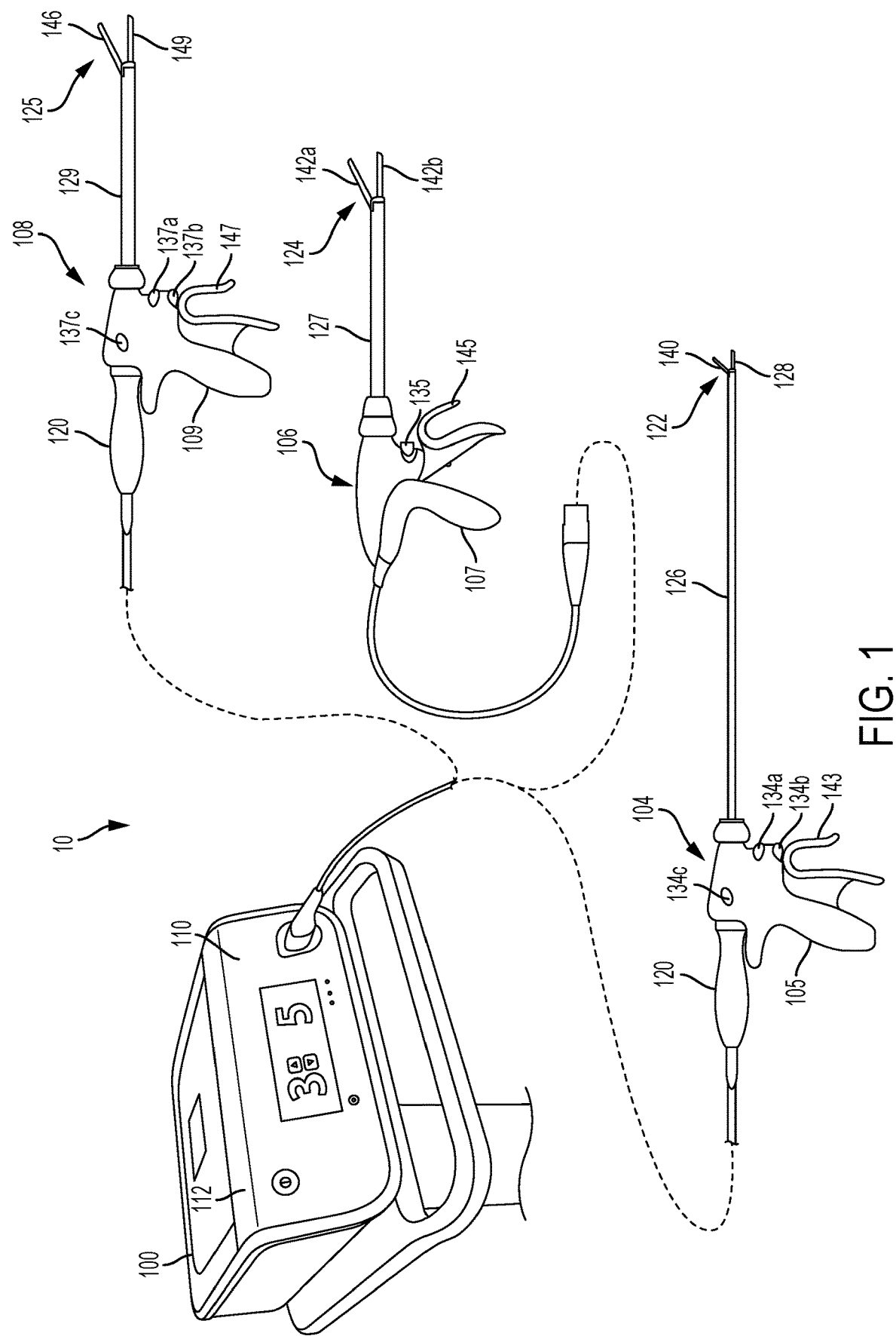
FIG. 1 illustrates one form of a surgical system comprising a generator and various surgical instruments usable therewith.
Figure 2:
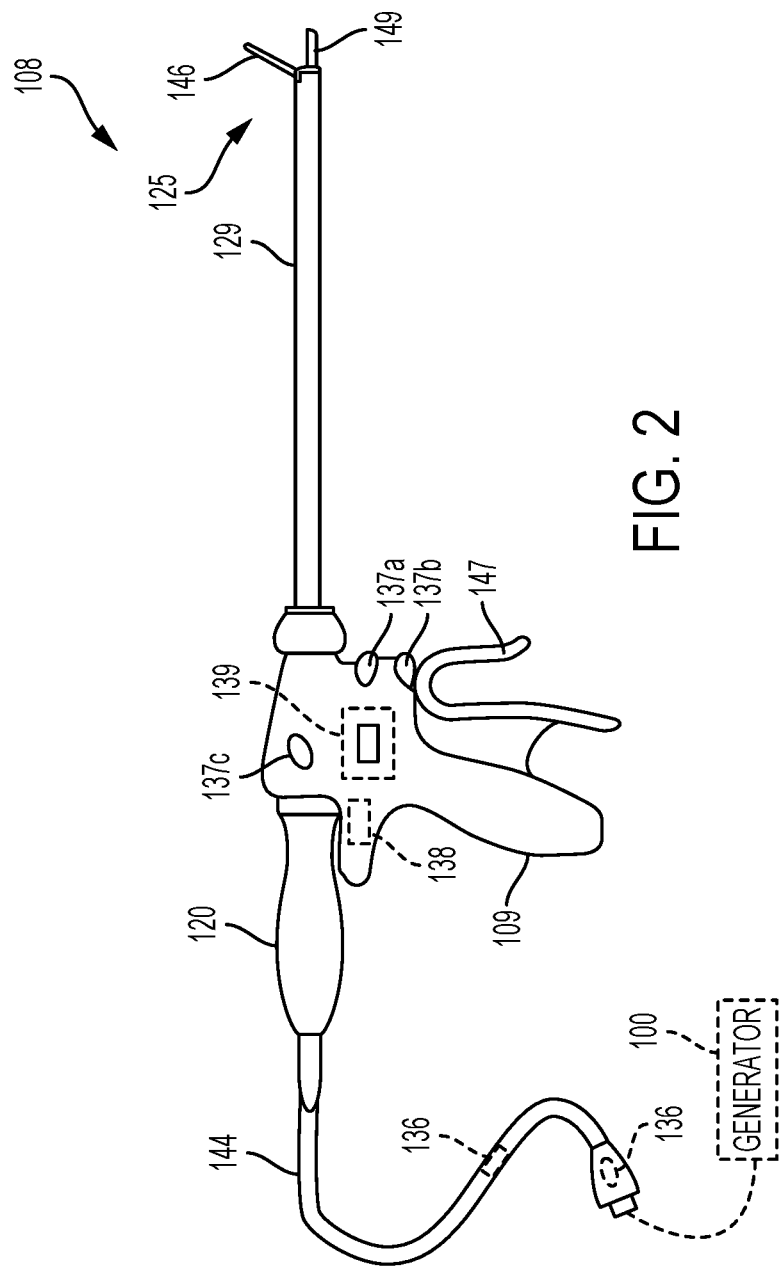
FIG. 2 is a diagram of the combination electrosurgical and ultrasonic instrument shown in FIG. 1.

With reference to FIGS. 1-5, one form of a surgical system 10 including a surgical instrument is illustrated. FIG. 1 illustrates one form of a surgical system 10 comprising a generator 100 and various surgical instruments 104, 106, 108 usable therewith, where the surgical instrument 104 is an ultrasonic surgical instrument, the surgical instrument 106 is an RF electrosurgical instrument 106, and the multifunction surgical instrument 108 is a combination ultrasonic/RF electrosurgical instrument. FIG. 2 is a diagram of the multifunction surgical instrument 108 shown in FIG. 1. With reference to both FIGS. 1 and 2, the generator 100 is configurable for use with a variety of surgical instruments.

According to various forms, the generator 100 may be configurable for use with different surgical instruments of different types including, for example, ultrasonic surgical instruments 104, RF electrosurgical instruments 106, and multifunction surgical instruments 108 that integrate RF and ultrasonic energies delivered simultaneously from the generator 100. Although in the form of FIG. 1, the generator 100 is shown separate from the surgical instruments 104, 106, 108 in one form, the generator 100 may be formed integrally with any of the surgical instruments 104, 106, 108 to form a unitary surgical system. The generator 100 comprises an input device 110 located on a front panel of the generator 100 console. The input device 110 may comprise any suitable device that generates signals suitable for programming the operation of the generator 100.

FIG. 1 illustrates a generator 100 configured to drive multiple surgical instruments 104, 106, 108. The first surgical instrument 104 is an ultrasonic surgical instrument 104 and comprises a handpiece 105 (HP), an ultrasonic transducer 120, a shaft 126, and an end effector 122. The end effector 122 comprises an ultrasonic blade 128 acoustically coupled to the ultrasonic transducer 120 and a clamp arm 140. The handpiece 105 comprises a trigger 143 to operate the clamp arm 140 and a combination of the toggle buttons 134a, 134b, 134c to energize and drive the ultrasonic blade 128 or other function. The toggle buttons 134a, 134b, 134c can be configured to energize the ultrasonic transducer 120 with the generator 100.

Still with reference to FIG. 1, the generator 100 also is configured to drive a second surgical instrument 106. The second surgical instrument 106 is an RF electrosurgical instrument and comprises a handpiece 107 (HP), a shaft 127, and an end effector 124. The end effector 124 comprises electrodes in the clamp arms 142a, 142b and return through an electrical conductor portion of the shaft 127. The electrodes are coupled to and energized by a bipolar energy source within the generator 100. The handpiece 107 comprises a trigger 145 to operate the clamp arms 142a, 142b and an energy button 135 to actuate an energy switch to energize the electrodes in the end effector 124.

Still with reference to FIG. 1, the generator 100 also is configured to drive a multifunction surgical instrument 108. The multifunction surgical instrument 108 comprises a handpiece 109 (HP), a shaft 129, and an end effector 125. The end effector comprises an ultrasonic blade 149 and a clamp arm 146. The ultrasonic blade 149 is acoustically coupled to the ultrasonic transducer 120. The handpiece 109 comprises a trigger 147 to operate the clamp arm 146 and a combination of the toggle buttons 137a, 137b, 137c to energize and drive the ultrasonic blade 149 or other function. The toggle buttons 137a, 137b, 137c can be configured to energize the ultrasonic transducer 120 with the generator 100 and energize the ultrasonic blade 149 with a bipolar energy source also contained within the generator 100.

With reference to both FIGS. 1 and 2, the generator 100 is configurable for use with a variety of surgical instruments. According to various forms, the generator 100 may be configurable for use with different surgical instruments of different types including, for example, the ultrasonic surgical instrument 104, the RF electrosurgical instrument 106, and the multifunction surgical instrument 108 that integrate RF and ultrasonic energies delivered simultaneously from the generator 100. Although in the form of FIG. 1, the generator 100 is shown separate from the surgical instruments 104, 106, 108, in one form, the generator 100 may be formed integrally with any one of the surgical instruments 104, 106, 108 to form a unitary surgical system. The generator 100 comprises an input device 110 located on a front panel of the generator 100 console. The input device 110 may comprise any suitable device that generates signals suitable for programming the operation of the generator 100. The generator 100 also may comprise one or more output devices 112.

With reference now to FIG. 2, the generator 100 is coupled to the multifunction surgical instrument 108. The generator 100 is coupled to the ultrasonic transducer 120 and electrodes located in the clamp arm 146 via a cable 144. The ultrasonic transducer 120 and a waveguide extending through a shaft 129 (waveguide not shown in FIG. 2) may collectively form an ultrasonic drive system driving an ultrasonic blade 149 of an end effector 125. The end effector 125 further may comprise a clamp arm 146 to clamp tissue located between the clamp arm 146 and the ultrasonic blade 149. The clamp arm 146 comprises one or more than one an electrode coupled to the a pole of the generator 100 (e.g., a positive pole). The ultrasonic blade 149 forms the second pole (e.g., the negative pole) and is also coupled to the generator 100. RF energy is applied to the electrode(s) in the clamp arm 146, through the tissue located between the clamp arm 146 and the ultrasonic blade 149, and through the ultrasonic blade 149 back to the generator 100 via the cable 144. In one form, the generator 100 may be configured to produce a drive signal of a particular voltage, current, and/or frequency output signal that can be varied or otherwise modified with high resolution, accuracy, and repeatability suitable for driving an ultrasonic transducer 120 and applying RF energy to tissue.

Still with reference to FIG. 2, It will be appreciated that the multifunction surgical instrument 108 may comprise any combination of the toggle buttons 137*a*, 137*b*, 134*c*. For example, the multifunction surgical instrument 108 could be configured to have only two toggle buttons: a toggle button 137*a* for producing maximum ultrasonic energy output and a toggle button 137*b* for producing a pulsed output at either the maximum or less than maximum power level. In this way, the drive signal output configuration of the generator 100 could be 5 continuous signals and 5 or 4 or 3 or 2 or 1 pulsed signals. In certain forms, the specific drive signal configuration may be controlled based upon, for example, EEPROM settings in the generator 100 and/or user power level selection(s).

In certain forms, a two-position switch may be provided as an alternative to a toggle button 137*c*. For example, the multifunction surgical instrument 108 may include a toggle button 137*a* for producing a continuous output at a maximum power level and a two-position toggle button 137*b*. In a first detented position, toggle button 137*b* may produce a continuous output at a less than maximum power level, and in a second detented position the toggle button 137*b* may produce a pulsed output (e.g., at either a maximum or less than maximum power level, depending upon the EEPROM settings). Any one of the buttons 137*a*, 137*b*, 137*c* may be configured to activate RF energy and apply the RF energy to the end effector 125.

Still with reference to FIG. 2, forms of the generator 100 may enable communication with instrument-based data circuits. For example, the generator 100 may be configured to communicate with a first data circuit 136 and/or a second data circuit 138. For example, the first data circuit 136 may indicate a burn-in frequency slope, as described herein. Additionally or alternatively, any type of information may be communicated to second data circuit for storage therein via a data circuit interface (e.g., using a logic device). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 100 and provide an indication to a user (e.g., a light emitting diode (LED) indication or other visible indication) based on the received data. The second data circuit 138 contained in the multifunction surgical instrument 108. In some forms, the second data circuit 138 may be implemented in a many similar to that of the first data circuit 136 described herein. An instrument interface circuit may comprise a second data circuit interface to enable this communication. In one form, the second data circuit interface may comprise a tri-state digital interface, although other interfaces also may be used. In certain forms, the second data circuit may generally be any circuit for transmitting and/or receiving data. In one form, for example, the second data circuit may store information pertaining to the particular surgical instrument 104, 106, 108 with which it is associated. Such information may include, for example, a model number, a serial number, a number of operations in which the surgical instrument 104, 106, 108 has been used, and/or any other type of information. In the example of FIG. 2, the second data circuit 138 may store information about the electrical and/or ultrasonic properties of an associated ultrasonic transducer 120, end effector 125, ultrasonic energy drive system, or RF electrosurgical energy drive system. Various processes and techniques described herein may be executed by a generator. It will be appreciated, however, that in certain example forms, all or a part of these processes and techniques may be performed by internal logic 139 located in the multifunction surgical instrument 108.

Figure 3:
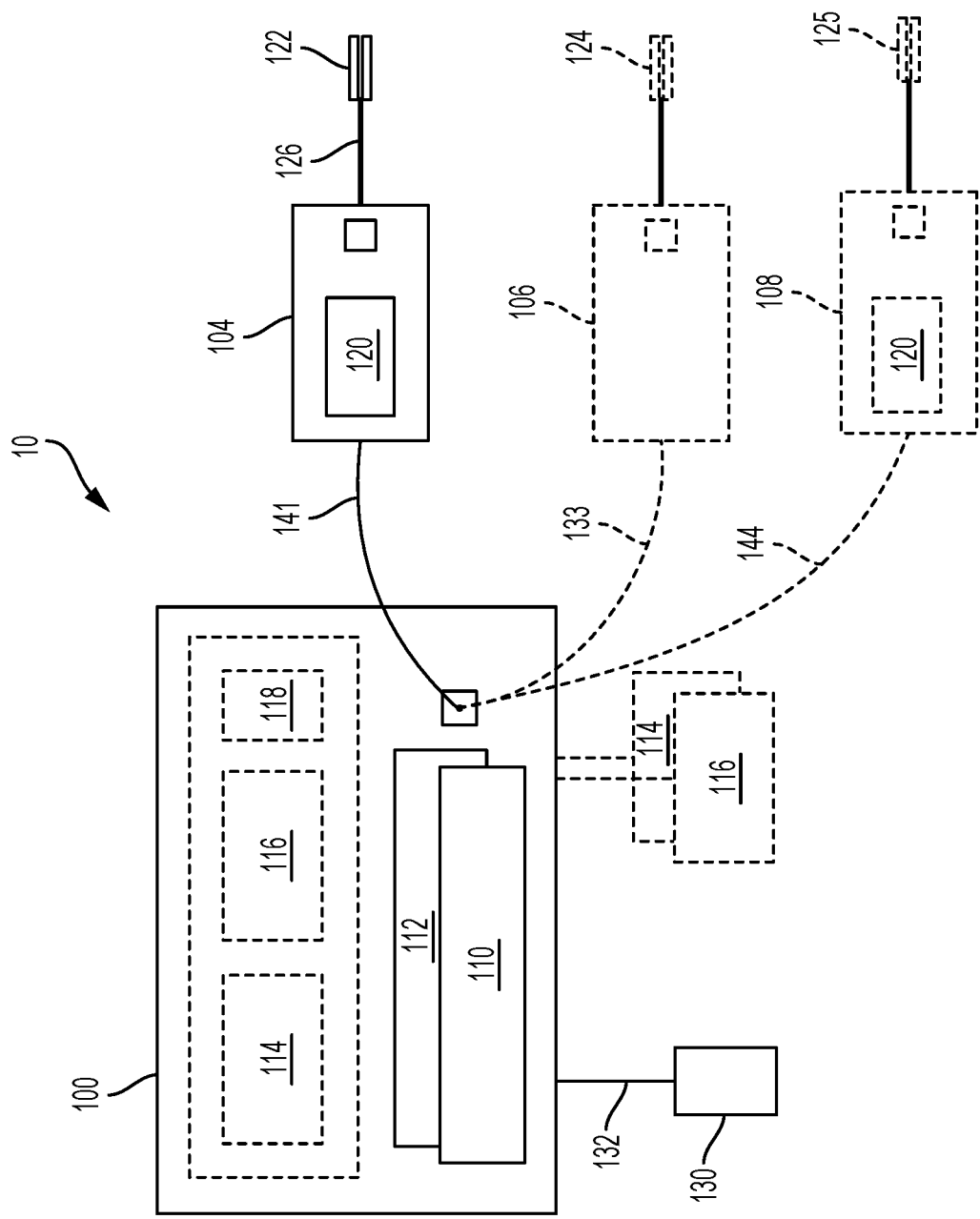
FIG. 3 is a diagram of the surgical system shown in FIG. 1.

FIG. 3 is a diagram of the surgical system 10 of FIG. 1. In various forms, the generator 100 may comprise several separate functional elements, such as modules and/or blocks. Different functional elements or modules may be configured for driving the different kinds of surgical instruments 104, 106, 108. For example, an ultrasonic drive circuit 114 may drive ultrasonic devices such as the surgical instrument 104 via a cable 141. An electrosurgery/RF drive circuit 116 may drive the RF electrosurgical instrument 106 via a cable 133. The respective drive circuits 114, 116, 118 may be combined as a combined RF/ultrasonic drive circuit 118 to generate both respective drive signals for driving multifunction surgical instruments 108 via a cable 144. In various forms, the ultrasonic drive circuit 114 and/or the electrosurgery/RF drive circuit 116 each may be formed integrally or externally with the generator 100. Alternatively, one or more of the drive circuits 114, 116, 118 may be provided as a separate circuit module electrically coupled to the generator 100. (The drive circuits 114, 116, 118 are shown in phantom to illustrate this option.) Also, in some forms, the electrosurgery/RF drive circuit 116 may be formed integrally with the ultrasonic drive circuit 114, or vice versa. Also, in some forms, the generator 100 may be omitted entirely and the drive circuits 114, 116, 118 may be executed by processors or other hardware within the respective surgical instruments 104, 106, 108.

In other forms, the electrical outputs of the ultrasonic drive circuit 114 and the electrosurgery/RF drive circuit 116 may be combined into a single electrical signal capable of driving the multifunction surgical instrument 108 simultaneously with electrosurgical RF and ultrasonic energies. This single electrical drive signal may be produced by the combination drive circuit 118. The multifunction surgical instrument 108 comprises an ultrasonic transducer 120 coupled to an ultrasonic blade and one or more electrodes in the end effector 125 to receive ultrasonic and electrosurgical RF energy. The multifunction surgical instrument 108 comprises signal processing components to split the combined RF/ultrasonic energy signal such that the RF signal can be delivered to the electrodes in the end effector 125 and the ultrasonic signal can be delivered to the ultrasonic transducer 120.

In accordance with the described forms, the ultrasonic drive circuit 114 may produce a drive signal or signals of particular voltages, currents, and frequencies, e.g., 55,500 cycles per second (Hz). The drive signal or signals may be provided to the ultrasonic surgical instrument 104, and specifically to the ultrasonic transducer 120, which may operate, for example, as described above. The ultrasonic transducer 120 and a waveguide extending through the shaft 126 (waveguide not shown) may collectively form an ultrasonic drive system driving an ultrasonic blade 128 of an end effector 122. In one form, the generator 100 may be configured to produce a drive signal of a particular voltage, current, and/or frequency output signal that can be stepped or otherwise modified with high resolution, accuracy, and repeatability.

The generator 100 may be activated to provide the drive signal to the ultrasonic transducer 120 in any suitable manner. For example, the generator 100 may comprise a foot switch 130 coupled to the generator 100 via a foot switch cable 132. A clinician may activate the ultrasonic transducer 120 by depressing the foot switch 130. In addition, or instead of the foot switch 130 some forms of the ultrasonic surgical instrument 104 may utilize one or more switches positioned on the handpiece that, when activated, may cause the generator 100 to activate the ultrasonic transducer 120. In one form, for example, the one or more switches may comprise a pair of toggle buttons 137a, 137b (FIG. 2), for example, to determine an operating mode of the ultrasonic surgical instrument 104. When the toggle button 137a is depressed, for example, the generator 100 may provide a maximum drive signal to the ultrasonic transducer 120, causing it to produce maximum ultrasonic energy output. Depressing toggle button 137b may cause the generator 100 to provide a user-selectable drive signal to the ultrasonic transducer 120, causing it to produce less than the maximum ultrasonic energy output.

Additionally or alternatively, the one or more switches may comprise a toggle button 137c that, when depressed, causes the generator 100 to provide a pulsed output. The pulses may be provided at any suitable frequency and grouping, for example. In certain forms, the power level of the pulses may be the power levels associated with toggle buttons 137a, 137b (maximum, less than maximum), for example.

It will be appreciated that the ultrasonic surgical instrument 104 and/or the multifunction surgical instrument 108 may comprise any combination of the toggle buttons 137a, 137b, 137c. For example, the multifunction surgical instrument 108 could be configured to have only two toggle buttons: a toggle button 137a for producing maximum ultrasonic energy output and a toggle button 137c for producing a pulsed output at either the maximum or less than maximum power level. In this way, the drive signal output configuration of the generator 100 could be 5 continuous signals and 5 or 4 or 3 or 2 or 1 pulsed signals. In certain forms, the specific drive signal configuration may be controlled based upon, for example, EEPROM settings in the generator 100 and/or user power level selection(s).

In certain forms, a two-position switch may be provided as an alternative to a toggle button 137c. For example, the ultrasonic surgical instrument 104 may include a toggle button 137a for producing a continuous output at a maximum power level and a two-position toggle button 137b. In a first detented position, toggle button 137b may produce a continuous output at a less than maximum power level, and in a second detented position the toggle button 137b may produce a pulsed output (e.g., at either a maximum or less than maximum power level, depending upon the EEPROM settings).

In accordance with the described forms, the electrosurgery/RF drive circuit 116 may generate a drive signal or signals with output power sufficient to perform bipolar electrosurgery using RF energy. In bipolar electrosurgery applications, the drive signal may be provided, for example, to electrodes located in the end effector 124 of the RF electrosurgical instrument 106, for example. Accordingly, the generator 100 may be configured for therapeutic purposes by applying electrical energy to the tissue sufficient for treating the tissue (e.g., coagulation, cauterization, tissue welding). The generator 100 may be configured for sub-therapeutic purposes by applying electrical energy to the tissue for monitoring parameters of the tissue during a procedure.

As previously discussed, the combination drive circuit 118 may be configured to drive both ultrasonic and RF electrosurgical energies. The ultrasonic and RF electrosurgical energies may be delivered though separate output ports of the generator 100 as separate signals or though a single port of the generator 100 as a single signal that is a combination of the ultrasonic and RF electrosurgical energies. In the latter case, the single signal can be separated by circuits located in the surgical instruments 104, 106, 108.

The surgical instruments 104, 106, 108 additionally or alternatively may comprise a switch to indicate a position of a jaw closure trigger for operating jaws of the end effector 122, 124, 125. Also, in some forms, the generator 100 may be activated based on the position of the jaw closure trigger, (e.g., as the clinician depresses the jaw closure trigger to close the jaws, ultrasonic energy may be applied).

The generator 100 may comprise an input device 110 (FIG. 1) located, for example, on a front panel of the generator 100 console. The input device 110 may comprise any suitable device that generates signals suitable for programming the operation of the generator 100. In operation, the user can program or otherwise control operation of the generator 100 using the input device 110. The input device 110 may comprise any suitable device that generates signals that can be used by the generator (e.g., by one or more processors contained in the generator) to control the operation of the generator 100 (e.g., operation of the ultrasonic drive circuit 114, electrosurgery/RF drive circuit 116, combined RF/ultrasonic drive circuit 118). In various forms, the input device 110 includes one or more of buttons, switches, thumbwheels, keyboard, keypad, touch screen monitor, pointing device, remote connection to a general purpose or dedicated computer. In other forms, the input device 110 may comprise a suitable user interface, such as one or more user interface screens displayed on a touch screen monitor, for example. Accordingly, by way of the input device 110, the user can set or program various operating parameters of the generator, such as, for example, current (I), voltage (V), frequency (f), and/or period (T) of a drive signal or signals generated by the ultrasonic drive circuit 114 and/or electrosurgery/RF drive circuit 116.

The generator 100 also may comprise an output device 112 (FIG. 1), such as an output indicator, located, for example, on a front panel of the generator 100 console. The output device 112 includes one or more devices for providing a sensory feedback to a user. Such devices may comprise, for example, visual feedback devices (e.g., a visual feedback device may comprise incandescent lamps, LEDs, graphical user interface, display, analog indicator, digital indicator, bar graph display, digital alphanumeric display, liquid crystal display (LCD) screen, light emitting diode (LED) indicators), audio feedback devices (e.g., an audio feedback device may comprise speaker, buzzer, audible, computer generated tone, computerized speech, voice user interface (VUI) to interact with computers through a voice/speech platform), or tactile feedback devices (e.g., a tactile feedback device comprises any type of vibratory feedback, haptic actuator).

Although certain modules and/or blocks of the generator 100 may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Also, in some forms, the various modules described herein may be implemented utilizing similar hardware positioned within the surgical instruments 104, 106, 108 (i.e., the external generator 100 may be omitted).

In one form, the ultrasonic drive circuit 114, electrosurgery/RF drive circuit 116, and/or the combination drive circuit 118 may comprise one or more embedded applications implemented as firmware, software, hardware, or any combination thereof. The drive circuits 114, 116, 118 may comprise various executable modules such as software, programs, data, drivers, application program interfaces (APIs), and so forth. The firmware may be stored in non-volatile memory (NVM), such as in bit masked read-only memory (ROM) or flash memory. In various implementations, storing the firmware in ROM may preserve flash memory. The NVM may comprise other types of memory including, for example, programmable ROM (PROM), erasable programmable ROM (EPROM), EEPROM, or battery backed random-access memory (RAM) such as dynamic RAM (DRAM), Double-Data-Rate DRAM (DDRAM), and/or synchronous DRAM (SDRAM).

In one form, the drive circuits 114, 116, 118 comprise a hardware component implemented as a processor for executing program instructions for monitoring various measurable characteristics of the surgical instruments 104, 106, 108 and generating a corresponding output control signals for operating the surgical instruments 104, 106, 108. In forms in which the generator 100 is used in conjunction with the multifunction surgical instrument 108, the output control signal may drive the ultrasonic transducer 120 in cutting and/or coagulation operating modes. Electrical characteristics of the multifunction surgical instrument 108 and/or tissue may be measured and used to control operational aspects of the generator 100 and/or provided as feedback to the user. In forms in which the generator 100 is used in conjunction with the multifunction surgical instrument 108, the output control signal may supply electrical energy (e.g., RF energy) to the end effector 125 in cutting, coagulation and/or desiccation modes. Electrical characteristics of the multifunction surgical instrument 108 and/or tissue may be measured and used to control operational aspects of the generator 100 and/or provide feedback to the user. In various forms, as previously discussed, the hardware component may be implemented as a DSP, PLD, ASIC, circuits, and/or registers. In one form, the processor may be configured to store and execute computer software program instructions to generate the output signals for driving various components of the surgical instruments 104, 106, 108, such as the ultrasonic transducer 120 and the end effectors 122, 124, 125.

Figure 4:
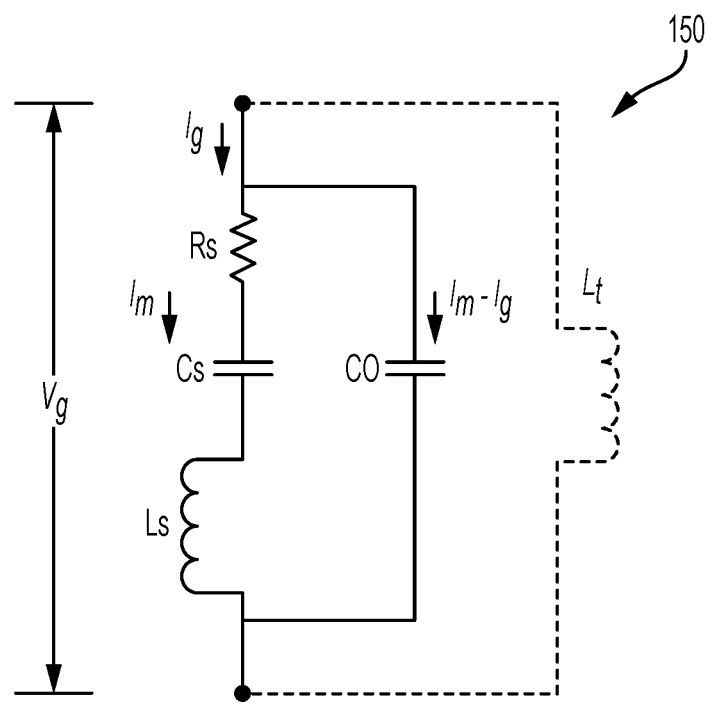
FIG. 4 is a model illustrating motional branch current in one form.

FIG. 4 illustrates an equivalent circuit 150 of an ultrasonic transducer, such as the ultrasonic transducer 120, according to one form. The equivalent circuit 150 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g$-$I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 4) for tuning out in a parallel resonance circuit the static capacitance Co at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance Co at a single resonant frequency, accurate control of the motional branch current $I_m$ is assured only at that frequency, and as frequency shifts down with transducer temperature, accurate control of the motional branch current is compromised.

Forms of the generator 100 do not rely on a tuning inductor $L_t$ to monitor the motional branch current $I_m$. Instead, the generator 100 may use the measured value of the static capacitance $C_o$ in between applications of power for a specific ultrasonic surgical instrument 104 (along with drive signal voltage and current feedback data) to determine values of the motional branch current $I_m$ on a dynamic and ongoing basis (e.g., in real-time). Such forms of the generator 100 are therefore able to provide virtual tuning to simulate a system that is tuned or resonant with any value of static capacitance $C_o$ at any frequency, and not just at single resonant frequency dictated by a nominal value of the static capacitance $C_o$.

Figure 5:
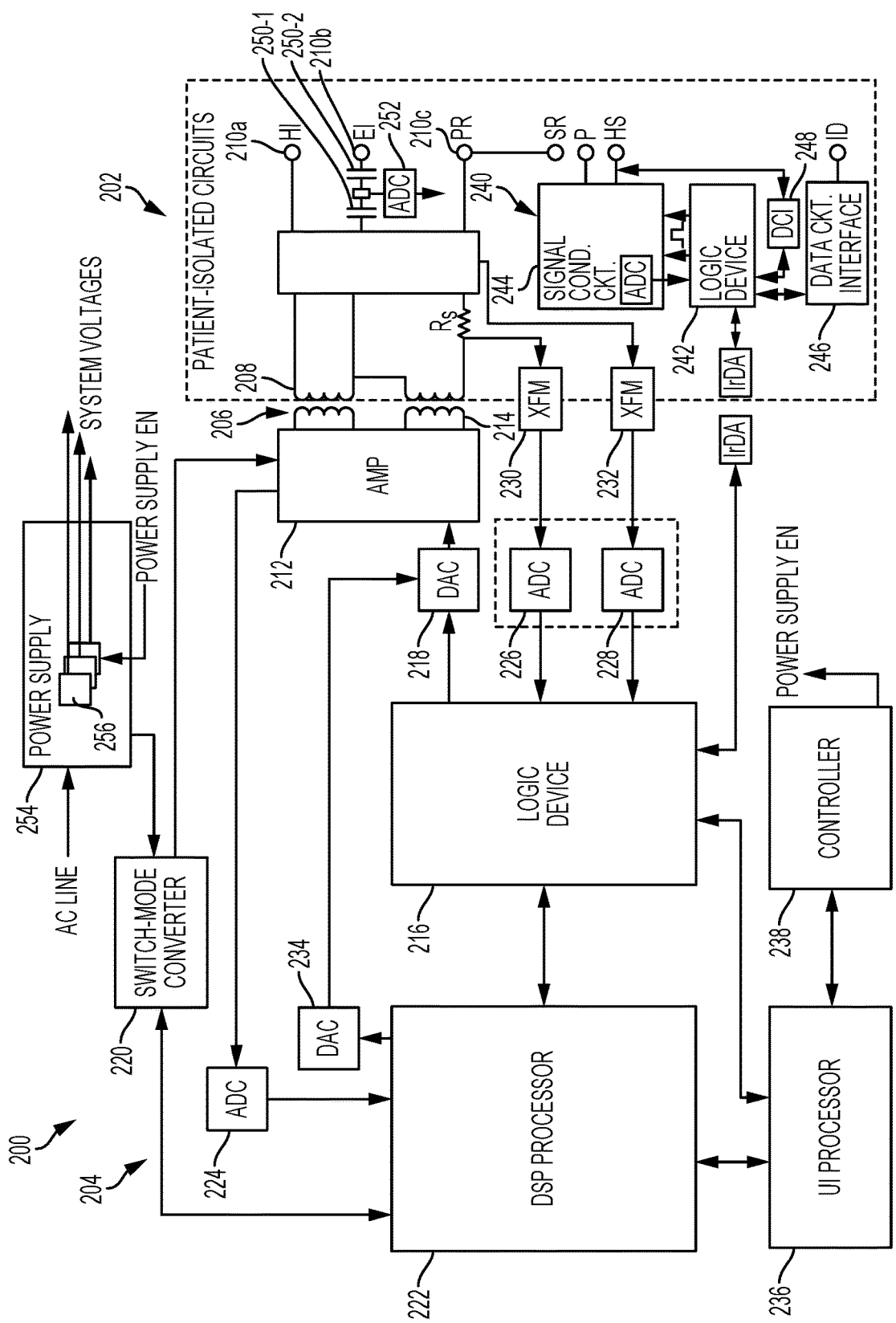
FIG. 5 is a structural view of a generator architecture in one form.

FIG. 5 is a simplified block diagram of a generator 200, which is one form of the generator 100 (FIGS. 1-3). The generator 200 is configured to provide inductorless tuning as described above, among other benefits. Additional details of the generator 200 are described in commonly assigned and contemporaneously filed U.S. Pat. No. 9,060,775, titled SURGICAL GENERATOR FOR ULTRASONIC AND ELECTROSURGICAL DEVICES, the disclosure of which is incorporated herein by reference in its entirety. With reference to FIG. 5, the generator 200 may comprise a patient isolated stage 202 in communication with a non-isolated stage 204 via a power transformer 206. A secondary winding 208 of the power transformer 206 is contained in the isolated stage 202 and may comprise a tapped configuration (e.g., a center-tapped or a non-center-tapped configuration) to define drive signal outputs 210a, 210b, 210c for delivering drive signals to different surgical instruments, such as, for example, an ultrasonic surgical instrument 104, an RF electrosurgical instrument 106, and a multifunction surgical instrument 108. In particular, drive signal outputs 210a, 210c may output an ultrasonic drive signal (e.g., a 420V RMS drive signal) to an ultrasonic surgical instrument 104, and drive signal outputs 210b, 210c may output an electrosurgical drive signal (e.g., a 100V RMS drive signal) to an RF electrosurgical instrument 106, with the drive signal output 2160b corresponding to the center tap of the power transformer 206.

In certain forms, the ultrasonic and electrosurgical drive signals may be provided simultaneously to distinct surgical instruments and/or to a single surgical instrument having the capability to deliver both ultrasonic and electrosurgical energy to tissue, such as the multifunction surgical instrument 108 (FIGS. 1-3). It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue while the electrosurgical RF energy may be employed for vessel sealing.

The non-isolated stage 204 may comprise a power amplifier 212 having an output connected to a primary winding 214 of the power transformer 206. In certain forms the power amplifier 212 may be comprise a push-pull amplifier. For example, the non-isolated stage 204 may further comprise a logic device 216 for supplying a digital output to a DAC circuit 218, which in turn supplies a corresponding analog signal to an input of the power amplifier 212. In certain forms the logic device 216 may comprise a programmable gate array (PGA), a FPGA, programmable logic device (PLD), among other logic circuits, for example. The logic device 216, by virtue of controlling the input of the power amplifier 212 via the DAC circuit 218, may therefore control any of a number of parameters (e.g., frequency, waveform shape, waveform amplitude) of drive signals appearing at the drive signal outputs 210a, 210b, 210c. In certain forms and as discussed below, the logic device 216, in conjunction with a processor (e.g., a digital signal processor discussed below), may implement a number of digital signal processing (DSP)-based and/or other control algorithms to control parameters of the drive signals output by the generator 200.

Power may be supplied to a power rail of the power amplifier 212 by a switch-mode regulator 220, e.g., power converter. In certain forms the switch-mode regulator 220 may comprise an adjustable buck regulator, for example. The non-isolated stage 204 may further comprise a first processor 222, which in one form may comprise a DSP processor such as an Analog Devices ADSP-21469 SHARC DSP, available from Analog Devices, Norwood, Mass., for example, although in various forms any suitable processor may be employed. In certain forms the DSP processor 222 may control operation of the switch-mode regulator 220 responsive to voltage feedback data received from the power amplifier 212 by the DSP processor 222 via an analog-to-digital converter (ADC) circuit 224. In one form, for example, the DSP processor 222 may receive as input, via the ADC circuit 224, the waveform envelope of a signal (e.g., an RF signal) being amplified by the power amplifier 212. The DSP processor 222 may then control the switch-mode regulator 220 (e.g., via a pulse-width modulated (PWM) output) such that the rail voltage supplied to the power amplifier 212 tracks the waveform envelope of the amplified signal. By dynamically modulating the rail voltage of the power amplifier 212 based on the waveform envelope, the efficiency of the power amplifier 212 may be significantly improved relative to a fixed rail voltage amplifier schemes.

In certain forms, the logic device 216, in conjunction with the DSP processor 222, may implement a digital synthesis circuit such as a DDS (see e.g., FIGS. 13, 14) control scheme to control the waveform shape, frequency and/or amplitude of drive signals output by the generator 200. In one form, for example, the logic device 216 may implement a DDS control algorithm by recalling waveform samples stored in a dynamically-updated lookup table (LUT), such as a RAM LUT, which may be embedded in an FPGA. This control algorithm is particularly useful for ultrasonic applications in which an ultrasonic transducer, such as the ultrasonic transducer 120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 200 is impacted by various sources of distortion present in the output drive circuit (e.g., the power transformer 206, the power amplifier 212), voltage and current feedback data based on the drive signal may be input into an algorithm, such as an error control algorithm implemented by the DSP processor 222, which compensates for distortion by suitably pre-distorting or modifying the waveform samples stored in the LUT on a dynamic, ongoing basis (e.g., in real-time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 204 may further comprise a first ADC circuit 226 and a second ADC circuit 228 coupled to the output of the power transformer 206 via respective isolation transformers 230, 232 for respectively sampling the voltage and current of drive signals output by the generator 200. In certain forms, the ADC circuits 226, 228 may be configured to sample at high speeds (e.g., 80 mega samples per second [MSPS]) to enable oversampling of the drive signals. In one form, for example, the sampling speed of the ADC circuits 226, 228 may enable approximately 200× (depending on frequency) oversampling of the drive signals. In certain forms, the sampling operations of the ADC circuit 226, 228 may be performed by a single ADC circuit receiving input voltage and current signals via a two-way multiplexer. The use of high-speed sampling in forms of the generator 200 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 226, 228 may be received and processed (e.g., first-in-first-out [FIFO] buffer, multiplexer, etc.) by the logic device 216 and stored in data memory for subsequent retrieval by, for example, the DSP processor 222. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 216 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 222, for example, with the frequency control signal being supplied as input to a DDS control algorithm implemented by the logic device 216.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 222. Variables controlled by the control algorithm to suitably control the current amplitude of the drive signal may include, for example, the scaling of the LUT waveform samples stored in the logic device 216 and/or the full-scale output voltage of the DAC circuit 218 (which supplies the input to the power amplifier 212) via a DAC circuit 234.

The non-isolated stage 204 may further comprise a second processor 236 for providing, among other things user interface (UI) functionality. In one form, the UI processor 236 may comprise an Atmel AT91SAM9263 processor having an ARM 926EJ-S core, available from Atmel Corporation, San Jose, Calif., for example. Examples of UI functionality supported by the UI processor 236 may include audible and visual user feedback, communication with peripheral devices (e.g., via a Universal Serial Bus [USB] interface), communication with the foot switch 130, communication with an input device 110 (e.g., a touch screen display) and communication with an output device 112 (e.g., a speaker), as shown in FIGS. 1 and 3. The UI processor 236 may communicate with the DSP processor 222 and the logic device 216 (e.g., via serial peripheral interface [SPI] buses). Although the UI processor 236 may primarily support UI functionality, it may also coordinate with the DSP processor 222 to implement hazard mitigation in certain forms. For example, the UI processor 236 may be programmed to monitor various aspects of user input and/or other inputs (e.g., touch screen inputs, foot switch 130 inputs as shown in FIG. 3, temperature sensor inputs) and may disable the drive output of the generator 200 when an erroneous condition is detected.

In certain forms, both the DSP processor 222 and the UI processor 236, for example, may determine and monitor the operating state of the generator 200. For the DSP processor 222, the operating state of the generator 200 may dictate, for example, which control and/or diagnostic processes are implemented by the DSP processor 222. For the UI processor 236, the operating state of the generator 200 may dictate, for example, which elements of a user interface (e.g., display screens, sounds) are presented to a user. The respective DSP and UI processors 222, 236 may independently maintain the current operating state of the generator 200 and recognize and evaluate possible transitions out of the current operating state. The DSP processor 222 may function as the master in this relationship and determine when transitions between operating states are to occur. The UI processor 236 may be aware of valid transitions between operating states and may confirm if a particular transition is appropriate. For example, when the DSP processor 222 instructs the UI processor 236 to transition to a specific state, the UI processor 236 may verify that requested transition is valid. In the event that a requested transition between states is determined to be invalid by the UI processor 236, the UI processor 236 may cause the generator 200 to enter a failure mode.

The non-isolated stage 204 may further comprise a controller 238 for monitoring input devices 110 (e.g., a capacitive touch sensor used for turning the generator 200 on and off, a capacitive touch screen). In certain forms, the controller 238 may comprise at least one processor and/or other controller device in communication with the UI processor 236. In one form, for example, the controller 238 may comprise a processor (e.g., a Mega168 8-bit controller available from Atmel) configured to monitor user input provided via one or more capacitive touch sensors. In one form, the controller 238 may comprise a touch screen controller (e.g., a QT5480 touch screen controller available from Atmel) to control and manage the acquisition of touch data from a capacitive touch screen.

In certain forms, when the generator 200 is in a "power off" state, the controller 238 may continue to receive operating power (e.g., via a line from a power supply of the generator 200, such as the power supply 254 discussed below). In this way, the controller 196 may continue to monitor an input device 110 (e.g., a capacitive touch sensor located on a front panel of the generator 200) for turning the generator 200 on and off. When the generator 200 is in the power off state, the controller 238 may wake the power supply (e.g., enable operation of one or more DC/DC voltage converters 256 of the power supply 254) if activation of the "on/off" input device 110 by a user is detected. The controller 238 may therefore initiate a sequence for transitioning the generator 200 to a "power on" state. Conversely, the controller 238 may initiate a sequence for transitioning the generator 200 to the power off state if activation of the "on/off" input device 110 is detected when the generator 200 is in the power on state. In certain forms, for example, the controller 238 may report activation of the "on/off" input device 110 to the UI processor 236, which in turn implements the necessary process sequence for transitioning the generator 200 to the power off state. In such forms, the controller 196 may have no independent ability for causing the removal of power from the generator 200 after its power on state has been established.

In certain forms, the controller 238 may cause the generator 200 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 202 may comprise an instrument interface circuit 240 to, for example, provide a communication interface between a control circuit of a surgical instrument (e.g., a control circuit comprising handpiece switches) and components of the non-isolated stage 204, such as, for example, the logic device 216, the DSP processor 222 and/or the UI processor 236. The instrument interface circuit 240 may exchange information with components of the non-isolated stage 204 via a communication link that maintains a suitable degree of electrical isolation between the isolated and non-isolated stages 202, 204, such as, for example, an infrared (IR)-based communication link. Power may be supplied to the instrument interface circuit 240 using, for example, a low-dropout voltage regulator powered by an isolation transformer driven from the non-isolated stage 204.

In one form, the instrument interface circuit 240 may comprise a logic circuit 242 (e.g., logic circuit, programmable logic circuit, PGA, FPGA, PLD) in communication with a signal conditioning circuit 244. The signal conditioning circuit 244 may be configured to receive a periodic signal from the logic circuit 242 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 200 to the surgical instrument) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one form, for example, the signal conditioning circuit 244 may comprise an ADC circuit for generating samples of a voltage signal appearing across inputs of the control circuit resulting from passage of interrogation signal therethrough. The logic circuit 242 (or a component of the non-isolated stage 204) may then determine the state or configuration of the control circuit based on the ADC circuit samples.

In one form, the instrument interface circuit 240 may comprise a first data circuit interface 246 to enable information exchange between the logic circuit 242 (or other element of the instrument interface circuit 240) and a first data circuit disposed in or otherwise associated with a surgical instrument. In certain forms, for example, a first data circuit 136 (FIG. 2) may be disposed in a cable integrally attached to a surgical instrument handpiece, or in an adaptor for interfacing a specific surgical instrument type or model with the generator 200. The first data circuit 136 may be implemented in any suitable manner and may communicate with the generator according to any suitable protocol including, for example, as described herein with respect to the first data circuit 136. In certain forms, the first data circuit may comprise a non-volatile storage device, such as an EEPROM device. In certain forms and referring again to FIG. 5, the first data circuit interface 246 may be implemented separately from the logic circuit 242 and comprise suitable circuitry (e.g., discrete logic devices, a processor) to enable communication between the logic circuit 242 and the first data circuit. In other forms, the first data circuit interface 246 may be integral with the logic circuit 242.

In certain forms, the first data circuit 136 *FIG. 2) may store information pertaining to the particular surgical instrument with which it is associated. Such information may include, for example, a model number, a serial number, a number of operations in which the surgical instrument has been used, and/or any other type of information. This information may be read by the instrument interface circuit 240 (e.g., by the logic circuit 242), transferred to a component of the non-isolated stage 204 (e.g., to logic device 216, DSP processor 222 and/or UI processor 236) for presentation to a user via an output device 112 (FIGS. 1 and 3) and/or for controlling a function or operation of the generator 200. Additionally, any type of information may be communicated to first data circuit 136 for storage therein via the first data circuit interface 246 (e.g., using the logic circuit 242). Such information may comprise, for example, an updated number of operations in which the surgical instrument has been used and/or dates and/or times of its usage.

As discussed previously, a surgical instrument may be detachable from a handpiece (e.g., the multifunction surgical instrument 108 may be detachable from the handpiece 109) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 200 may enable communication with instrument-based data circuits. For example, the generator 200 may be configured to communicate with a second data circuit 138 (FIG. 2) contained in an instrument (e.g., the multifunction surgical instrument 108 shown in FIG. 2). In some forms, the second data circuit 138 may be implemented in a many similar to that of the first data circuit 136 (FIG. 2) described herein. The instrument interface circuit 240 may comprise a second data circuit interface 248 to enable this communication. In one form, the second data circuit interface 248 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit 138 (FIG. 2) may store information about the electrical and/or ultrasonic properties of an associated ultrasonic transducer 120, end effector 125, or ultrasonic drive system. For example, the first data circuit 136 (FIG. 2) may indicate a burn-in frequency slope, as described herein. Additionally or alternatively, any type of information may be communicated to second data circuit for storage therein via the second data circuit interface 248 (e.g., using the logic circuit 242). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 200 and provide an indication to a user (e.g., an LED indication or other visible indication) based on the received data.

In certain forms, the second data circuit and the second data circuit interface 248 may be configured such that communication between the logic circuit 242 and the second data circuit can be effected without the need to provide additional conductors for this purpose (e.g., dedicated conductors of a cable connecting a handpiece to the generator 200). In one form, for example, information may be communicated to and from the second data circuit using a 1-wire bus communication scheme implemented on existing cabling, such as one of the conductors used transmit interrogation signals from the signal conditioning circuit 244 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 202 may comprise at least one blocking capacitor 250-1 connected to the drive signal output 210b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 250-2 may be provided in series with the blocking capacitor 250-1, with current leakage from a point between the blocking capacitors 250-1, 250-2 being monitored by, for example, an ADC circuit 252 for sampling a voltage induced by leakage current. The samples may be received by the logic circuit 242, for example. Based changes in the leakage current (as indicated by the voltage samples in the form of FIG. 5), the generator 200 may determine when at least one of the blocking capacitors 250-1, 250-2 has failed. Accordingly, the form of FIG. 5 provides a benefit over single-capacitor designs having a single point of failure.

In certain forms, the non-isolated stage 204 may comprise a power supply 254 for delivering DC power at a suitable voltage and current. The power supply may comprise, for example, a 400 W power supply for delivering a 48 VDC system voltage. The power supply 254 may further comprise one or more DC/DC voltage converters 256 for receiving the output of the power supply to generate DC outputs at the voltages and currents required by the various components of the generator 200. As discussed above in connection with the controller 238, one or more of the DC/DC voltage converters 256 may receive an input from the controller 238 when activation of the "on/off" input device 110 by a user is detected by the controller 238 to enable operation of, or wake, the DC/DC voltage converters 256.

Figure 6:
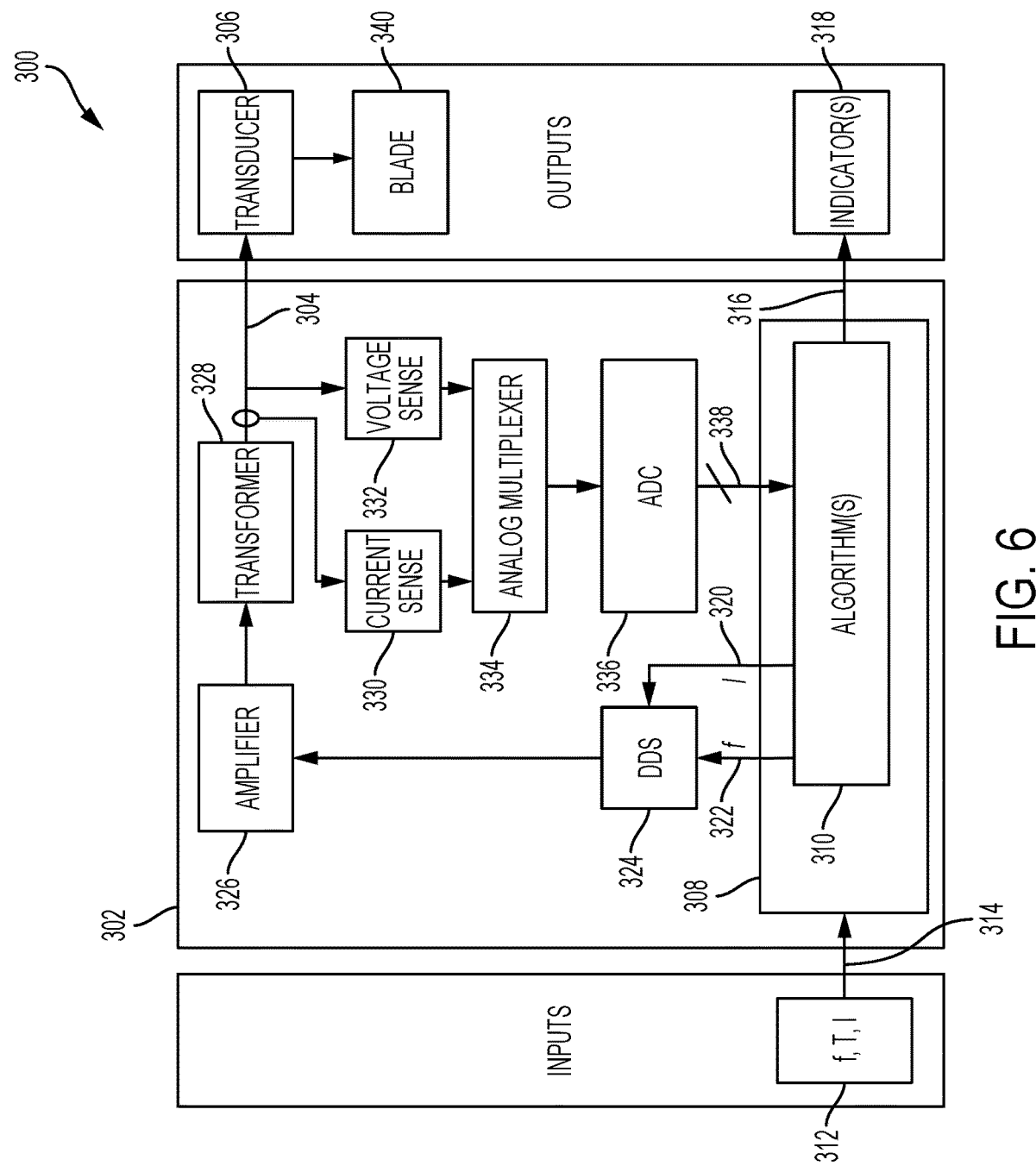
FIG. 6 illustrates one form of a drive system of a generator, which creates the ultrasonic electrical signal for driving an ultrasonic transducer.

FIG. 6 illustrates one form of a drive system 302 of a generator 300, which is one form of the generator 100 (FIGS. 1-3). The generator 300 is configured to provide an ultrasonic electrical signal for driving an ultrasonic transducer (e.g., ultrasonic transducer 120 FIGS. 1-3), also referred to as a drive signal. The generator 300 is similar to and may be interchangeable with the generators 100, 200 (FIGS. 1-3 and 5). The drive system 302 is flexible and can create an ultrasonic electrical drive signal 304 at a desired frequency and power level setting for driving the ultrasonic transducer 306. In various forms, the generator 300 may comprise several separate functional elements, such as modules and/or blocks. Although certain modules and/or blocks may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one form, the generator 300 drive system 302 may comprise one or more embedded applications implemented as firmware, software, hardware, or any combination thereof. The generator 300 drive system 302 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), EEPROM, or battery backed random-access memory (RAM) such as dynamic RAM (DRAM), Double-Data-Rate DRAM (DDRAM), and/or synchronous DRAM (SDRAM).

In one form, the generator 300 drive system 302 comprises a hardware component implemented as a processor 308 for executing program instructions for monitoring various measurable characteristics of the ultrasonic surgical instrument 104 (FIG. 1) and generating an output signal for driving the ultrasonic transducer in cutting and/or coagulation operating modes. It will be appreciated by those skilled in the art that the generator 300 and the drive system 302 may comprise additional or fewer components and only a simplified version of the generator 300 and the drive system 302 are described herein for conciseness and clarity. In various forms, as previously discussed, the hardware component may be implemented as a DSP, PLD, ASIC, circuits, and/or registers. In one form, the processor 308 may be configured to store and execute computer software program instructions to generate the output signals for driving various components of the ultrasonic surgical instrument 104, such as a transducer, an end effector, and/or a blade.

In one form, under control of one or more software program routines, the processor 308 executes the methods in accordance with the described forms to generate an electrical signal output waveform comprising current (I), voltage (V), and/or frequency (f) for various time intervals or periods (T). The stepwise waveforms of the drive signals may be generated by forming a piecewise linear combination of constant functions over a plurality of time intervals created by stepping the generator 300 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the generator 300 include, without limitation, ultrasonic drive signals capable of exciting the ultrasonic transducer 306 in various vibratory modes such as, for example, the primary longitudinal mode and harmonics thereof as well flexural and torsional vibratory modes.

In one form, the executable modules comprise one or more algorithm(s) 310 stored in memory that when executed causes the processor 308 to generate an electrical signal output waveform comprising current (I), voltage (V), and/or frequency (f) for various time intervals or periods (T). The stepwise waveforms of the drive signals may be generated by forming a piecewise linear combination of constant functions over two or more time intervals created by stepping the output drive current (I), voltage (V), and/or frequency (f) of the generator 300. The drive signals may be generated either for predetermined fixed time intervals or periods (T) of time or variable time intervals or periods of time in accordance with the one or more algorithm(s) 310. Under control of the processor 308, the generator 100 outputs (e.g., increases or decreases) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the generator 300 can increase or decrease the step adaptively based on measured system characteristics.

In operation, the user can program the operation of the generator 300 using the input device 312 located on the front panel of the generator 300 console. The input device 312 may comprise any suitable device that generates signals 314 that can be applied to the processor 308 to control the operation of the generator 300. In various forms, the input device 312 includes buttons, switches, thumbwheels, keyboard, keypad, touch screen monitor, pointing device, remote connection to a general purpose or dedicated computer. In other forms, the input device 312 may comprise a suitable user interface. Accordingly, by way of the input device 312, the user can set or program the current (I), voltage (V), frequency (f), and/or period (T) for programming the output of the generator 300. The processor 308 then displays the selected power level by sending a signal on line 316 to an output indicator 318.

In various forms, the output indicator 318 may provide visual, audible, and/or tactile feedback to the surgeon to indicate the status of a surgical procedure, such as, for example, when tissue cutting and coagulating is complete based on a measured characteristic of the ultrasonic surgical instrument 104, e.g., transducer impedance, tissue impedance, or other measurements as subsequently described. By way of example, and not limitation, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through an instrument housing handle assembly.

In one form, the processor 308 may be configured or programmed to generate a digital current signal 320 and a digital frequency signal 322. These digital signals 320, 322 are applied to a digital synthesis circuit such as the DDS circuit 324 (see e.g., FIGS. 13, 14) to adjust the amplitude and the frequency (f) of the ultrasonic electrical drive signal 304 to the transducer. The output of the DDS circuit 324 is applied to a power amplifier 326 whose output is applied to a transformer 328. The output of the transformer 328 is the ultrasonic electrical drive signal 304 applied to the ultrasonic transducer 306, which is coupled to a blade by way of a waveguide. The output of the DDS circuit 324 may be stored in one more memory circuits including volatile (RAM) and non-volatile (ROM) memory circuits.

In one form, the generator 300 comprises one or more measurement modules or components that may be configured to monitor measurable characteristics of the ultrasonic instrument 104 (FIGS. 1, 2) or the multifunction electrosurgical/ultrasonic instrument 108 (FIGS. 1-3). In the illustrated form, the processor 308 may be employed to monitor and calculate system characteristics. As shown, the processor 308 measures the impedance Z of the transducer by monitoring the current supplied to the ultrasonic transducer 306 and the voltage applied to the transducer. In one form, a current sense circuit 330 is employed to sense the current flowing through the transducer and a voltage sense circuit 332 is employed to sense the output voltage applied to the ultrasonic transducer 306. These signals may be applied to the ADC circuit 336 via an analog multiplexer 334 circuit or switching circuit arrangement. The analog multiplexer 334 routes the appropriate analog signal to the ADC circuit 336 for conversion. In other forms, multiple ADC circuits 336 may be employed for each measured characteristic instead of the analog multiplexer 334 circuit. The processor 308 receives the digital output 338 of the ADC circuit 336 and calculates the transducer impedance Z based on the measured values of current and voltage. The processor 308 adjusts the ultrasonic electrical drive signal 304 such that it can generate a desired power versus load curve. In accordance with programmed algorithm(s) 310, the processor 308 can step the ultrasonic electrical drive signal 304, e.g., the current or frequency, in any suitable increment or decrement in response to the transducer impedance Z.

Figure 7:
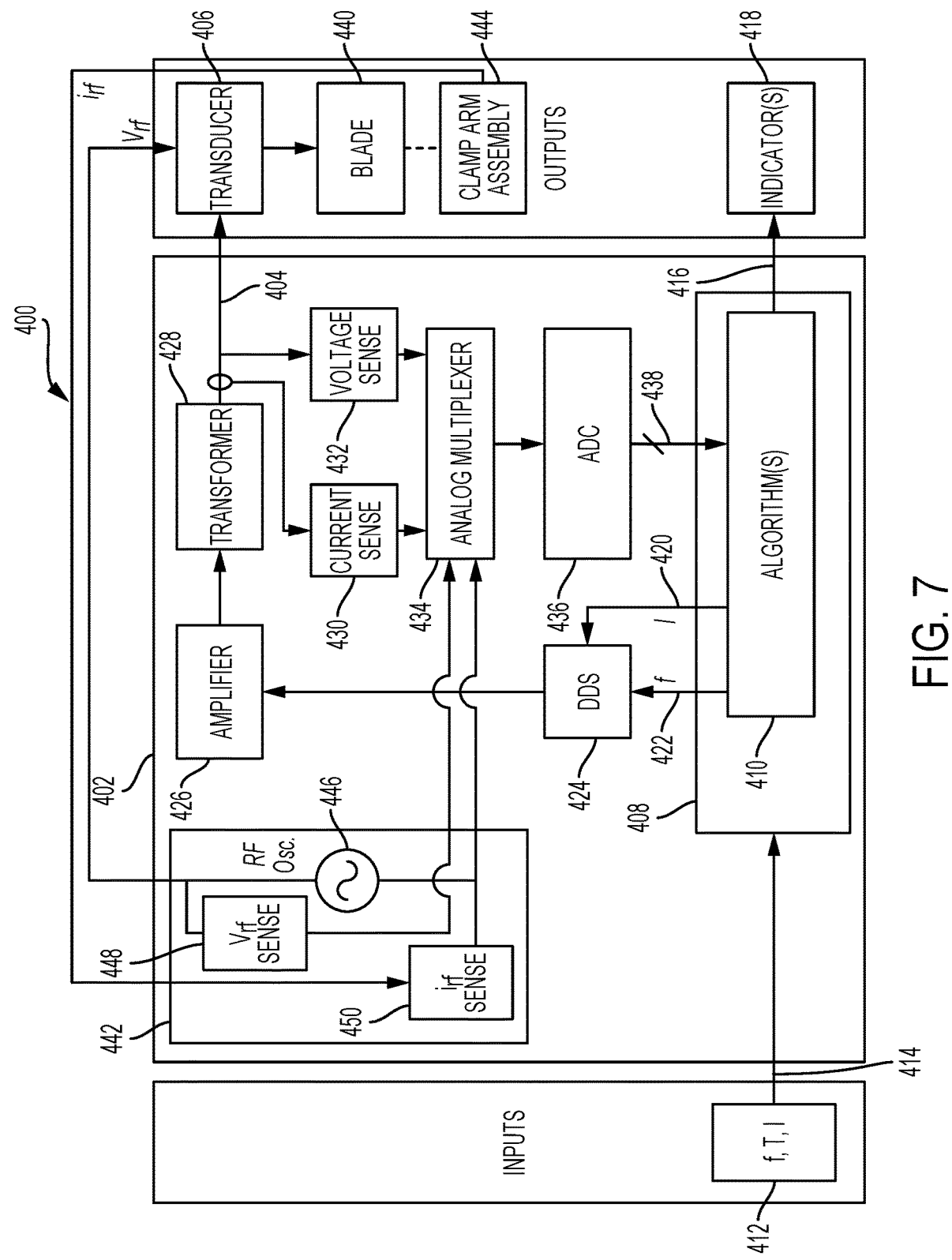
FIG. 7 illustrates one form of a drive system of a generator comprising a tissue impedance module.

FIG. 7 illustrates one aspect of a drive system 402 of the generator 400, which is one form of the generator 100 (FIGS. 1-3). In operation, the user can program the operation of the generator 400 using the input device 412 located on the front panel of the generator 400 console. The input device 412 may comprise any suitable device that generates signals 414 that can be applied to the processor 408 to control the operation of the generator 400. In various forms, the input device 412 includes buttons, switches, thumbwheels, keyboard, keypad, touch screen monitor, pointing device, remote connection to a general purpose or dedicated computer. In other forms, the input device 412 may comprise a suitable user interface. Accordingly, by way of the input device 412, the user can set or program the current (I), voltage (V), frequency (f), and/or period (T) for programming the output of the generator 400. The processor 408 then displays the selected power level by sending a signal on line 416 to an output indicator 418.

The generator 400 comprises a tissue impedance module 442. The drive system 402 is configured to generate electrical drive signal 404 to drive the ultrasonic transducer 406. In one aspect, the tissue impedance module 442 may be configured to measure the impedance Zt of tissue grasped between the blade 440 and the clamp arm assembly 444. The tissue impedance module 442 comprises an RF oscillator 446, an RF voltage sensing circuit 448, and an RF current sensing circuit 450. The RF voltage and RF current sensing circuits 448, 450 respond to the RF voltage Vrf applied to the blade 440 electrode and the RF current Irf flowing through the blade 440 electrode, the tissue, and the conductive portion of the clamp arm assembly 444. The sensed voltage Vrf and current Irf are converted to digital form by the ADC circuit 436 via the analog multiplexer 434. The processor 408 receives the digital output 438 of the ADC circuit 436 and determines the tissue impedance Zt by calculating the ratio of the RF voltage Vrf to current Irf measured by the RF voltage sense circuit 448 and the RF current sense circuit 450. In one aspect, the transection of the inner muscle layer and the tissue may be detected by sensing the tissue impedance Zt. Accordingly, detection of the tissue impedance Zt may be integrated with an automated process for separating the inner muscle layer from the outer adventitia layer prior to transecting the tissue without causing a significant amount of heating, which normally occurs at resonance.

In one form, the RF voltage Vrf applied to the blade 440 electrode and the RF current Irf flowing through the blade 440 electrode, the tissue, and the conductive portion of the clamp arm assembly 451 are suitable for vessel sealing and/or dissecting. Thus, the RF power output of the generator 400 can be selected for non-therapeutic functions such as tissue impedance measurements as well as therapeutic functions such as vessel sealing and/or dissection. It will be appreciated, that in the context of the present disclosure, the ultrasonic and the RF electrosurgical energies can be supplied by the generator either individually or simultaneously.

In various forms, feedback is provided by the output indicator 418 shown in FIGS. 6 and 7. The output indicator 418 is particularly useful in applications where the tissue being manipulated by the end effector is out of the user's field of view and the user cannot see when a change of state occurs in the tissue. The output indicator 418 communicates to the user that a change in tissue state has occurred. As previously discussed, the output indicator 418 may be configured to provide various types of feedback to the user including, without limitation, visual, audible, and/or tactile feedback to indicate to the user (e.g., surgeon, clinician) that the tissue has undergone a change of state or condition of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handle assembly. The change of state of the tissue may be determined based on transducer and tissue impedance measurements as previously described, or based on voltage, current, and frequency measurements.

In one form, the processor 408 may be configured or programmed to generate a digital current signal 420 and a digital frequency signal 422. These digital signals 420, 422 are applied to a digital synthesis circuit such as the DDS circuit 424 (see e.g., FIGS. 13, 14) to adjust the amplitude and the frequency (f) of the electrical drive signal 404 to the transducer 406. The output of the DDS circuit 424 is applied to a power amplifier 426 whose output is applied to a transformer 428. The output of the transformer 428 is the electrical drive signal 404 applied to the ultrasonic transducer 406, which is coupled to a blade by way of a waveguide. The output of the DDS circuit 424 may be stored in one more memory circuits including volatile (RAM) and non-volatile (ROM) memory circuits.

In one form, the generator 400 comprises one or more measurement modules or components that may be configured to monitor measurable characteristics of the ultrasonic instrument 104 (FIGS. 1, 3) or the multifunction electrosurgical/ultrasonic instrument 108 (FIGS. 1-3). In the illustrated form, the processor 408 may be employed to monitor and calculate system characteristics. As shown, the processor 408 measures the impedance Z of the transducer by monitoring the current supplied to the ultrasonic transducer 406 and the voltage applied to the transducer. In one form, a current sense circuit 430 is employed to sense the current flowing through the transducer and a voltage sense circuit 432 is employed to sense the output voltage applied to the ultrasonic transducer 406. These signals may be applied to the ADC circuit 436 via an analog multiplexer 434 circuit or switching circuit arrangement. The analog multiplexer 434 routes the appropriate analog signal to the ADC circuit 436 for conversion. In other forms, multiple ADC circuits 436 may be employed for each measured characteristic instead of the analog multiplexer 434 circuit. The processor 408 receives the digital output 438 of the ADC circuit 436 and calculates the transducer impedance Z based on the measured values of current and voltage. The processor 308 adjusts the electrical drive signal 404 such that it can generate a desired power versus load curve. In accordance with programmed algorithm(s) 410, the processor 408 can step the ultrasonic electrical drive signal 404, e.g., the current or frequency, in any suitable increment or decrement in response to the transducer impedance Z.

With reference to FIGS. 6 and 7, in various forms, the various executable instructions or modules (e.g., algorithms 310, 410) comprising computer readable instructions can be executed by the processor 308, 408 portion of the generator 300, 400. In various forms, the operations described with respect to the algorithms may be implemented as one or more software components, e.g., programs, subroutines, logic; one or more hardware components, e.g., processors, DSPs, PLDs, ASICs, circuits, registers; and/or combinations of software and hardware. In one form, the executable instructions to perform the algorithms may be stored in memory. When executed, the instructions cause the processor 308, 408 to determine a change in tissue state provide feedback to the user by way of the output indicator 318, 418. In accordance with such executable instructions, the processor 308, 408 monitors and evaluates the voltage, current, and/or frequency signal samples available from the generator 300, 400 and according to the evaluation of such signal samples determines whether a change in tissue state has occurred. As further described below, a change in tissue state may be determined based on the type of ultrasonic instrument and the power level that the instrument is energized at.

In response to the feedback, the operational mode of the surgical instruments 104, 106, 108 (FIGS. 1-3) may be controlled by the user or may be automatically or semi-automatically controlled.

Figure 8:
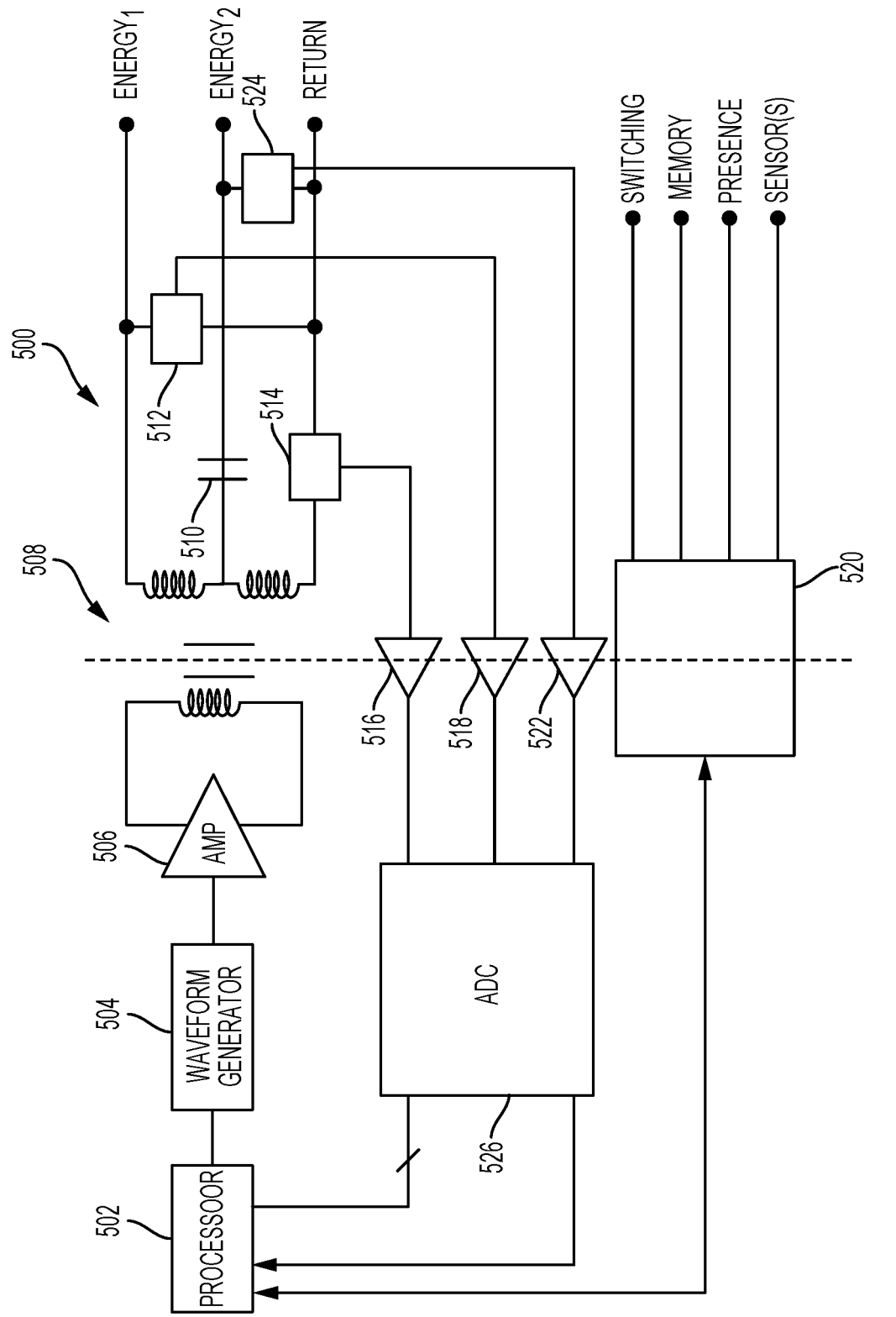
FIG. 8 illustrates an example of a combined RF and ultrasonic energy generator for delivering energy to a surgical instrument.

FIG. 8 illustrates an example of a generator 500, which is one form of the generator 100 (FIGS. 1-3). The generator 500 is configured to deliver multiple energy modalities to a surgical instrument. The generator 500 includes functionalities of the generators 200, 300, 400 shown in FIGS. 5-7. The generator 500 provides RF and ultrasonic signals for delivering energy to a surgical instrument. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port and these signals can be delivered separately or simultaneously to the end effector to treat tissue. The generator 500 comprises a processor 502 coupled to a waveform generator 504. The processor 502 and waveform generator 504 are configured to generate a variety of signal waveforms based on information stored in a memory coupled to the processor 502, not shown for clarity of disclosure. The digital information associated with a waveform is provided to the waveform generator 504 which includes one or more DAC circuits to convert the digital input into an analog output. The analog output is fed to an amplifier 1106 for signal conditioning and amplification. The conditioned and amplified output of the amplifier 506 is coupled to a power transformer 508. The signals are coupled across the power transformer 508 to the secondary side, which is in the patient isolation side. A first signal of a first energy modality is provided to the surgical instrument between the terminals labeled ENERGY1 and RETURN. A second signal of a second energy modality is coupled across a capacitor 510 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 512 is coupled across the terminals labeled ENERGY1 and the RETURN path to measure the output voltage therebetween. A second voltage sensing circuit 524 is coupled across the terminals labeled ENERGY2 and the RETURN path to measure the output voltage therebetween. A current sensing circuit 514 is disposed in series with the RETURN leg of the secondary side of the power transformer 508 as shown to measure the output current for either energy modality. If different return paths are provided for each energy modality, then a separate current sensing circuit should be provided in each return leg. The outputs of the first and second voltage sensing circuits 512, 524 are provided to respective isolation transformers 516, 522 and the output of the current sensing circuit 514 is provided to another isolation transformer 518. The outputs of the isolation transformers 516, 518, 522 in the on the primary side of the power transformer 508 (non-patient-isolated side) are provided to a one or more ADC circuit 526. The digitized output of the ADC circuit 526 is provided to the processor 502 for further processing and computation. The output voltages and output current feedback information can be employed to adjust the output voltage and current provided to the surgical instrument and to compute output impedance, among other parameters. Input/output communications between the processor 502 and patient isolated circuits is provided through an interface circuit 520. Sensors also may be in electrical communication with the processor 502 by way of the interface circuit 520.

In one aspect, the impedance may be determined by the processor 502 by dividing the output of either the first voltage sensing circuit 512 coupled across the terminals labeled ENERGY1/RETURN or the second voltage sensing circuit 524 coupled across the terminals labeled ENERGY2/RETURN by the output of the current sensing circuit 514 disposed in series with the RETURN leg of the secondary side of the power transformer 508. The outputs of the first and second voltage sensing circuits 512, 524 are provided to separate isolations transformers 516, 522 and the output of the current sensing circuit 514 is provided to another isolation transformer 516. The digitized voltage and current sensing measurements from the ADC circuit 526 are provided the processor 502 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 8 shows a single return path RETURN may be provided for two or more energy modalities, in other aspects multiple return paths RETURNn may be provided for each energy modality ENERGYn. Thus, as described herein, the ultrasonic transducer impedance may be measured by dividing the output of the first voltage sensing circuit 512 by the current sensing circuit 514 and the tissue impedance may be measured by dividing the output of the second voltage sensing circuit 524 by the current sensing circuit 514.

As shown in FIG. 8, the generator 500 comprising at least one output port can include a power transformer 508 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 500 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 500 can be steered, switched, or filtered to provide the frequency to the end effector of the surgical instrument. The connection of an ultrasonic transducer to the generator 500 output would be preferably located between the output labeled ENERGY1 and RETURN as shown in FIG. 8. An In one example, a connection of RF bipolar electrodes to the generator 500 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

In other aspects, the generators 100, 200, 300, 400, 500 described in connection with FIGS. 1-3 and 5-8, the ultrasonic drive circuit 114, and/or electrosurgery/RF drive circuit 116 as described in connection with FIG. 3 may be formed integrally with any one of the surgical instruments 104, 106, 108 described in connection with FIGS. 1 and 2. Accordingly, any of the processors, digital signal processors, circuits, controllers, logic devices, ADCs, DACs, amplifiers, converters, transformers, signal conditioners, data interface circuits, current and voltage sensing circuits, direct digital synthesis circuits, multiplexer (analog or digital), waveform generators, RF generators, memory, and the like, described in connection with any one of the generators 100, 200, 300, 400, 500 can be located within the surgical instruments 104, 106, 108 or may be located remotely from the surgical instruments 104, 106, 108 and coupled to the surgical instruments via wired and/or wireless electrical connections.

Figure 9:
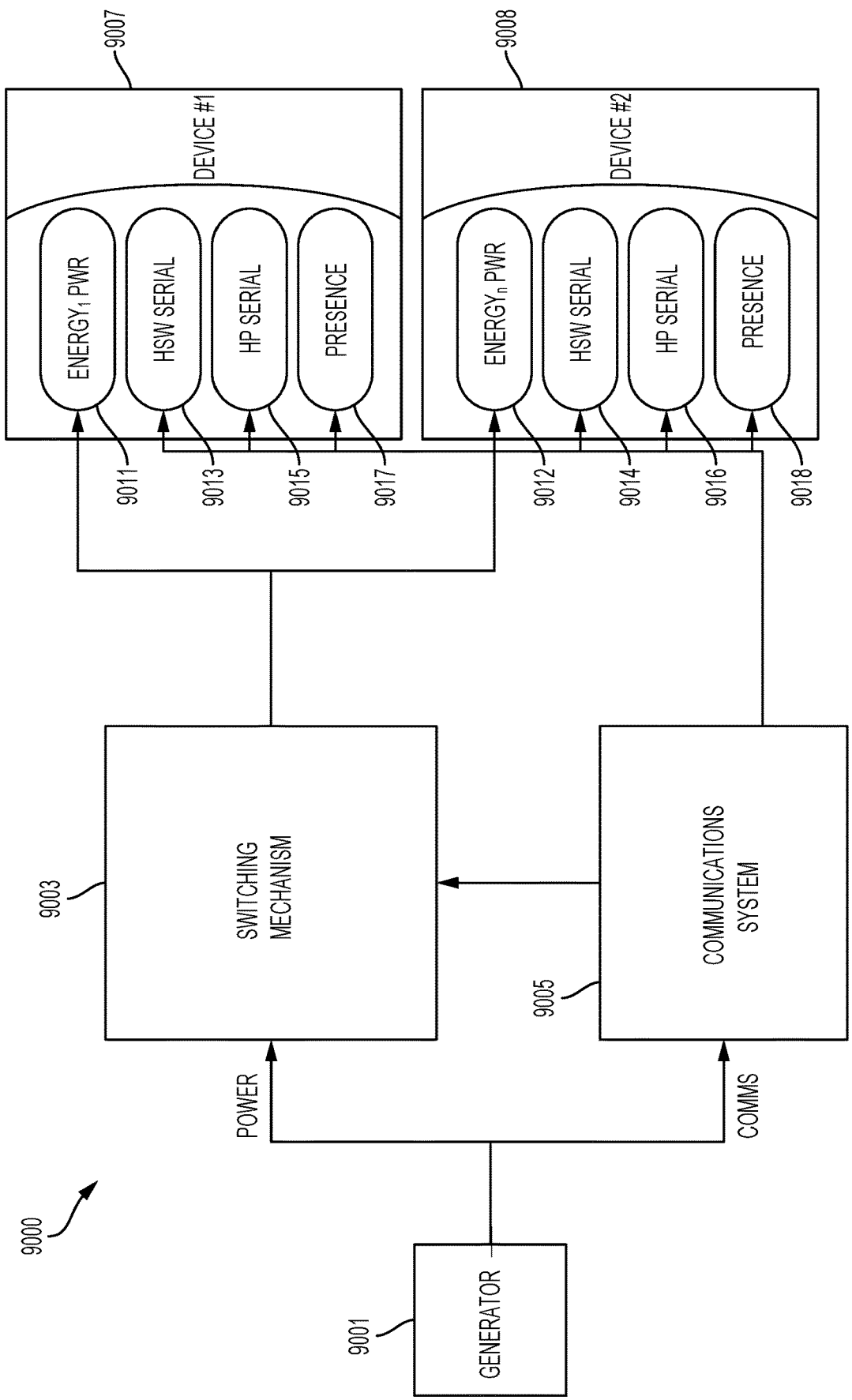
FIG. 9 is a diagram of a system for delivering combined RF and ultrasonic energy to a plurality of surgical instruments.

FIG. 9 shows a diagram of an electrosurgical system 9000 that allows for two ports on a generator 9001 and accounts for electrical isolation between two surgical instruments 9007, 9008. A scheme is provided for electrical isolation between the two surgical instruments 9007, 9008 as they are located on the same patient isolation circuit. According to the configuration shown in FIG. 9, unintended electrical power feedback is prevented through the electrosurgical system 9000. In various aspects, power field-effect-transistors (FETs) or relays are used to electrically isolate all power lines for each instrument 9007, 9008. According to one aspect, the power FETs or relays are controlled by a 1-wire communication protocol.

As shown in FIG. 9, a generator 9001, which is one form of the generator 100 (FIGS. 1-3), is coupled to a power switching mechanism 9003 and a communications system 9005. In one aspect, the power switching mechanism 9003 comprises power FETs, such as power metal-oxide semiconductor FETs (MOSFETs), and/or relays, such as electromechanical relays. In one aspect, the communications system 9005 comprises components for D1 emulation, FPGA expansion, and time slicing functionalities. The power switching mechanism 9003 is coupled to the communications system 9005. Each of the power switching mechanism 9003 and the communications system 9005 are coupled to surgical instruments 9007, 9009 (labeled device 1 and device 2). Each of surgical instruments 9007, 9009 comprise components for a combined RF and Ultrasonic energy input 9011, hand switch (HSW) 1-wire serial protocol interface 9013, HP 1-wire serial protocol interface 9015, and a presence interface 9017. The power switching mechanism 9003 is coupled to the RF and Ultrasonic energy input 9011 for each of surgical instruments 9007, 9008. The communications system 9005 is coupled to the HSW 1-wire serial protocol interface 9013, 9014, the HP 1-wire serial protocol interface 9015, 9016, and presence interface 9017, 9018 for each of surgical instruments 9007, 9008. While two surgical instruments are shown in FIG. 9, there may be more than two devices according to various aspects.

Figure 10:
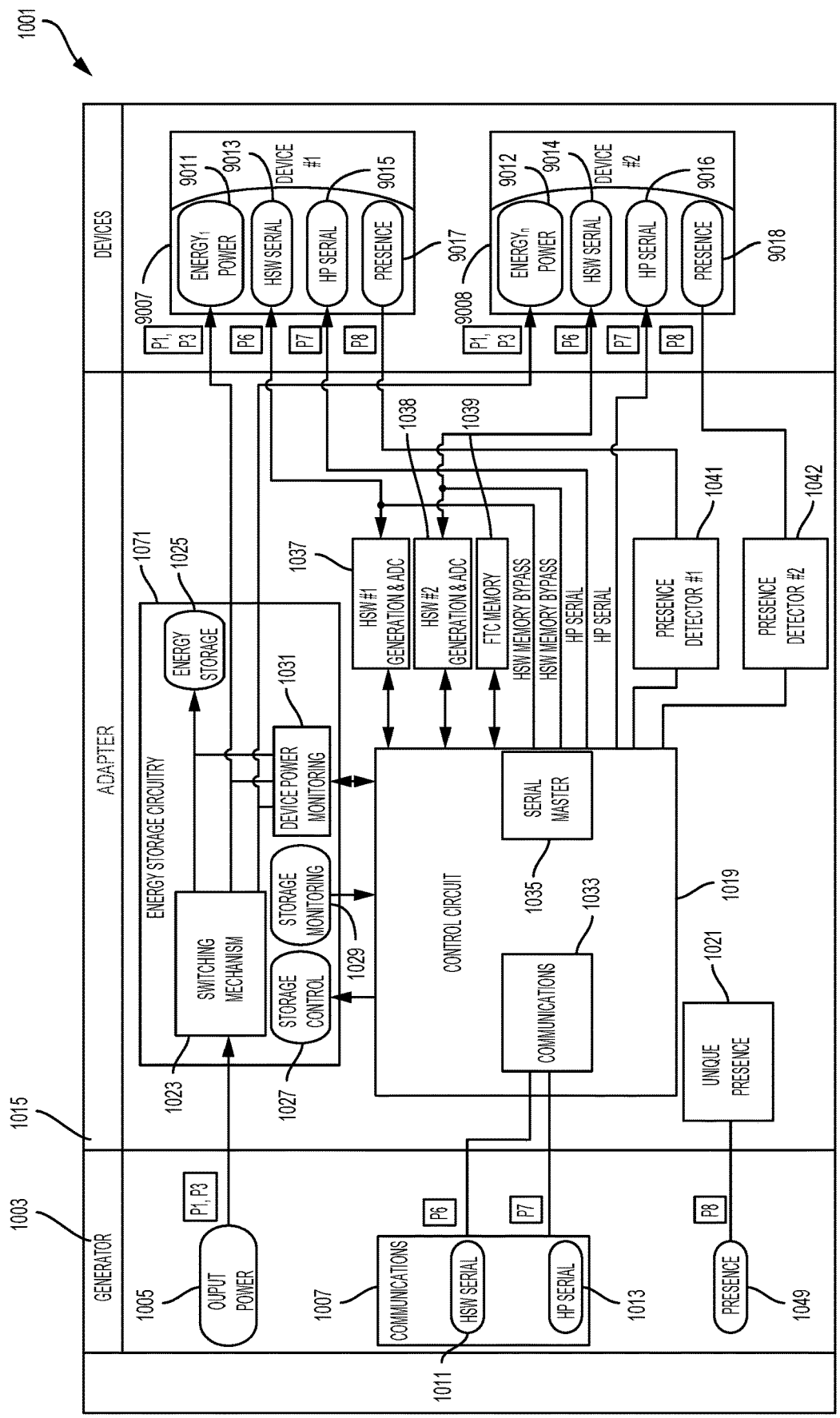
FIG. 10 illustrates a communications architecture of a system for delivering combined RF and ultrasonic energy to a plurality of surgical instruments.
Figure 11:
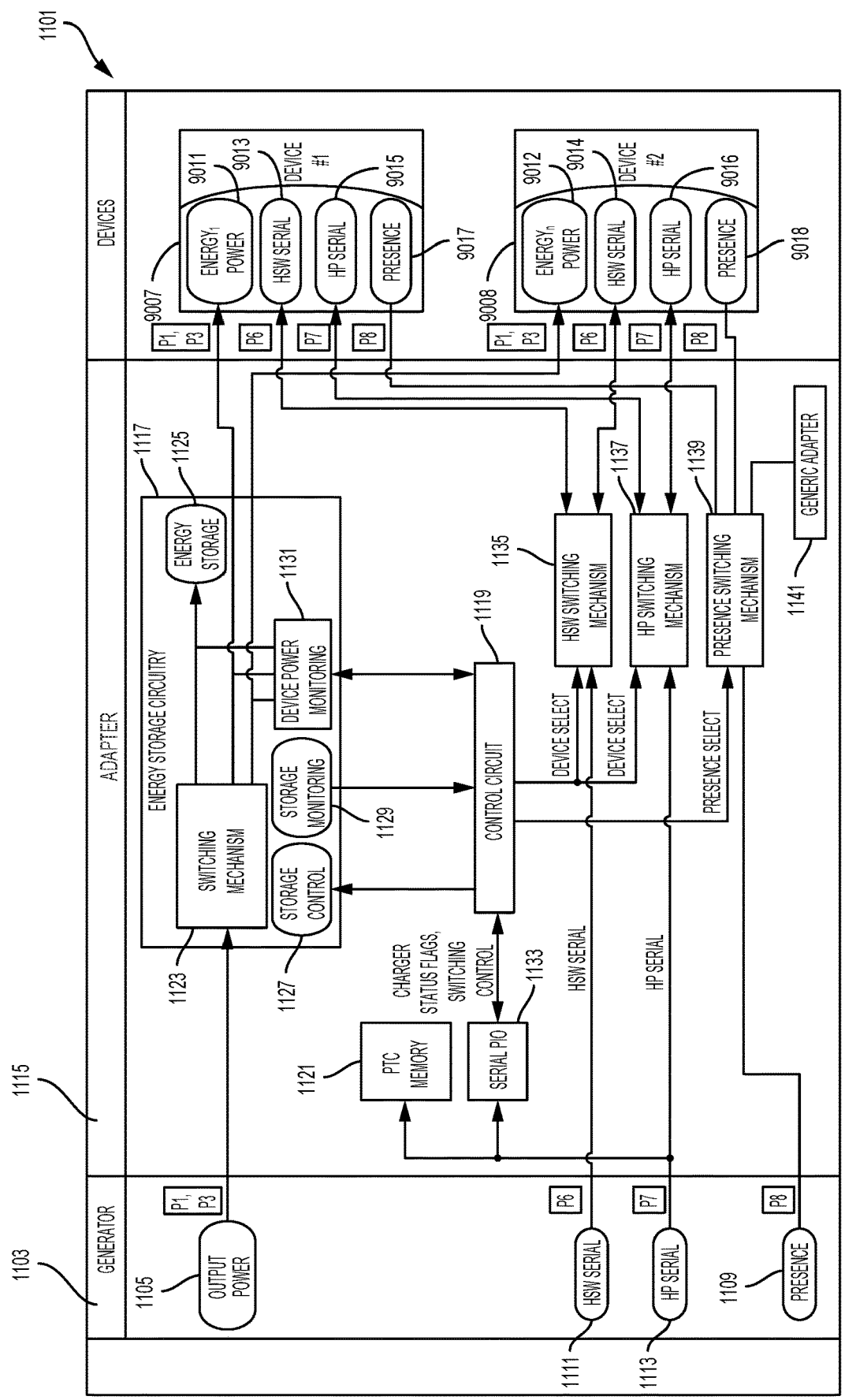
FIG. 11 illustrates a communications architecture of a system for delivering combined RF and ultrasonic energy to a plurality of surgical instruments.
Figure 12:
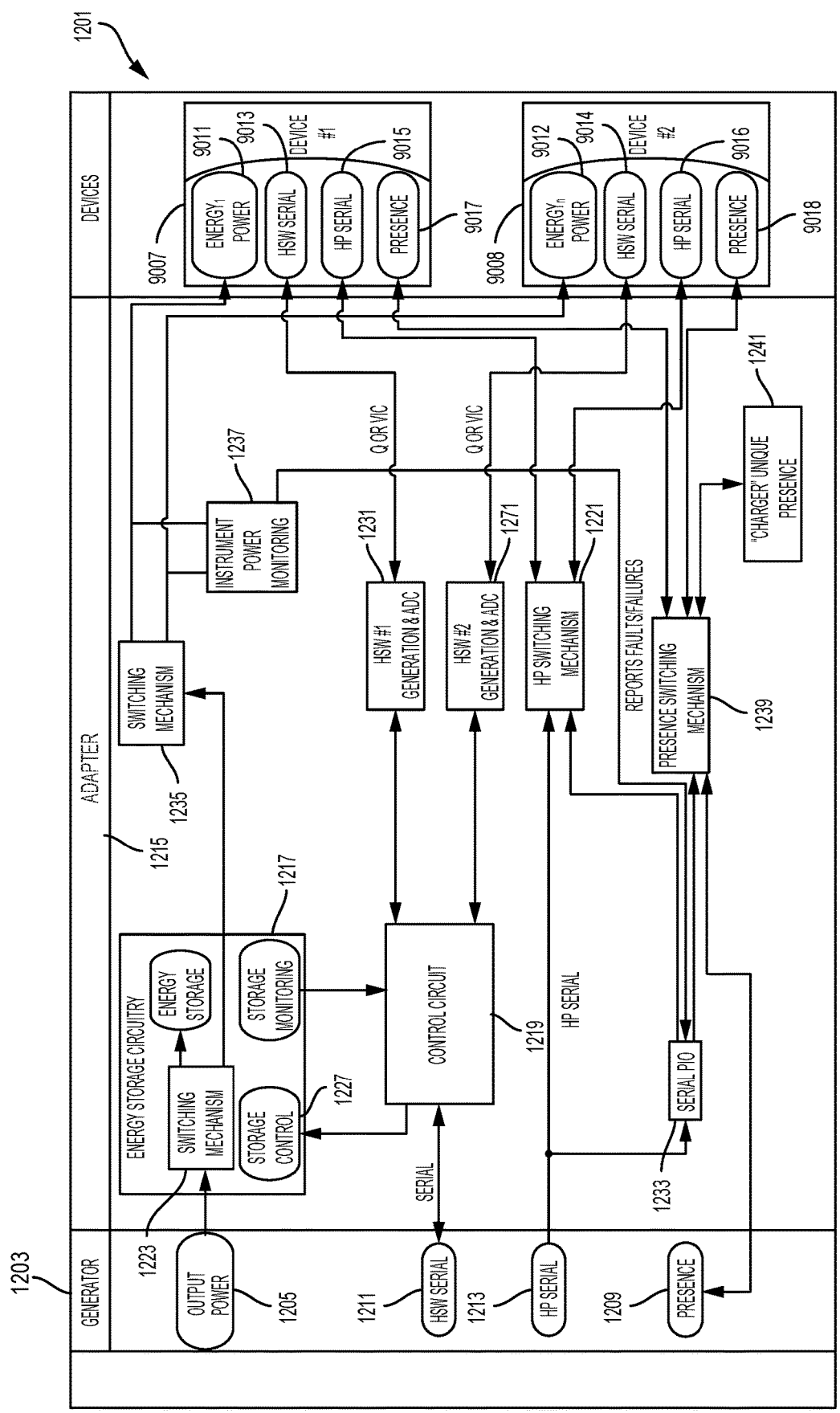
FIG. 12 illustrates a communications architecture of a system for delivering combined RF and ultrasonic energy to a plurality of surgical instruments.

FIGS. 10-12 illustrate aspects of an interface with a generator to support two instruments simultaneously that allows the instruments to quickly switch between active/inactive by a user in a sterile field. FIGS. 10-12 describe multiple communication schemes which would allow for a super cap/battery charger and dual surgical instruments. The aspects of FIGS. 10-12 allow for communications to two surgical instruments in the surgical field from a generator with at least one communications port and allow for an operator in sterile field to switch between devices, for example, without modifying the surgical instruments.

FIG. 10 is a diagram of a communications architecture of system 1001 comprising a generator 1003, which is one form of the generator 100 (FIGS. 1-3), and surgical instruments 9007, 9008, which are shown in FIG. 9. According to FIG. 10, the generator 9001 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. The generator 9001 comprises a combined energy modalities power output 1005, a communications interface 1007, and a presence interface 1049. According to the aspect of FIG. 10, the communications interface 1007 comprises an HSW serial interface 1011 and an HP serial interface 1013. The serial interfaces 1011, 1013 may comprise inter-integrated circuit ($I^2C$), half duplex serial peripheral interface (SPI), and/or Universal Asynchronous Receiver Transmitter (UART) components and/or functionalities. The generator 1003 provides the combined energy modalities power output 1005 to an adapter 1015, for example, a pass-through charger (PTC). The adapter 1015 comprises energy storage circuit 1071, control circuit 1019, a unique presence element 1021, and associated circuit discussed below. In one aspect, the presence element 1021 is a resistor. In another aspect, the presence element 1021 may be a bar code, Quick Response (QR) code, or similar code, or a value stored in memory such as, for example, a value stored in NVM. The presence element 1021 may be unique to the adapter 1015 so that, in the event that another adapter that did not use the same wire interfaces could not be used with the unique presence element 1021. In one aspect, the unique presence element 1021 is a resistor. The energy storage circuit 1071 comprises a switching mechanism 1023, energy storage device 1025, storage control 1027, storage monitoring component 1029, and a device power monitoring component 1031. The control circuit 1019 may comprise a processor, FPGA, PLD, complex programmable logic device (CPLD), microcontroller, DSP, and/or ASIC, for example. According to the aspect shown in FIG. 10, an FPGA or microcontroller would act as an extension of an existing, similar computing hardware and allows for information to be relayed from on entity to another entity.

The switching mechanism 1023 is configured to receive the combined energy modalities power output 1005 from the generator 1003 and it may be provided to the energy storage device 1025, surgical instrument 9007, and/or surgical instrument 9008. The device power monitoring component 1031 is coupled to the channels for the energy storage device 1025, surgical instrument 9007, surgical instrument 9008, and may monitor where power is flowing. The control circuit 1019 comprises communication interface 1033 coupled to the HSW serial interface 1011 and an HP serial interface 1013 of the generator 1003. The control circuit 1019 is also coupled to the storage control 1027, storage monitoring component 1029, and device power monitoring component 1031 of the energy storage circuit 1071.

The control circuit 1019 further comprises a serial master interface 1035 that is coupled to HSW #1 circuit 1037 and HSW #2 circuit 1038, includes generation and ADC circuit, a form of memory (non volatile or flash) 1039, along with a method for detecting the presence of an attached instrument (Presence) #1 circuit 1041 and Presence #2 circuit 1042, which includes a voltage or current source and ADC circuit. The serial master interface 1035 also includes HSW NVM bypass channels, which couple the serial master interface 1035 to the outputs of the HSW #1 circuit 1037 and the HSW #2 circuit 1038, respectively. The HSW #1 circuit 1037 and HSW #2 circuit 1038 are coupled to the HSW 1-wire serial protocol interfaces 9013, 9014 of the surgical instruments 9007, 9008, respectively. The serial master interface 1035 further includes HP serial channels that are coupled to the HP 1-wire serial protocol interfaces 9015, 9016 of the surgical instruments 9007, 9008, respectively.

Further, Presence #1 and Presence #2 circuits 1041, 1042 are coupled to the presence interfaces 9017, 9018 of the surgical instruments 9007, 9008, respectively.

The system 1001 allows the control circuit 1019, such as an FPGA, to communicate with more surgical instruments using adapter 1015, which acts as an expansion adapter device. According to various aspects, the adapter 1015 expands the Input/Output (I/O) capability of the generator 1003 control. The adapter 1015 may function as an extension of the central processing unit that allows commands to be transmitted over a bus between the adapter 1015 and the generator 1003 and unpacks the commands and use them to bit-bang over interfaces or to control connected analog circuit. The adapter 1015 also allows for reading in ADC values from connected surgical instruments 9007, 9008 and relay this information to the generator control and the generator control would then control the two surgical instruments 9007, 9008. According to various aspects, the generator 1003 may control the surgical instruments 9007, 9008 as two separate state machines and may store the data.

Existing interfaces (the HSW serial interface 1011 and the HP serial interface 1013 lines from generator 1003) may be used in a two-wire communication protocol that enables the generator 1003 control to communicate with multiple surgical instruments connected to a dual port interface, similar to the topology of a universal serial bus (USB) hub.

This allows interfacing with two separate surgical instruments simultaneously. The system 1001 may be able to generate and read hand switch waveforms and be able to handle incoming HP serial buses. It would also monitor two separate presence elements in the surgical instruments 9007, 9008. In one aspect, the system 1001 may include a unique presence element and may have its own NVM.

Further, according to various aspects, the control circuit 1019 may be controlled by the generator 1003. The communication between the adapter 1015 and connected surgical instruments 9007, 9008 may be relayed to generator control. The generator 1003 would control the waveform generation circuit connected to the adapter 1015 to simultaneously generate HSW signals for surgical instruments 9007, 9008.

The system 1001 may allow surgical instrument activity that can be simultaneously detected/monitored for two surgical instruments, even during activation. If upgradeable, the adapter 1015 would be capable of handling new surgical instrument communications protocols. Further, fast switching between surgical instruments may be accomplished.

FIG. 11 illustrates a communication architecture of system 1101 of a generator 1103, which is one form of the generator 100 (FIGS. 1-3), and surgical instruments 9007, 9008 shown in FIG. 9. According to FIG. 11, the generator 1103 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. As shown in FIG. 11, the generator 1103 comprises a combined energy modalities power output 1105, a HSW serial interface 1111, a HP serial interface 1113, and a presence interface 1109. The generator 1103 provides the combined energy modalities power output 1105 to an adapter 1115. According to the aspect shown in FIG. 11, communications between the adapter 1115 and the generator 1103 may be done solely through serial interfaces, such as the HSW serial and HP serial interfaces 1111, 1113. The generator 1103 may use these HSW and HP serial interfaces 1111, 1113 to control which instrument the generator 1103 is communicating with. Further, switching between instruments could occur between HSW frames or at a much slower rate.

The adapter 1115 comprises an energy storage circuit 1117, control circuit 1119, an adapter memory 1121 (e.g., a NVM such as an EEPROM), a serial programmable input/output (PIO) integrated circuit 1133, a HSW switching mechanism 1135, a HP switching mechanism 1137, a presence switching mechanism 1139, and a generic adapter 1141. In one aspect, the serial PIO integrated circuit 1133 may be an addressable switch. The energy storage circuit 1117 comprises a switching mechanism 1123, energy storage device 1125, storage control component 1127, storage monitoring component 1129, and a device power monitoring component 1131. The control circuit 1119 may comprise a processor, FPGA, CPLD, PLD, microcontroller, DSP, and/or an ASIC, for example. According to the aspect of FIG. 11, an FPGA or microcontroller may have limited functionality and may solely comprise functionality for monitoring and communicating energy storage.

The switching mechanism 1123 is configured to receive the combined energy modalities energy power output 1105 from the generator 1103 and it may be provided to the energy storage device 1125, surgical instrument 9007, and/or surgical instrument 9008. The device power monitoring component 1131 is coupled to the channels for the energy storage device 1125, surgical instrument 9007, surgical instrument 9008, and may monitor where power is flowing.

The control circuit 1119 is coupled to the serial PIO integrated circuit 1133 and the serial PIO integrated circuit 1133 is coupled to the HP serial interface 1113 of the generator 1103. The control circuit 1119 may receive information regarding charger status flags and switching controls from the serial PIO integrated circuit 1133. Further, the control circuit 1119 is coupled to the HSW switching mechanism 1135, the HP switching mechanism 1137, and the presence switching mechanism 1139. According to the aspect of FIG. 11, the control circuit 1119 may be coupled to the HSW switching mechanism 1135 and the HP switching mechanism 1137 for device selection and the control circuit 1119 may be coupled to the presence switching Mechanism 1139 for presence selection.

The HSW switching mechanism 1135, the HP switching mechanism 1137, and the presence switching mechanism 1139 are coupled to the HSW serial interface 1111, the HP serial interface 1113, and the presence interface 1109 of generator 1103, respectively. Further, the HSW switching mechanism 1135, the HP switching mechanism 1137, and the presence switching mechanism 1139 are coupled to the HSW 1-wire serial protocol interfaces 9013, 9014, the HP 1-wire serial protocol interfaces 9015, 9016, and the presence interfaces 9017, 9018 of the surgical instruments 9007, 9008, respectively. Further, the presence switching mechanism 1139 is coupled to the generic adapter 1141.

The generator 1103 switches between monitoring the surgical instruments 9007, 9008. According to various aspects, this switching may require the generator 1103 control to keep track of surgical instruments 9007, 9008 and run two separate state machines. The control circuit 1119 will need to remember which surgical instruments are connected, so that it can output an appropriate waveform to the ports where appropriate. The generator 1103 may generate/monitor hand switch signals, as well as communicating with serial NVM devices, such as the adapter memory 1121. The generator 1103 may maintain constant communication with the activating surgical instrument for the duration of the activation.

System 1101 also allows for a generic adapter presence element. When first plugged in or powered on, the adapter 1115 would present this adapter resistance to the generator 1103. The generator 1103 may then relay commands to the adapter 1115 to switch between the different presence elements corresponding to the different surgical instruments 9007, 9008 connected to it. Accordingly, the generator 1103 is able to use its existing presence resistance circuit. The NVM adapter memory 1121 exists on the adapter 1115 for additional identification of the adapter and to provide a level of security. In addition, the adapter 1115 has a serial I/O device, i.e., serial PIO integrated circuit 1133. The serial PIO integrated circuit 1133 provides a communication link between the generator 1103 and the adapter 1115.

It may be possible to communicate over the HP serial bus using serial communications to HP NVMs and UART style communication to the control circuit 1119. According to one aspect, if SLOW serial communication is used (i.e. not overdrive) and a high speed serial protocol is used, system 1101 may need to ensure that the communications protocol does not generate a signal that looked like a serial reset pulse. This would allow better generator 1103 to adapter 1115 communications and faster switching times between surgical instruments 9007, 9008.

The system 1101 uses generator communications protocol and analog circuit and allows the generator to accomplish decision making. It is a simple and efficient solution that uses a small number of circuit devices.

FIG. 12 illustrates a communications architecture of system 1201 of a generator 1203, which is one form of the generator 100 (FIGS. 1-3), and surgical instruments 9007, 9008 shown in FIG. 9. According to FIG. 12, the generator 1203 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. As shown in FIG. 12, the generator 1203 comprises a combined energy modalities power output 1205, a HSW serial interface 1211, an HP serial interface 1213, and a presence interface 1209. In one aspect, the HP serial interface 1213 allows for communication with the HP lines of the surgical instruments 9007, 9008 and also allows for control of the adapter 1215. The generator 1203 provides the combined energy modalities power output 1205 to an adapter 1215. The adapter 1215 comprises energy storage circuit 1217, control circuit 1219, a serial PIO integrated circuit 1233, HSW #1 circuit 1231, HSW #2 circuit 1271, HP switching mechanism 1221, presence switching mechanism 1239, switching mechanism 1235, instrument power monitoring 1237, and unique presence 1241. As shown in FIG. 12, the HSW #1 circuit 1231 and the HSW #2 circuit 1271 may comprise generation and ADC circuits. In one aspect, HSW #1 circuit 1231 and/or HSW #2 circuit 1271 comprise generation circuit with the ability to generate HSW waveforms.

The control circuit 1219 is coupled to the HSW serial interface 1211 of the generator 1203 while the serial PIO integrated circuit 1233 is coupled to the HP serial interface 1213 as is the HP switching mechanism 1221. Further, the control circuit 1119 is coupled to the HSW #1 circuit 1231 and the HSW #2 circuit 1271. The control circuit 1119 may comprise a processor, FPGA, CPLD, PLD, microcontroller, and/or ASIC, for example. In the example shown in FIG. 12, the control circuit 1219 modulates two devices into at least one digital waveform, which enable the generator 1203 to perform the button monitoring and decision making. The control circuit 1219 also may allow for communication to two independent surgical instruments could receive either waveform. The serial PIO integrated circuit 1233 is further coupled to the HP switching mechanism 1221, the instrument power monitoring 1237, and the presence switching mechanism 1239. The instrument power monitoring 1237 and the serial PIO integrated circuit 1233 may communicate results and failures to the generator 1203.

The switching mechanism 1223 is configured to receive the combined RF/ultrasonic energy modalities output power 1205 from the generator 1203 and it may be provided to the energy storage circuit 1225 or the switching mechanism 1235. The control circuit 1219 is also coupled to the storage control 1227 and energy storage monitoring 1229 of the energy storage circuit 1217. The switching mechanism 1235 may provide the power output received from the switching mechanism 1223 to surgical instrument 9007, and/or surgical instrument 9008. The instrument power monitoring 1237 is coupled to the channels for the power output to the surgical instrument 9007 and surgical instrument 9008. The instrument power monitoring 1237 also may ensure that the switching mechanism 1235 is delivering power to correct location.

The HSW #1 circuit 1231 and the HSW #2 circuit 1271 are coupled to the HSW 1-wire serial protocol interfaces 9013, 9014 of the surgical instruments 9007, 9008, respectively. The HP switching mechanism 1221 is coupled to the HP serial interface 1213 of the generator 1203 and to the HP 1-wire serial protocol interfaces 9015, 9016 of the surgical instruments 9007, 9008, respectively. Further, the presence switching mechanism 1239 is coupled to the presence interface 1209 of the generator 1203 and to the presence interfaces 9017, 9018 of the surgical instruments 9007, 9008, respectively. Further, Presence Switching mechanism is coupled to the unique presence 1241. In one aspect, different instrument presence elements may be switched on an on-demand basis using serial I/O or an adapter micro protocol.

A first communications protocol will be used to communicate to the control circuit 1219 on the adapter 1215. The generator 1203 also may have the ability to monitor surgical instruments 9007, 9008 at once. The adapter 1215 may comprise circuit to provide HSW signal generation (e.g., in HSW #1 circuit 1231 and HSW #2 circuit 1271) along with ADC circuits to interpret this data. The adapter 1215 may modulate two surgical instrument signals into at least a first waveform and may have the ability to read in the first and second waveforms. In various aspects, the second waveforms may be interpreted and translated into the format of the first waveforms. Further, the first protocol has the ability to send 12 bits at 615 bits/sec.

The control circuit 1219 may take the HSW data from surgical instruments 9007, 9008 and modulate it into a first protocol. There are a few ways of doing this, but it may mean that surgical instruments 9007, 9008 may comprise a first protocol functionality. The system 1201 could communicate 4-6 buttons from the surgical instrument 9007 and 4-6 buttons from the surgical instrument 9008 in the first protocol frame. Alternatively, the system 1201 could use some form of addressing to access the surgical instruments 9007, 9008. The control circuit 1219 may have the ability to address separate devices by having the generator 1203 send the control circuit 1219 different addresses split into two different address spaces, one for surgical instrument 9007 and one for surgical instrument 9008.

The HP communications may involve some form of switch that could either be controlled via a serial I/O device or through the control circuit 1219 via a first protocol style communication interface from the generator 1203. In one aspect, energy storage monitoring 1229 and switching between surgical instruments 9007, 9008 and charging states could be handled in this manner as well. Certain first protocol addresses could be assigned to the data from the energy storage circuit 1225 and to the surgical instruments 9007, 9008 themselves. Presence elements could also be switched in with this format. Further, in one aspect, the control circuit 1219 may translate frames into a separate format, which may mean that the control circuit 1219 might need to make some decisions on whether button presses on surgical instruments 9007, 9008 are valid or not. The system 1201 would, however, allow the generator 1203 to fully monitor the surgical instruments 9007, 9008 at the same time time-slicing or handling a new communications protocol on the HSW serial interface 1211 of the generator 1203. The system 1201 uses generator communications to simultaneously detect the activity of two surgical instruments, even during activation.

The surgical instruments described herein may be configured to deliver energy from any of the generators 100, 200, 300, 400, 500, 9001, 1003, 1103, 1203 discussed herein. The energy may be dynamically changed based on the type of tissue being treated by an end effector of a surgical instrument and various characteristics of the tissue. For conciseness and clarity of disclosure any of the generators 100, 200, 300, 400, 500, 9001, 1003, 1103, 1203 described hereinabove will be described hereinbelow as generator 100. It will be appreciated that in this context the generator 100 may comprise functional circuits and algorithms described in connection with the generators 200, 300, 400, 500, 9001, 1003, 1103, 1203, taken alone or in combination, as may be appropriate without departing from the scope of the present disclosure. Accordingly, the reader is directed to the description of the functional blocks of the generators 200, 300, 400, 500, 9001, 1003, 1103, 1203, in FIGS. 1-3 and 5-12 for additional details that may be necessary to understand and practice the logic flow diagrams described hereinbelow in connection with the generator 100.

In one aspect, the generator 100 is coupled to the combination RF electrosurgical/ultrasonic instrument 108 shown and described in connection with FIG. 2. The generator 100 may include an algorithm for controlling the power output of the generator 100 delivered to the end effector 125 of the surgical instrument 108. The power output may be varied based on feedback that represents the tissue type located clamp arm 146 and the ultrasonic blade 149 of the end effector 125. Accordingly, the energy profile of the generator 100 may be dynamically altered during the procedure based on the type of tissue being effected by the end effector 125 of the surgical instrument 108. Various algorithms for determining tissue type are described in U.S. patent application Ser. No. 15/177,430, titled SURGICAL INSTRUMENT WITH USER ADAPTABLE TECHNIQUES, filed on Jun. 9, 2016, the contents of which are incorporated herein by reference in their entirety. The generator 100 is configurable for use with different surgical instruments of different types including, for example, the multifunction surgical instrument 108 that integrates electrosurgical RF and ultrasonic energies delivered simultaneously from the generator 100.

According to the present disclosure, the generator 100 may be configured to output an analog output signal usually in the form of a sinusoid at some predetermined frequency or wavelength. The output signal may be characterized by a variety of different types, frequencies, and shapes of electrical signal waveforms suitable for effecting a desired therapy to the tissue. Electrical signal waveforms are basically visual representations of the variation of voltage or current along the vertical axis over time along the horizontal axis represent the shape of the waveform as shown in FIGS. 13-17, for example. The generator 100 includes circuitry and algorithms configured to generate many different types of electrical signal waveforms. In one aspect, the generator 100 is configured to generate electrical signal waveforms using digital signal processing techniques. In one aspect, the generator 100 comprises a memory, DDS circuit (FIGS. 13, 14), a DAC circuit, and a power amplifier configured as discussed hereinbelow to generate a variety of continuous output signals in a variety of electrical waveforms selected based on the tissue type or other feedback information.

Figure 13:
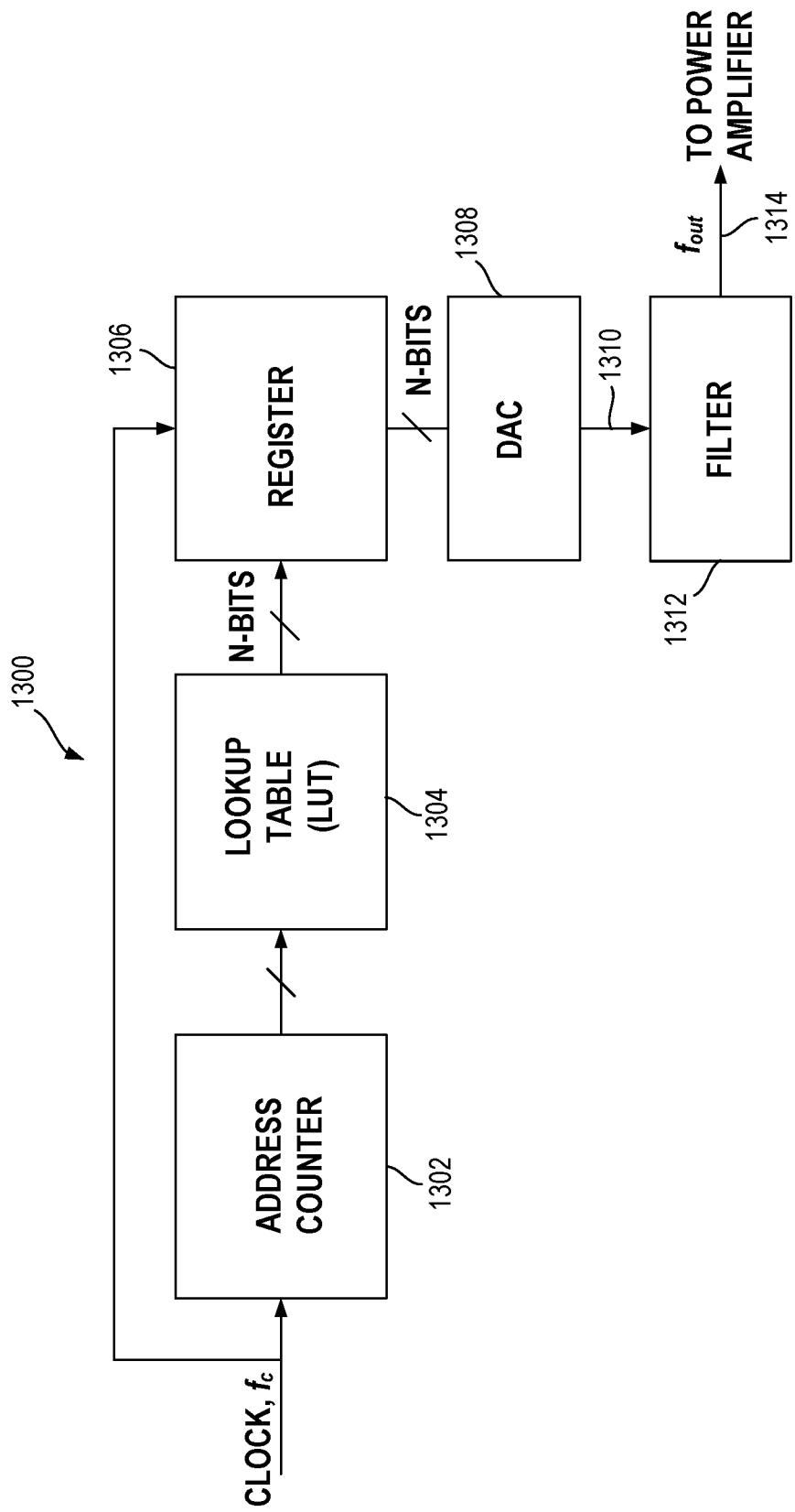
FIG. 13 is a diagram of one form of a direct digital synthesis circuit.

In one aspect, the generator 100 is configured to generate the electrical signal waveform digitally such that the desired using a predetermined number of phase points stored in a lookup table to digitize the wave shape. The phase points may be stored in a table defined in a memory, a FPGA, or any suitable non-volatile memory. FIG. 13 depicts one aspect of a fundamental architecture for a digital synthesis circuit such as a direct digital synthesis (DDS) circuit 1300 configured to generate a plurality of wave shapes for the electrical signal waveform. The generator 100 software and digital controls may command the FPGA to scan the addresses in the lookup table 1304 which in turn provides varying digital input values to a DAC circuit 1308 that feeds a power amplifier. The addresses may be scanned according to a frequency of interest. Using such a lookup table 1304 enables generating various types of wave shapes that can be fed into tissue or into a transducer, an RF electrode, multiple transducers simultaneously, multiple RF electrodes simultaneously, or a combination of RF and ultrasonic instruments. Furthermore, multiple wave shape lookup tables 1304 can be created, stored, and applied to tissue from a single generator 100.

The waveform signal may be configured to control at least one of an output current, an output voltage, or an output power of an ultrasonic transducer and/or an RF electrode, or multiples thereof (e.g. two or more ultrasonic transducers and/or two or more RF electrodes). Further, where the surgical instrument comprises an ultrasonic components, the waveform signal may be configured to drive at least two vibration modes of an ultrasonic transducer of the at least one surgical instrument. Accordingly, a generator may be configured to provide a waveform signal to at least one surgical instrument wherein the waveform signal corresponds to at least one wave shape of a plurality of wave shapes in a table. Further, the waveform signal provided to the two surgical instruments may comprise two or more wave shapes. The table may comprise information associated with a plurality of wave shapes and the table may be stored within the generator. In one embodiment or example, the table may be a direct digital synthesis table, which may be stored in an FPGA of the generator. The table may be addressed by anyway that is convenient for categorizing wave shapes. According to one embodiment, the table, which may be a direct digital synthesis table, is addressed according to a frequency of the waveform signal. Additionally, the information associated with the plurality of wave shapes may be stored as digital information in the table.

The analog electrical signal waveform may be configured to control at least one of an output current, an output voltage, or an output power of an ultrasonic transducer and/or an RF electrode, or multiples thereof (e.g., two or more ultrasonic transducers and/or two or more RF electrodes). Further, where the surgical instrument comprises ultrasonic components, the analog electrical signal waveform may be configured to drive at least two vibration modes of an ultrasonic transducer of the at least one surgical instrument. Accordingly, the generator 100 may be configured to provide an analog electrical signal waveform to at least one surgical instrument wherein the analog electrical signal waveform corresponds to at least one wave shape of a plurality of wave shapes stored in a lookup table 1304. Further, the analog electrical signal waveform provided to the two surgical instruments may comprise two or more wave shapes. The lookup table 1304 may comprise information associated with a plurality of wave shapes and the lookup table 1304 may be stored either within the generator 100 or the surgical instrument. In one embodiment or example, the lookup table 1304 may be a direct digital synthesis table, which may be stored in an FPGA of the generator 100 or the surgical instrument. The lookup table 1304 may be addressed by anyway that is convenient for categorizing wave shapes. According to one aspect, the lookup table 1304, which may be a direct digital synthesis table, is addressed according to a frequency of the desired analog electrical signal waveform. Additionally, the information associated with the plurality of wave shapes may be stored as digital information in the lookup table 1304.

With the widespread use of digital techniques in instrumentation and communications systems, a digitally-controlled method of generating multiple frequencies from a reference frequency source has evolved and is referred to as direct digital synthesis. The basic architecture is shown in FIG. 13. In this simplified block diagram, a DDS circuit is coupled to a processor, controller, or a logic device of the generator 100 and to a memory circuit located either in the generator 100 or the surgical instrument 104, 106, 108 (FIG. 1). The DDS circuit 1300 comprises an address counter 1302, lookup table 1304, a register 1306, a DAC circuit 1308, and a filter 1312. A stable clock $f_c$ is received by the address counter 1302 and the register 1306 drives a programmable-read-only-memory (PROM) which stores one or more integral number of cycles of a sinewave (or other arbitrary waveform) in a lookup table 1304. As the address counter 1302 steps through each memory location, values stored in the lookup table 1304 are written to a register 1306, which is coupled to a DAC circuit 1308. The corresponding digital amplitude of the signal at each location of the lookup table 1304 drives the DAC circuit 1308, which in turn generates an analog output signal 1310. The spectral purity of the analog output signal 1310 is determined primarily by the DAC circuit 1308. The phase noise is basically that of the reference clock $f_c$. The first analog signal 1310 output from the DAC circuit 1308 is filtered by the filter 1312 and a second analog output signal 1314 output by the filter 1312 is provided to an amplifier having an output coupled to the output of the generator 100. The second analog output signal has a frequency $f_{out}$.

Because the DDS circuit 1300 is a sampled data system, issues involved in sampling must be considered: quantization noise, aliasing, filtering, etc. For instance, the higher order harmonics of the DAC circuit 1308 output frequencies fold back into the Nyquist bandwidth, making them unfilterable, whereas, the higher order harmonics of the output of phase-locked-loop (PLL) based synthesizers can be filtered. The lookup table 1304 contains signal data for an integral number of cycles. The final output frequency $f_{out}$ can be changed changing the reference clock frequency $f_c$ or by reprogramming the PROM.

Figure 15:
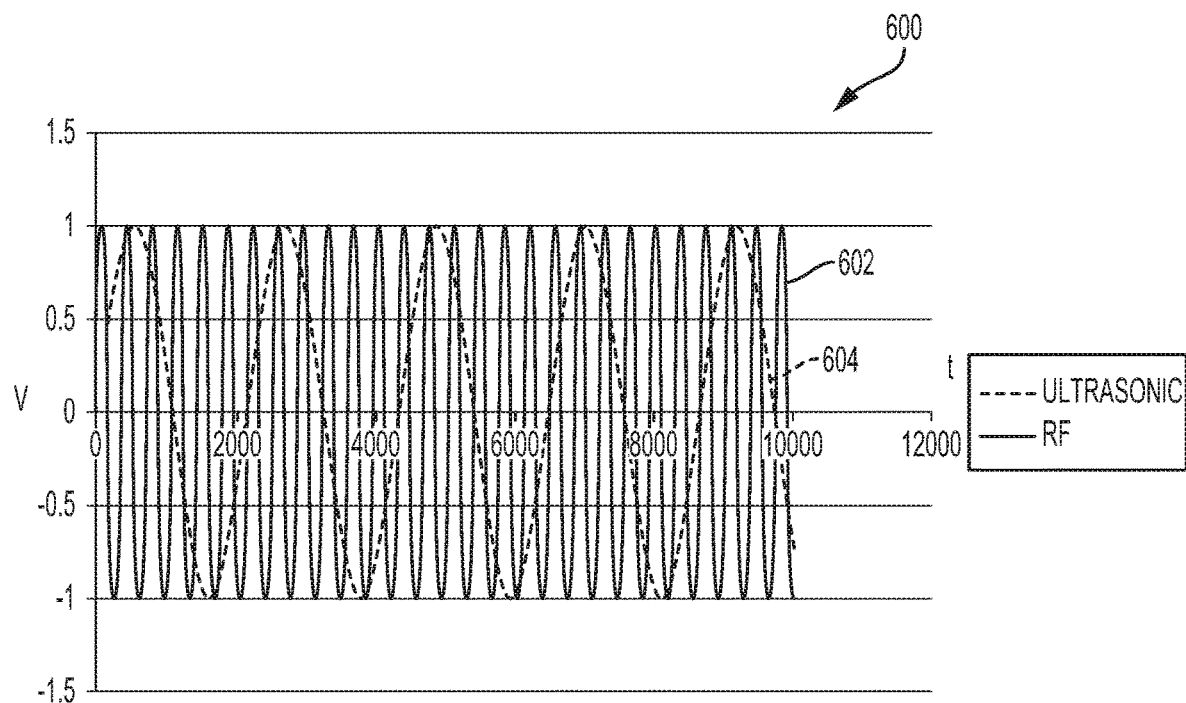
FIG. 15 is an example graph of two waveforms of energy from a generator.

The DDS circuit 1300 may comprise multiple lookup tables 1304 where each lookup table 1304 stores a waveform represented by a predetermined number of samples, wherein the samples define a predetermined shape of the waveform. Thus multiple waveforms, each having a unique shape, can be stored in multiple lookup tables 1304 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 1300 can create multiple wave shape lookup tables 1304 and during a tissue treatment procedure (e.g., "on-the-fly" or in virtual real time based on user or sensor inputs) switch between different wave shapes stored in different lookup tables 1304 based on the tissue effect desired and/or tissue feedback. Accordingly, switching between wave shapes can be based on tissue impedance and other factors, for example. In other aspects, the lookup tables 1304 can store electrical signal waveforms shaped to maximize the power delivered into the tissue per cycle (i.e., trapezoidal or square wave). In other aspects, the lookup tables 1304 can store wave shapes synchronized in such way that they make maximizing power delivery by the multifunction surgical instrument 108 when it delivering both RF and ultrasonic drive signals. In yet other aspects, the lookup tables 1304 can store electrical signal waveforms to drive both ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator 100 or in the non-volatile memory (e.g., EEPROM) of the multifunction surgical instrument 108 and be fetched upon connecting the multifunction surgical instrument 108 to the generator 100. An example of an exponentially damped sinusoid, as used in many high crest factor "coagulation" waveforms is shown in FIG. 15.

A more flexible and efficient implementation of the DDS circuit 1300 employs a digital circuit called a Numerically Controlled Oscillator (NCO). A block diagram of a more flexible and efficient digital synthesis circuit such as a DDS circuit 1400 is shown in FIG. 15. In this simplified block diagram, a DDS circuit 1400 is coupled to a processor, controller, or a logic device of the generator 100 and to a memory circuit located either in the generator 100 or the surgical instrument 104, 106, 108 (FIG. 1). The DDS circuit 1400 comprises a load register 1402, a parallel delta phase register 1404, an adder circuit 1416, a phase register 1408, a lookup table 1410 (phase-to-amplitude converter), a DAC circuit 1412, and a filter 14142. The adder circuit 1416 and the phase register 1408 a form part of a phase accumulator 1406. A clock signal $f_c$ is applied to the phase register 1408 and the DAC circuit 1412. The load register 1402 receives a tuning word that specifies output frequency as a fraction of the reference clock frequency $f_c$. The output of the load register 1402 is provided to a parallel delta phase register 1404 with a tuning word M.

The DDS circuit 1400 includes a sample clock that generates a clock frequency $f_c$, a phase accumulator 1406, and a lookup table 1410 (e.g., phase to amplitude converter). The content of the phase accumulator 1406 is updated once each clock cycle $f_c$. Each time the phase accumulator 1406 is updated, the digital number, M, stored in the parallel delta phase register 1404 is added to the number in the phase register 1408 by an adder circuit 1416. Assuming that the number in the parallel delta phase register 1404 is 00 . . . 01 and that the initial contents of the phase accumulator 1406 is 00 . . . 00. The phase accumulator 1406 is updated by 00 . . . 01 on each clock cycle. If the phase accumulator 1406 is 32-bits wide, 232 clock cycles (over 4 billion) are required before the phase accumulator 1406 returns to 00 . . . 00, and the cycle repeats.

The truncated output 1418 of the phase accumulator 1406 is provided to a phase-to amplitude converter lookup table 1410 and the output of the lookup table 1410 is coupled to a DAC circuit 1412. The truncated output 1418 of the phase accumulator 1406 serves as the address to a sine (or cosine) lookup table. Each address in the lookup table corresponds to a phase point on the sinewave from 0° to 360°. The lookup table 1410 contains the corresponding digital amplitude information for one complete cycle of a sinewave. The lookup table 1410 therefore maps the phase information from the phase accumulator 1406 into a digital amplitude word, which in turn drives the DAC circuit 1412. The output of the DAC circuit is a first analog signal 1420 and is filtered by a filter 1414. The output of the filter 1414 is a second analog signal 1422, which is provided to a power amplifier 212, 326, 426, 506 (FIGS. 5-8) coupled to the output of the generator 100.

In one aspect, the electrical signal waveform may be digitized into 1024 ($2^{10}$) phase points, although the wave shape may be digitized is any suitable number of $2^n$ phase points ranging from 256 ($2^8$) to 281,474,976,710,656 ($2^{48}$), where n is a positive integer, as shown in TABLE 1. The electrical signal waveform may be expressed as $A_n(\theta_n)$, where a normalized amplitude $A_n$ at a point n is represented by a phase angle $\theta_n$ is referred to as a phase point at point n. The number of discrete phase points n determines the tuning resolution of the DDS circuit 1400 (as well as the DDS circuit 1300 shown in FIG. 13).

TABLE 1

| n | Number of Phase Points $2^n$ |
|---|---|
| 8 | 256 |
| 10 | 1,024 |
| 12 | 4,096 |
| 14 | 16,384 |
| 16 | 65,536 |
| 18 | 262,144 |
| 20 | 1,048,576 |
| 22 | 4,194,304 |
| 24 | 16,777,216 |
| 26 | 67,108,864 |
| 28 | 268,435,456 |
| . . . | . . . |
| 32 | 4,294,967,296 |
| . . . | . . . |
| 48 | 281,474,976,710,656 |
| . . . | . . . |

The generator 100 algorithms and digital control circuits scan the addresses in the lookup table 1410, which in turn provides varying digital input values to the DAC circuit 1412 that feeds the filter 1414 and the power amplifier. The addresses may be scanned according to a frequency of interest. Using the lookup table enables generating various types of shapes that can be converted into an analog output signal by the DAC circuit 1412, filtered by the filter 1414, amplified by the power amplifier coupled to the output of the generator 100, and fed to the tissue in the form of RF energy or fed to an ultrasonic transducer and applied to the tissue in the form of ultrasonic vibrations which deliver energy to the tissue in the form of heat. The output of the amplifier can be applied to a single RF electrode, multiple RF electrodes simultaneously, a single ultrasonic transducer, multiple ultrasonic transducers simultaneously, or a combination of RF and ultrasonic transducers, for example. Furthermore, multiple wave shape tables can be created, stored, and applied to tissue from a single generator 100.

With reference back to FIG. 14, for n=32, and M=1, the phase accumulator 1406 steps through each of $2^{32}$ possible outputs before it overflows and restarts. The corresponding output wave frequency is equal to the input clock frequency divided by $2^{32}$. If M=2, then the phase register 1408 "rolls over" twice as fast, and the output frequency is doubled. This can be generalized as follows.

For an n-bit phase accumulator 1406 (n generally ranges from 24 to 32 in most DDS systems, but as previously discussed n may be selected from a wide range of options), there are $2^n$ possible phase points. The digital word in the delta phase register, M, represents the amount the phase accumulator is incremented each clock cycle. If fc is the clock frequency, then the frequency of the output sinewave is equal to:

$$f_o = \frac{M \cdot f_c}{2^n} \qquad \text{Eq. 1}$$

Equation 1 is known as the DDS "tuning equation." Note that the frequency resolution of the system is equal to $f_c/2^n$. For n=32, the resolution is greater than one part in four billion. In one aspect of the DDS circuit 1400, not all of the bits out of the phase accumulator 1406 are passed on to the lookup table 1410, but are truncated, leaving only the first 13 to 15 most significant bits (MSBs), for example. This reduces the size of the lookup table 1410 and does not affect the frequency resolution. The phase truncation only adds a small but acceptable amount of phase noise to the final output.

The electrical signal waveform may be characterized by a current, voltage, or power at a predetermined frequency. Further, where the multifunction surgical instrument 108 comprises ultrasonic components, the electrical signal waveform may be configured to drive at least two vibration modes of an ultrasonic transducer of the at least one multifunction surgical instrument 108. Accordingly, the generator 100 may be configured to provide an electrical signal waveform to at least one multifunction surgical instrument 108 wherein the electrical signal waveform is characterized by a predetermined wave shape stored in the lookup table 1410 (or lookup table 1304 FIG. 13). Further, the electrical signal waveform may be a combination of two or more wave shapes. The lookup table 1410 may comprise information associated with a plurality of wave shapes. In one aspect or example, the lookup table 1410 may be generated by the DDS circuit 1400 and may be referred to as a direct digital synthesis table. DDS works by first storing a large repetitive waveform in onboard memory. Any single cycle of a waveform (sine, triangle, square, arbitrary) can be represented by a predetermined number of phase points as shown in TABLE 1 and stored into memory. Once the waveform is stored into memory, it can be generated at very precise frequencies. The direct digital synthesis table may be stored in a non-volatile memory of the generator 100 and/or may be implemented with a FPGA circuit in the generator 100. The lookup table 1410 may be addressed by any suitable technique that is convenient for categorizing wave shapes. According to one aspect, the lookup table 1410 is addressed according to a frequency of the electrical signal waveform. Additionally, the information associated with the plurality of wave shapes may be stored as digital information in a memory or as part of the lookup table 1410.

In one aspect, the generator 100 may be configured to provide electrical signal waveforms to at least two surgical instruments simultaneously. The generator 100 also may be configured to provide the electrical signal waveform, which may be characterized two or more wave shapes, via a single output channel of the generator 100 to the two surgical instruments simultaneously. For example, in one aspect the electrical signal waveform comprises a first electrical signal to drive an ultrasonic transducer (e.g., ultrasonic drive signal), a second RF drive signal, and/or a combination of both. In addition, an electrical signal waveform may comprise a plurality of ultrasonic drive signals, a plurality of RF drive signals, and/or a combination of a plurality of ultrasonic and RF drive signals.

In addition, a method of operating the generator 100 according to the present disclosure comprises generating an electrical signal waveform and providing the generated electrical signal waveform to at least one multifunction surgical instrument 108, where generating the electrical signal waveform comprises receiving information associated with the electrical signal waveform from a memory. The generated electrical signal waveform comprises at least one wave shape. Furthermore, providing the generated electrical signal waveform to the at least one multifunction surgical instrument 108 comprises providing the electrical signal waveform to at least two surgical instruments simultaneously.

The generator 100 as described herein may allow for the generation of various types of direct digital synthesis tables. Examples of wave shapes for RF/Electrosurgery signals suitable for treating a variety of tissue generated by the generator 100 include RF signals with a high crest factor (which may be used for surface coagulation in RF mode), a low crest factor RF signals (which may be used for deeper tissue penetration), and waveforms that promote efficient touch-up coagulation. The generator 100 also may generate multiple wave shapes employing a direct digital synthesis lookup table 1410 and, on the fly, can switch between particular wave shapes based on the desired tissue effect. Switching may be based on tissue impedance and/or other factors.

In addition to traditional sine/cosine wave shapes, the generator 100 may be configured to generate wave shape(s) that maximize the power into tissue per cycle (i.e., trapezoidal or square wave). The generator 100 may provide wave shape(s) that are synchronized to maximize the power delivered to the load when driving both RF and ultrasonic signals simultaneously and to maintain ultrasonic frequency lock, provided that the generator 100 includes a circuit topology that enables simultaneously driving RF and ultrasonic signals. Further, custom wave shapes specific to instruments and their tissue effects can be stored in a non-volatile memory (NVM) or an instrument EEPROM and can be fetched upon connecting the multifunction surgical instrument 108 to the generator 100.

Figure 19:
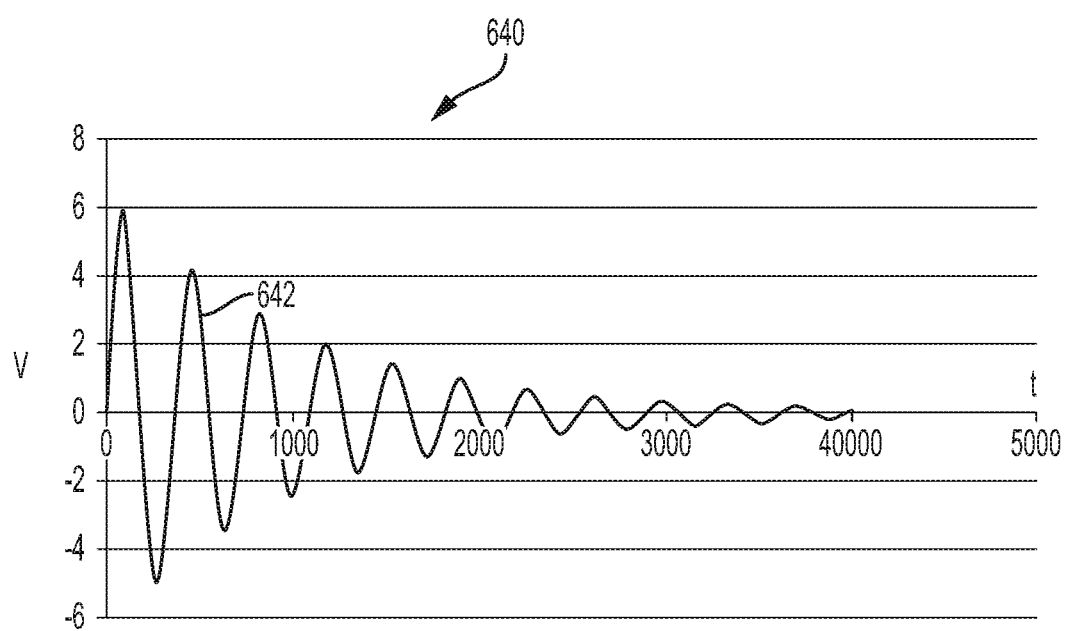
FIG. 19 is an example graph of a complex RF waveform.

The DDS circuit 1400 may comprise multiple lookup tables 1304 where each lookup table 1410 stores a waveform represented by a predetermined number of phase points (also may be referred to as samples), wherein the phase points define a predetermined shape of the waveform. Thus multiple waveforms, each having a unique shape, can be stored in multiple lookup tables 1410 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 1400 can create multiple wave shape lookup tables 1410 and during a tissue treatment procedure (e.g., "on-the-fly" or in virtual real time based on user or sensor inputs) switch between different wave shapes stored in different lookup tables 1410 based on the tissue effect desired and/or tissue feedback. Accordingly, switching between wave shapes can be based on tissue impedance and other factors, for example. In other aspects, the lookup tables 1410 can store electrical signal waveforms shaped to maximize the power delivered into the tissue per cycle (i.e., trapezoidal or square wave). In other aspects, the lookup tables 1410 can store wave shapes synchronized in such way that they make maximizing power delivery by the multifunction surgical instrument 108 when it delivering both RF and ultrasonic drive signals. In yet other aspects, the lookup tables 1410 can store electrical signal waveforms to drive both ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator 100 or in the non-volatile memory (e.g., EEPROM) of the multifunction surgical instrument 108 and be fetched upon connecting the multifunction surgical instrument 108 to the generator 100. An example of an exponentially damped sinusoid, as used in many high crest factor "coagulation" waveforms is shown in FIG. 19.

Examples of waveforms representing energy for delivery from a generator are illustrated in FIGS. 15-19. FIG. 15 illustrates an example graph 600 showing first and second individual waveforms representing an RF output signal 602 and an ultrasonic output signal 604 superimposed on the same time and voltage scale for comparison purposes. These output signals 602, 604 are provided at the ENERGY output of the generator 100. Time (t) is shown along the horizontal axis and voltage (V) is shown along the vertical axis. The RF output signal 602 has a frequency of about 330 kHz RF and a peak-to-peak voltage of ±1V. The ultrasonic output signal 604 has a frequency of about 55 kHz and a peak-to-peak voltage of ±1V. It will be appreciated that the time (t) scale along the horizontal axis and the voltage (V) scale along the vertical axis are normalized for comparison purposes and may be different actual implementations, or represent other electrical parameters such as current.

Figure 16:
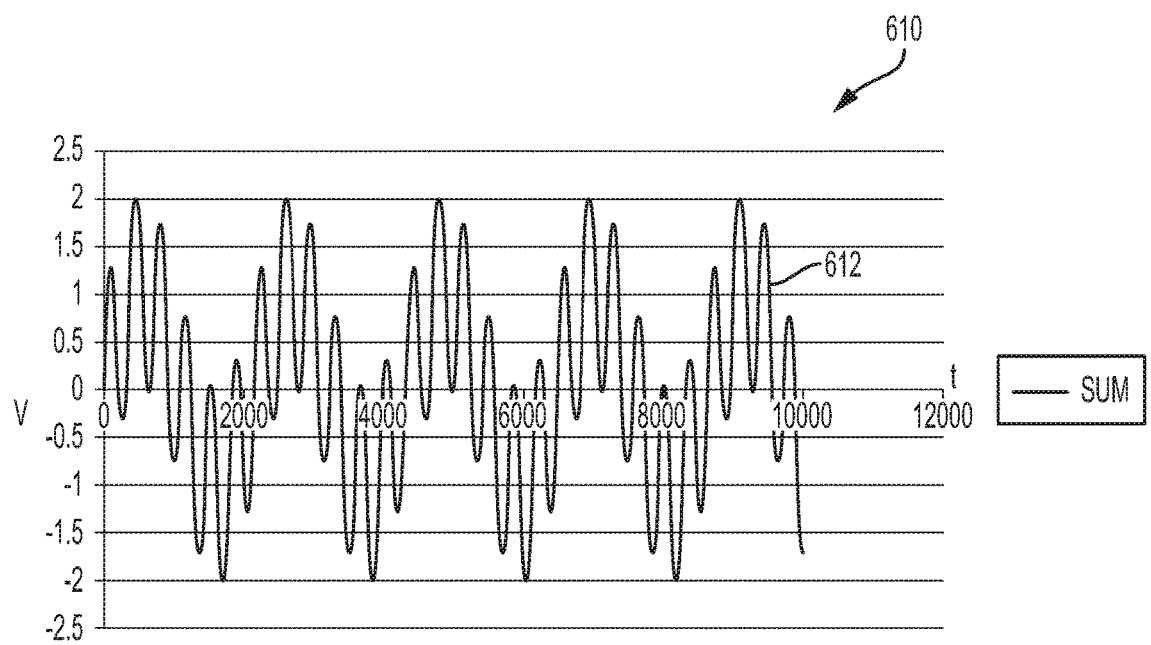
FIG. 16 is an example graph of the sum of the waveforms of FIG. 15.

FIG. 16 illustrates an example graph 610 showing the sum of the two output signals 602, 604 shown in FIG. 15. Time (t) is shown along the horizontal axis and voltage (V) is shown along the vertical axis. The sum of the RF output signal 602 and the ultrasonic output signal 604 shown in FIG. 15 produces a combined output signal 612 having a 2V peak-to-peak voltage, which is twice the amplitude of the original RF and ultrasonic signals shown (1V peak-to-peak) shown in FIG. 15. An amplitude of twice the original amplitude can cause problems with the output section of the generator, such as distortion, saturation, clipping of the output, or stresses on the output components. Thus, the management of a single combined output signal 612 that has multiple treatment components is an important aspect of the generator 500 shown in FIG. 8. There are a variety of ways to achieve this management. In one form, one of the two RF or ultrasonic output signals 602, 604 can be dependent on the peaks of the other output signal. In one aspect, the RF output signal 602 may depend on the peaks of the ultrasonic signal 604, such that the output is reduced when a peak is anticipated. Such a function and resulting waveform is shown in FIG. 17

Figure 17:
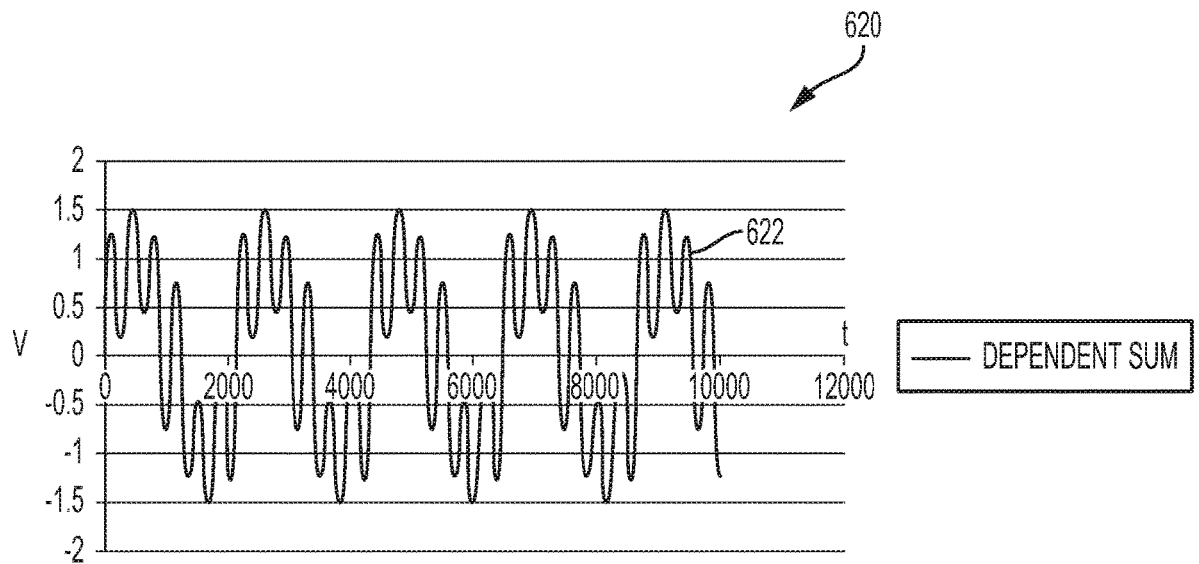
FIG. 17 is an example graph of sum of the waveforms of FIG. 15 with the RF waveform dependent on the ultrasonic waveform.

For example, FIG. 17 illustrates an example graph 620 showing a combined output signal 622 representative of a dependent sum of the output signals 602, 604 shown in FIG. 15. Time (t) is shown along the horizontal axis and voltage (V) is shown along the vertical axis. As shown in FIG. 17, the RF output signal 602 component of FIG. 15 depends on the peaks of the ultrasonic output signal 604 component of FIG. 15 such that the amplitude of the RF output signal component of the dependent sum combined output signal 622 is reduced when an ultrasonic peak is anticipated. As shown in the example graph 620 in FIG. 17, the peaks have been reduced from 2 to 1.5. In another form, one of the output signals is a function of the other output signal.

Figure 18:
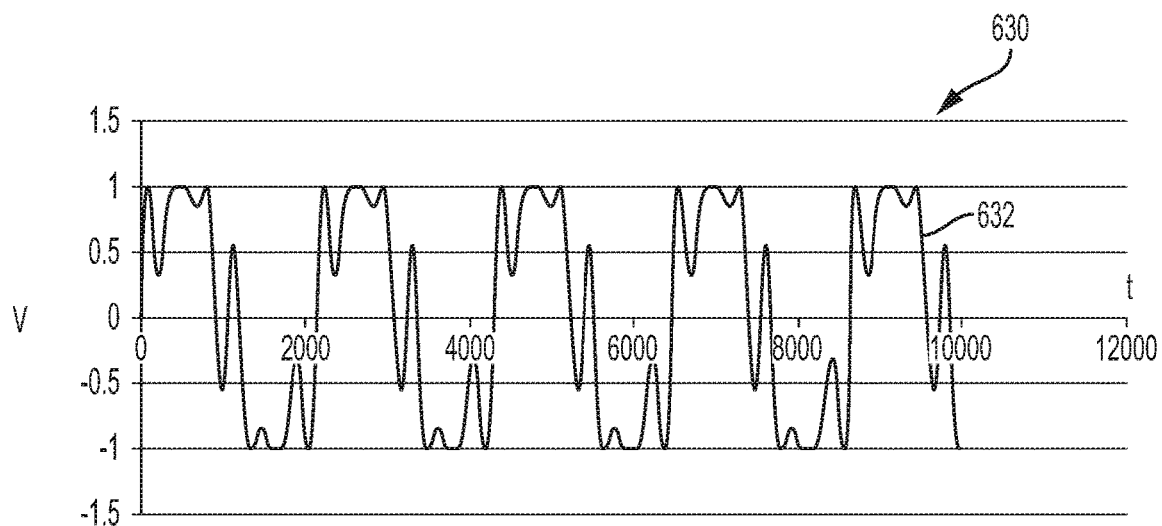
FIG. 18 is an example graph of the sum of the waveforms of FIG. 15 with the RF waveform being a function of the ultrasonic waveform.

For example, FIG. 18 illustrates an example graph of an analog waveform 630 showing an output signal 632 representative of a dependent sum of the output signals 602, 604 shown in FIG. 15. Time (t) is shown along the horizontal axis and voltage (V) is shown along the vertical axis. As shown in FIG. 18, the RF output signal 602 is a function of the ultrasonic output signal 604. This provides a hard limit on the amplitude of the output. As shown in FIG. 18, the ultrasonic output signal 604 is extractable as a sine wave while the RF output signal 602 has distortion but not in a way to affect the coagulation performance of the RF output signal 602.

A variety of other techniques can be used for compressing and/or limiting the waveforms of the output signals. It should be noted that the integrity of the ultrasonic output signal 604 (FIG. 15) can be more important than the integrity of the RF output signal 602 (FIG. 15) as long as the RF output signal 602 has low frequency components for safe patient levels so as to avoid neuro-muscular stimulation. In another form, the frequency of an RF waveform can be changed on a continuous basis in order to manage the peaks of the waveform. Waveform control is important as more complex RF waveforms, such as a coagulation-type waveform 642, as illustrated in the graph 640 shown in FIG. 19, are implemented with the system. Again, time (t) is shown along the horizontal axis and voltage (V) is shown along the vertical axis. The coagulation-type waveform 642 illustrated in FIG. 19 has a crest factor of 5.8, for example.

Figure 14:
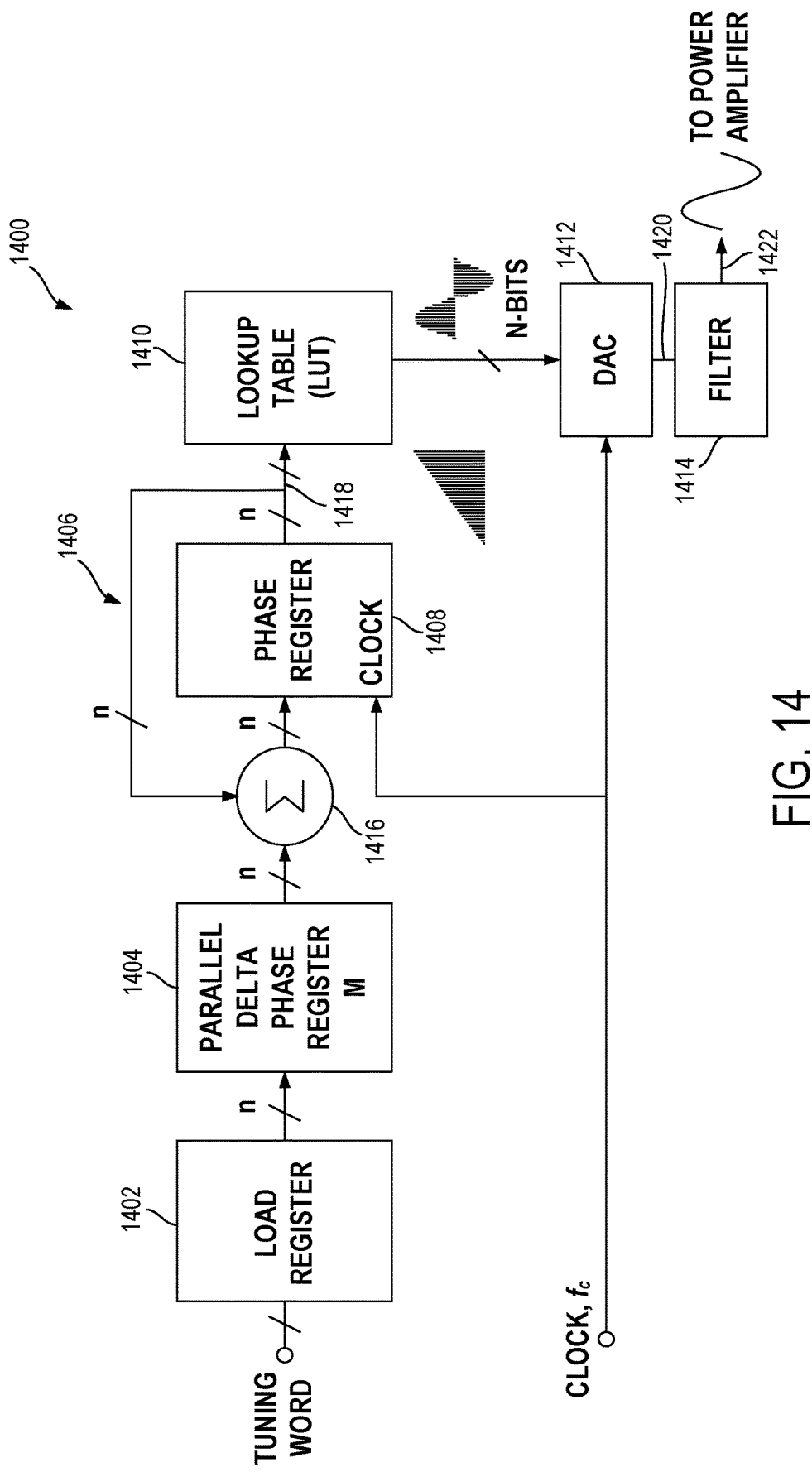
FIG. 14 is a diagram of one form of a direct digital synthesis circuit.
Figure 20:
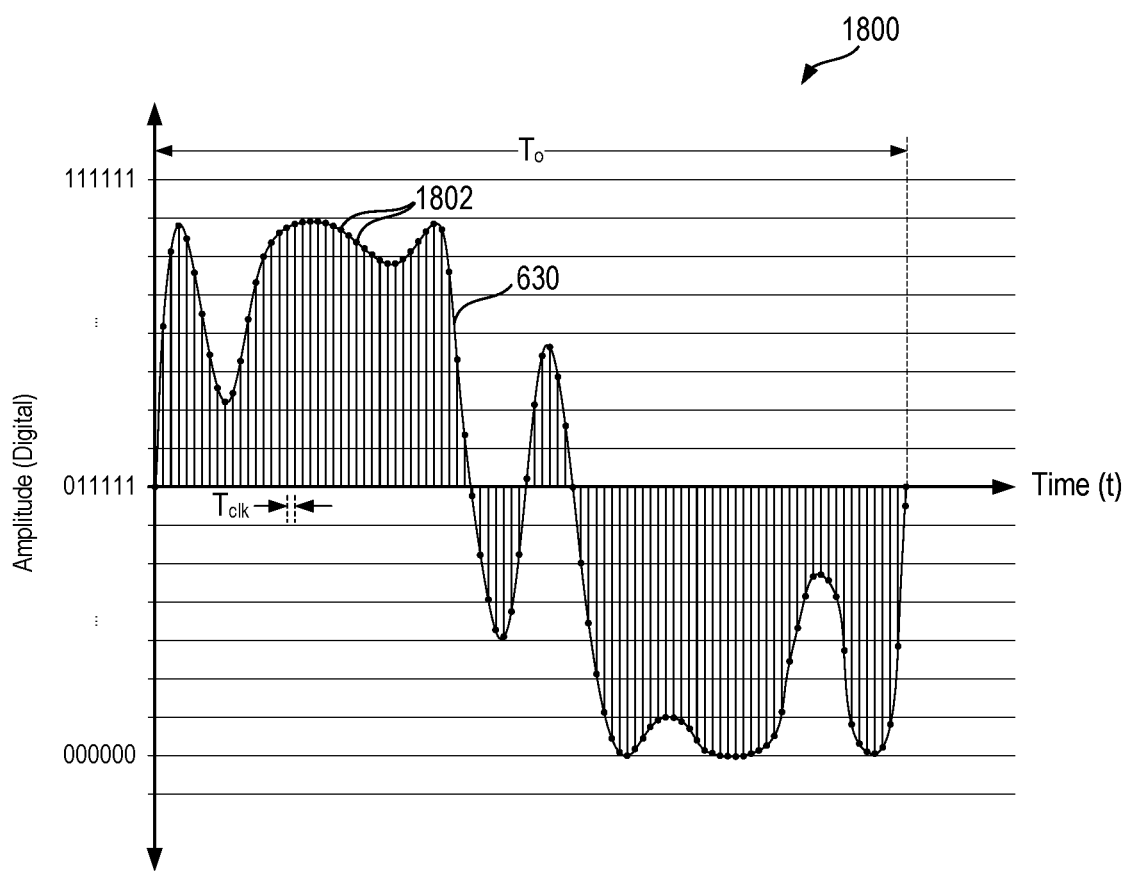
FIG. 20 illustrates one cycle of a digital electrical signal waveform shown in FIG. 18.

FIG. 20 illustrates one cycle of a digital electrical signal waveform 1800 of the analog waveform 630 shown in FIG. 18. The horizontal axis represents Time (t) and the vertical axis represents digital phase points. The digital electrical signal waveform 1800 is a digital version of the desired analog waveform 630 shown in FIG. 18, for example. The digital electrical signal waveform 1800 is generated by storing an amplitude phase point 1802 that represents the amplitude at each clock cycle $T_{clk}$ over one cycle or period $T_o$. The digital electrical signal waveform 1800 is generated over one period $T_o$ by any suitable digital processing circuit. The amplitude phase points are digital words stored in a memory circuit. In the example illustrated in FIG. 20, the digital word is a six-bit word that is capable of storing the amplitude phase points with a resolution of $2^6$ or 64 bits. It will be appreciated that the example shown in FIG. 20 is for illustrative purposes and in actual implementations the resolution can be much higher. The digital amplitude phase points 1802 over one cycle $T_o$ are stored in the memory as a string of string words in a lookup table 11304, 1410 as described in connection with FIGS. 13 and 14, for example. To generate the analog version of the waveform 630, the amplitude phase points 1802 are read sequentially from the memory from 0 to $T_o$ at each clock cycle $T_{clk}$ and are converted by a DAC circuit 1308, 1412, also described in connection with FIGS. 13 and 14. Additional cycles can be generated by repeatedly reading the amplitude phase points 1802 of the digital electrical signal waveform 1800 the from 0 to $T_o$ for as many cycles or periods as may be desired. The smooth analog version of the waveform 630 (also shown in FIG. 18) is achieved by filtering the output of the DAC circuit 1308, 1412 by a filter 1312, 1414 (FIGS. 13 and 14). The filtered analog output signal 1314, 1422 (FIGS. 13 and 14) is applied to the input of a power amplifier 212, 326, 426, 506 (FIGS. 5-8).

Figure 21:
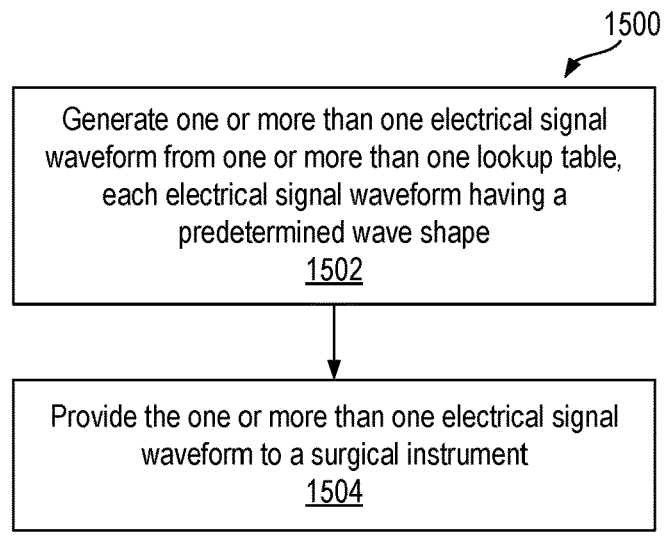
FIG. 21 is a logic flow diagram of a method of generating a digital electrical signal waveform according to one aspect.
Figure 22:
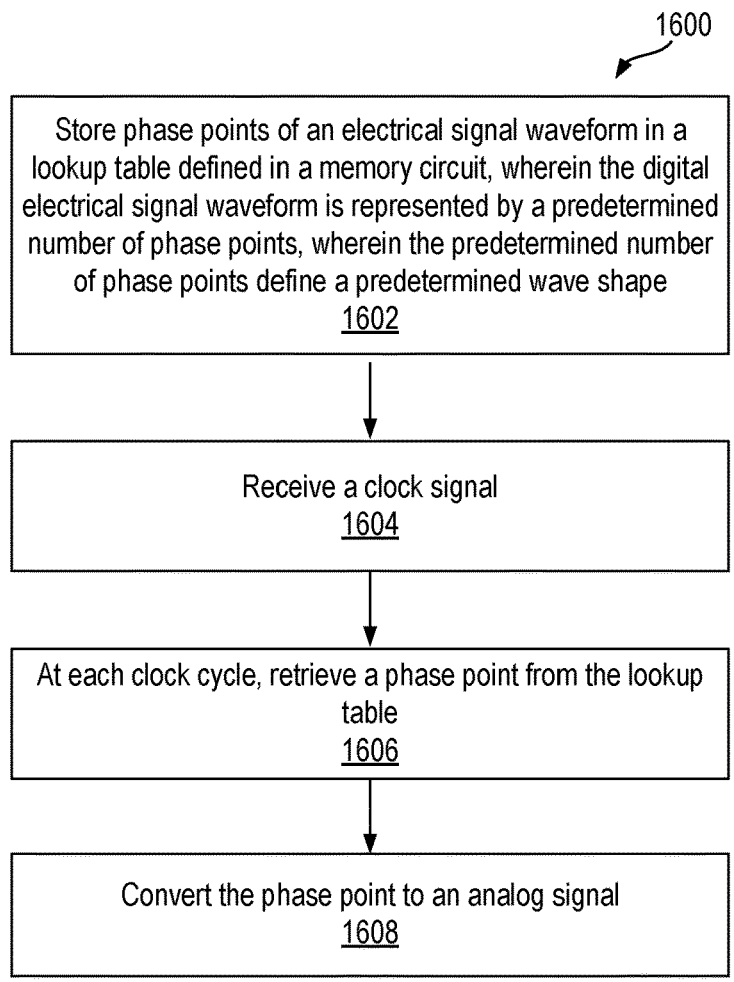
FIG. 22 is a logic flow diagram of a method of generating a digital electrical signal waveform according to another aspect.
Figure 23:
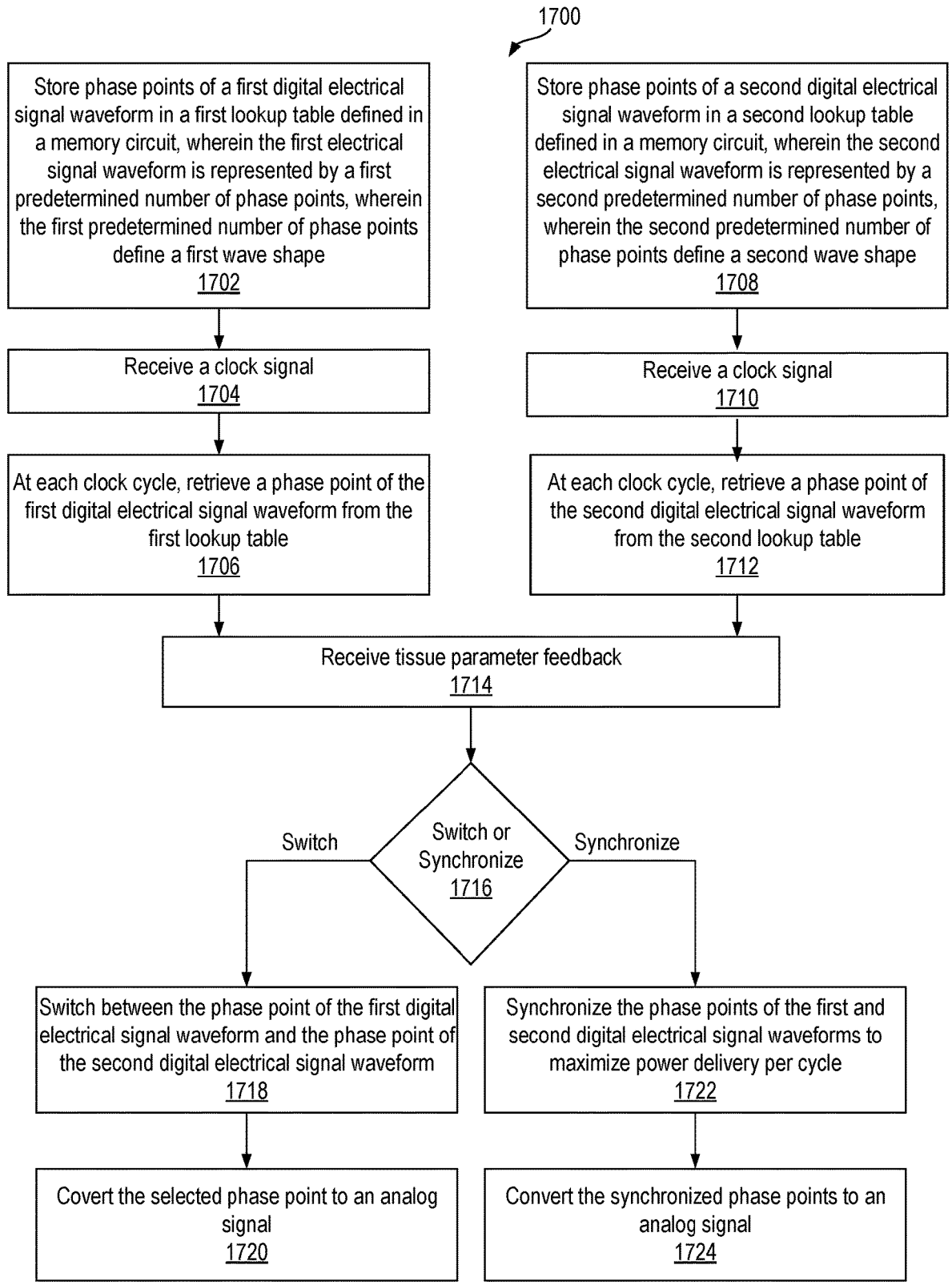
FIG. 23 is a logic flow diagram of a method of generating a digital electrical signal waveform according to another aspect.

FIGS. 21-23 are logic flow diagrams of methods 1500, 1600, 1700 of generating an electrical signal waveform by any of the generators 100, 200, 300, 400, 500, 9001, 1003, 1103, 1203 described herein. For conciseness and clarity the generators 100, 200, 300, 400, 500, 9001, 1003, 1103, 1203 will be referred to as the generator 100. Accordingly, the generator 100 is representative of the generators 200, 300, 400, 500, 9001, 1003, 1103, 1203 described herein. The methods 1500, 1600, 1700 will be described with reference to FIGS. 1, 13, 14, and 20 and FIGS. 5-8. The generator 100 comprises a digital processing circuit, a DDS circuit 1300, 1400, a memory circuit defining a lookup table 1304, 1410, and DAC circuit 1308, 1412, as described herein. The digital processing circuit may comprise any digital processing circuit, microprocessor, microcontroller, digital signal processor, logic device comprising combinational logic or sequential logic circuits, or any suitable digital circuit. The memory circuit may be located either in the surgical instrument 104, 106, 108 or the generator 100. In one aspect, the DDS circuit 1300, 1400 is coupled to the digital processing circuit and the memory circuit. In another aspect, the memory circuit is part of the DDS circuit 1300, 1400.

In various aspects, the generator 100 may be configured to drive multiple surgical instruments 104, 106, 108 simultaneously. Thus the generator 100 may be configured to drive the surgical instruments 104, 106, 108 in multiple vibration modes to achieve a longer active length at the ultrasonic blade 128, 149 and to create different tissue effects.

According to one of the present disclosure, the generator 100 may be configured to provide ultrasonic electrical signal waveforms defining a number of wave shapes to the surgical instrument 104, 108 to provide a desired therapy to tissue at the end effector 122, 125.

In one aspect, the generator 100 may be configured to generate a digital electrical signal waveform such that the desired wave shape can be digitized by a number of phase points or samples which are stored in a lookup table 1304, 1410 defined in volatile or non-volatile memory as discussed above in connection with FIGS. 13 and 14, for example. The phase points or samples may be stored in the lookup table 1304, 1410 defined in a FPGA, for example. The wave shape may be digitized into a number of phase points or samples as shown in TABLE 1. In one aspect, the wave shape may be digitized into 1024 phase points, for example. The digital processing circuit of the generator 100 may control by software or digital control the FPGA to scan the addresses in the lookup table 1304, 1410 which in turn provides varying digital input values to the DAC circuit 1308, 1412 that feeds a power amplifier 212, 326, 426, 506. The addresses may be scanned according to a frequency of interest. Using such the lookup table 1304, 1410 enables generating various types of wave shapes that can be used to drive the surgical instruments 104, 106, 108 simultaneously. Furthermore, multiple wave shape lookup tables 1304, 1410 can be created, stored, and applied to tissue from a single generator 100.

In one aspect, the electrical signal waveforms may be defined by an output current, an output voltage, an output power, or frequency suitable to drive the ultrasonic transducer 120 or multiple ultrasonic transducers (e.g. two or more ultrasonic transducers). In the case of the multifunction surgical instrument 108, in addition to driving the ultrasonic transducer 120, the electrical signal waveforms may be defined by an output current, an output voltage, an output power, or frequency suitable to drive the electrodes located in the end effector 125 of the multifunction surgical instrument 108.

Further, in one aspect where the surgical instrument 104, 108 comprises ultrasonic components, the electrical signal waveform may be configured to drive at least two vibration modes of the ultrasonic transducer 120. Accordingly, a generator 100 may be configured to provide a electrical signal waveform to at least one surgical instrument 104, 108 wherein the electrical signal waveform defines at least one wave shape selected out of a plurality of wave shapes stored in the lookup table 1304, 1410. Further, the electrical signal waveform provided to the two surgical instruments 104, 108 may define two or more wave shapes. The lookup table 1304, 1410 may comprise information associated with a plurality of wave shapes and the lookup table 1304, 1410 may be stored in a memory located either in the generator 100 or the surgical instruments 104, 108. In one embodiment or example, the lookup table 1304, 1410 may be a direct digital synthesis table, which may be stored in an FPGA located in the generator 100 or the surgical instruments 104, 108. The lookup table 1304, 1410 may be addressed using any suitable technique for categorizing wave shapes. According to one aspect, the DDS lookup table 1304, 1410 may be addressed according to the frequency of the electrical signal waveform. Additional information associated with the plurality of wave shapes also may be stored as digital information in the DDS lookup table 1304, 1410.

In one aspect, the generator 100 may comprise a DAC circuit 1308, 1412 and a power amplifier 212, 326, 426, 506. The DAC circuit 1308, 1412 is coupled to the power amplifier 212, 326, 426, 506 such that the DAC circuit 1308, 1412 provides the analog electrical signal waveform to a filter 1312, 1414 and the output of the filter 1312, 1414 is provided to the power amplifier 212, 326, 426, 506. The output of the power amplifier 212, 326, 426, 506 is provided to the surgical instrument 104, 108.

Further, in one aspect the generator 100 may be configured to provide the electrical signal waveform to the surgical instruments 104, 106, 108 simultaneously. This may be accomplished through a single output port or channel of the generator 100. The generator 100 also may be configured to provide the electrical signal waveform, which may define two or more wave shapes, via a single output port or channel to the two surgical instruments 104, 108 simultaneously. The analog signal output of the generator 100 may define multiple wave shapes to one or more than one surgical instruments 104, 108. For example, in one aspect, the electrical signal waveform comprises multiple ultrasonic drive signals. In another aspect, the electrical signal waveform comprises multiple ultrasonic drive signals and one or more than one RF signals. Accordingly, an electrical signal waveform output of the generator 100 may comprise multiple ultrasonic drive signals, multiple RF signals, and/or a combination of multiple ultrasonic drive signals and a RF signals.

In one aspect, the generator 100 as described herein may allow for the creation of various types of DDS lookup tables 1304, 1410 within an FPGA located in the generator 100. Some examples of the wave shapes that may be produced by the generator 100 include high crest factor signals (which may be used for surface coagulation), low crest factor signals (which may be used for deeper tissue penetration), and electrical signal waveforms that promote efficient touch-up coagulation. The generator 100 also may create multiple wave shape lookup tables 1304, 1410. The generator 100 can be configured to switch between different electrical signal waveforms for diving ultrasonic transducers 120 during a procedure (e.g., "on-the-fly" or in virtual real time based on user or sensor inputs) based on desired tissue effects or feedback signals associated with the state of the tissue located in the end effector 122, 125. Switching may be based on tissue impedance, tissue temperature, state of coagulation, state of dissection, and/or other factors.

In one aspect, the generator 100 as described herein also may provide, in addition to the traditional sine wave shape, wave shapes that maximizes the power into tissue per cycle (i.e. trapezoidal, square, or triangular wave shapes). It also may provide wave shapes that are synchronized in a manner that would maximize power delivery in the case of an electrical signal waveform comprises RF and ultrasonic signal components to drive ultrasonic and RF therapeutic energy simultaneously while maintaining ultrasonic frequency lock. Further, custom wave shapes specific to various types of surgical instruments 104, 108 and their tissue effects can be stored in a lookup table 1304, 1410 memory located in the generator 100 or the surgical instrument 104, 108, where the memory may be a volatile (RAM) or non-volatile (EEPROM) memory. The wave shape may be fetched from the lookup table 1304, 1410 memory upon connecting the surgical instrument 104, 108 to the generator 100.

With reference to FIG. 21, in accordance with the method 1500, the generator 100 is configured to generate 1502 one or more than one electrical signal waveform and provide 1504 the generated one or more than one electrical signal waveform to a surgical instrument 104, 106, 108. The generator 100 generates 1502 one or more than one digital electrical signal waveform from one or more lookup tables 1304, 1410 as described in connection with FIGS. 13 and 14. The one or more than one digital electrical signal waveform may be defined by a plurality of wave shapes that are combined to form a complex waveform. The lookup tables 1304, 1410 may be defined in a memory circuit in communication with a digital processing circuit of the generator 100 or the surgical instrument 104, 106, 108. In one aspect, the lookup tables 1304, 1410 may be DDS lookup tables that can be addressed according to a desired frequency of the electrical signal waveforms. In one aspect, the digital electrical signal waveform is a combination of at least two wave shapes. The combined digital electrical signal waveform is provided to the DAC circuit 1308, 1412 circuit and may be filtered by the filter 1312, 1414 and amplified by a power amplifier 212, 326, 426, 506. The combined analog electrical signal waveform may be an ultrasonic drive signal having a frequency of 55 kHz or an RF signal having a frequency of 330 kHz or a combination of the ultrasonic drive signal and the RF signal.

In one aspect, the method 1500 the power amplifier 212, 326, 426, 506 amplifies the analog signal 1310, 1420 output of the DAC circuit 1308, 1412. In addition, according to the method 1500, the digital processing circuit stores phase points of a digital electrical signal waveform in the lookup table 1304, 1410 defined by the memory circuit. The digital processing circuit stores phase points of multiple digital electrical signal waveforms in corresponding multiple lookup tables 1304, 1410 defined by the memory circuit or other memory circuits. Each of the digital electrical signal waveforms is represented by a predetermined number of phase points. Each of the predetermined number of phase points defines a different wave shape. In accordance with the method 1500, the digital processing circuit receives a feedback signal associated with tissue parameters and modifies the predetermined wave shape according to the feedback signal.

In one aspect, the digital electrical signal waveform represents a RF signal waveform, an ultrasonic signal waveform, or a combination thereof. In one aspect, the digital electrical signal waveform represents a combination of two waveforms having different amplitudes. In one aspect, the digital electrical signal waveform represents a combination of two waveforms having different frequencies. In one aspect, digital electrical signal waveform represents a combination of two waveforms having of different amplitudes. In one aspect, the wave shape is a trapezoid, a sine or cosine wave, a square wave, a triangle wave, or any combinations thereof. In one aspect, the digital electrical signal waveform is a combined RF and ultrasonic signal waveform configured to maintain a predetermined ultrasonic frequency. In one aspect, the first digital electrical signal waveform is a combined RF and ultrasonic waveform configured to deliver maximum power output.

According to various aspects, the electrical signal waveform also may be provided to at least two surgical instruments 104, 106, 108 simultaneously. The surgical instruments 104, 106, 108 may comprise instruments that operate the same modalities or different modalities of surgical treatment techniques. In one aspect, the surgical instruments include at least one ultrasonic surgical instrument and at least one RF surgical instrument.

With reference to FIG. 22, in accordance with the method 1600, the digital processing circuit instructs the DDS circuit 1300, 1400 to store 1602 phase points or samples that define a digital electrical signal waveform in a lookup table 1304, 1410 defined in the memory circuit. The digital electrical signal waveform is represented by a predetermined number of phase points that are stored in the lookup table 1304, 1410. The predetermined number of phase points define a predetermined wave shape. The DDS circuit 1300, 1400 receives 1604 a clock signal. At each clock cycle, the DDS circuit 1300, 1400 retrieves 1606 a phase point from the lookup table 1304, 1410 and provides the phase point (e.g., sample) to the DAC circuit 1308, 1412. The DAC circuit 1308, 1412 converts 1608 the phase point of the digital electrical signal waveform into an analog electrical signal output (e.g., a sample/hold output of the DAC circuit 1308, 1412). The analog sample/hold output of the DAC circuit 1308, 1412 is filtered by the filter 1312, 1414 and amplified by a power amplifier 212, 326, 426, 506, for example, before the analog electrical signal waveform is provided to the surgical instrument 104, 106, 108.

The analog electrical signal waveform may be of a type that provides for the application of a particular treatment modality for a surgical instrument connected to the generator. Accordingly, the analog electrical signal waveform may be a RF waveform, an ultrasonic waveform, or a combination thereof. The analog electrical signal waveform may be a combined RF and ultrasonic waveform and the combined RF and ultrasonic waveform may be configured to maintain a predetermined ultrasonic frequency. In one aspect, the predetermined ultrasonic frequency is a frequency lock based on a surgical instrument 104, 106, 108 connected to the generator 100. In another aspect, the analog electrical signal waveform is a combined RF and ultrasonic waveform and the combined RF and ultrasonic waveform is configured to cause a surgical instrument 104, 106, 108 to deliver a maximum power application of the surgical instrument 104, 106, 108 to tissue engaged with the surgical instrument 104, 106, 108. The maximum power application may be based on the maximum power output of a treatment modality of a surgical instrument 104, 106, 108, such as, for example, an RF modality or an ultrasonic modality. According to further aspects, the analog electrical signal waveform may comprise a high crest factor RF signal, a low crest factor RF signal, or a combination thereof and/or the electrical signal waveform may comprise a sine wave shape, a trapezoidal wave shape, a square wave shape, or a combination thereof. The analog electrical signal waveform may also be configured to provide a desired tissue effect or outcome to tissue engaged by a surgical instrument 104, 106, 108 when the analog electrical signal waveform is received by the surgical instrument 104, 106, 108. In one aspect, the desired tissue effect is at least one of cutting, coagulation, or sealing.

The generator 100 also may be configured to switch between digital or analog versions of multiple electrical signal waveforms. For example, the generator 100 may be configured to switch between a first electrical signal waveform and a second electrical signal waveform based on predetermined criteria, such as, for example, a desired tissue effect and/or feedback from a surgical instrument 104, 106, 108, which may include measured values of a tissue parameter. The tissue parameter may include a tissue type, a tissue amount, a tissue state, or a combination thereof. Accordingly, the method 1600 includes storing a plurality of electrical signal waveforms in a plurality of lookup tables defined in a memory circuit. The electrical signal waveforms are represented by a predetermined number of phase points, wherein the phase points define predetermined wave shapes based on desired tissue effects, tissue parameters, or other parameters associated with the surgical instrument 104, 106, 108 connected to the generator 100.

Additionally, digital phase points of the digital electrical signal waveform may be received by the generator 100 from a surgical instrument 104, 106, 108 connected to the generator 100. The generator 100 may receive the phase points following or upon connection of the surgical instrument 104, 106, 108 to the generator 100. The phase points of the digital electrical signal waveform may be stored in an EEPROM of the surgical instrument 104, 106, 108, which is operable coupled to the generator 100 upon connection of the surgical instrument 104, 106, 108 to the generator 100.

In accordance with the method 1600, the digital processing circuit receives a feedback signal associated with tissue parameters. In one aspect, based on the feedback signal the digital processing circuit switches between the phase point of the first digital electrical signal waveform and the phase point of the second digital electrical signal waveform and the DAC circuit 1308, 1412 converts the retrieved phase point. In another aspect, based on the feedback signal the digital processing circuit synchronizes the phase points of the first and second digital electrical signal waveforms to maximize power delivery per cycle and the DAC circuit 1308, 1412 circuit, the synchronized phase points. In one aspect, the first digital electrical signal waveform represents a RF waveform and the second digital electrical signal waveform represents an ultrasonic signal waveform.

With reference to FIG. 23, in accordance with the method 1700, the digital processing circuit instructs the DDS circuit 1300, 1400 to store 1702 a first digital electrical signal waveform in a first lookup table 1304, 1410 defined in the memory circuit. The first digital electrical signal waveform is represented by a first predetermined number of phase points that are stored in the first lookup table 1304, 1410. The first predetermined number of phase points define a first wave shape. The DDS circuit 1300, 1400 receives 1704 a clock signal. At each clock cycle, the DDS circuit 1300, 1400 retrieves 1706 a phase point from the first lookup table 1304, 1410.

In accordance with the method 1700, the digital processing circuit also instructs the DDS circuit 1300, 1400 to store 1708 a second digital electrical signal waveform in a second lookup table 1304, 1410 defined in the memory circuit, or other memory circuit. The second digital electrical signal waveform is represented by a second predetermined number of phase points that are stored in the second lookup table 1304, 1410. The second predetermined number of phase points define a second wave shape. The DDS circuit 1300, 1400 receives 1710 a clock signal. At each clock cycle, the DDS circuit 1300, 1400 retrieves 1712 a phase point from the second lookup table 1304, 1410.

In accordance with the method 1700, the generator 100 or the surgical instrument 104, 106, 108 receives 1714 tissue parameter feedback from sensors in the surgical instrument 104, 106, 108. The feedback may provide information regarding tissue impedance, tissue type, or temperature of the tissue. In other aspects, the feedback may be based on the temperature of the electrode or ultrasonic blade or electrical impedance of the ultrasonic transducer, among other feedback parameters. Based on the tissue parameter feedback, the digital processing circuit determines 1716 whether to switch between the first and second phase points of the first and second electrical signal waveforms or whether to synchronize the first and second phase points of the first and second electrical signal waveforms to maximize power delivery to the tissue per cycle.

If the method 1700 proceeds along the "switch" branch, the digital processing circuit switches 1718 between the phase point of the first digital electrical signal waveform and the phase point of the second digital electrical signal waveform during a tissue treatment procedure (e.g., "on-the-fly" or in virtual real time based on user or sensor inputs). The retrieved phase point of either the first or second electrical signal waveforms is provided to the DAC circuit 1308, 1412. The DAC circuit 1308, 1412 converts 1720 the retrieved phase point of either the first or second electrical signal waveforms to an analog electrical signal. The sample/hold analog output of the DAC circuit 1308, 1412 is filtered by the filter 1312, 1414 and amplified by a power amplifier 212, 326, 426, 506, for example, before the analog electrical signal waveform is provided to the surgical instrument 104, 106, 108.

If the method 1700 proceeds along the "synchronize" branch, the digital processing circuit synchronizes 1722 the phase points of the first and second digital electrical signal waveforms to maximize power delivery per cycle. The synchronized phase points of the first and second digital electrical signal waveforms are provided to the DAC circuit 1308, 1412. The DAC circuit 1308, 1412 converts 1724 the synchronized phase points of the first or second electrical signal waveforms to an analog electrical signal. The analog sample/hold output of the DAC circuit 1308, 1412 is filtered by the filter 1312, 1414 and amplified by a power amplifier 212, 326, 426, 506, for example, before the analog electrical signal waveform is provided to the surgical instrument 104, 106, 108.

In various aspects, the first and second electrical signal waveforms may represent electrical signals having different wave shapes. In one aspect, the first digital electrical signal waveform may represent an RF signal suitable for driving an electrode of an electrosurgical instrument 106 or a multifunction surgical instrument 108 and the second electrical signal waveform may represent an ultrasonic signal for driving an ultrasonic transducer of an ultrasonic instrument 104 or a multifunction surgical instrument 108. The first and second electrical signal waveforms can be delivered separately, simultaneously, individually, or combined in one signal.

Figure 24:
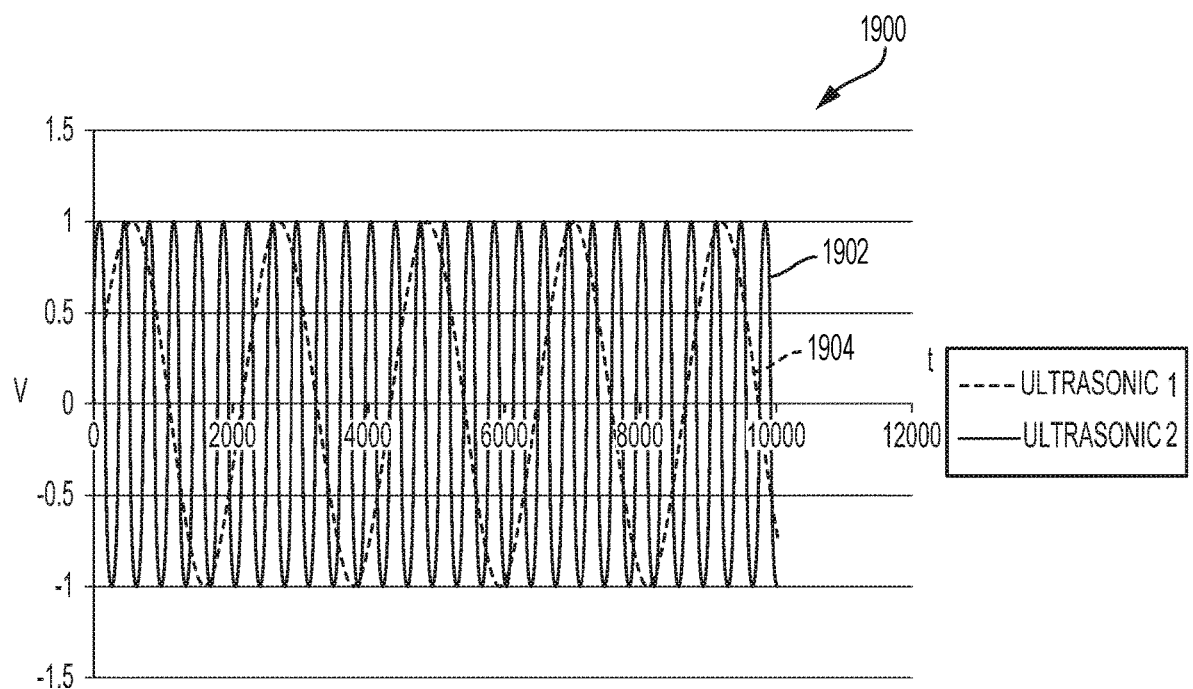
FIG. 24 is an example graph of two ultrasonic waveforms of energy produced by a generator.

Examples of waveforms representing energy for delivery from a generator are illustrated in FIGS. 24-28. FIG. 24 illustrates an example graph 1900 showing first and second individual waveforms representing a first ultrasonic output signal 1902 and a second ultrasonic output signal 1904 superimposed on the same time and voltage scale for comparison purposes. The frequency of the first ultrasonic output signal 1902 is greater than the second ultrasonic output signal 1904. The first and second ultrasonic output signals 1902, 1904 are provided at the ENERGY output of the generator 100. Time (t) is shown along the horizontal axis and voltage (V) is shown along the vertical axis. The first ultrasonic output signal 1902 may have a frequency of about 50 kHz to about 100 kHz and a peak-to-peak voltage of ±1V. The second ultrasonic output signal 604 has a frequency of about 20 kHz to 40 kHz and a peak-to-peak voltage of ±1V. It will be appreciated that the time (t) scale along the horizontal axis and the voltage (V) scale along the vertical axis are normalized for comparison purposes and may be different actual implementations, or represent other electrical parameters such as current. For comparison purposes, frequencies and amplitudes of the first and second ultrasonic output signals 1902, 1904 are not shown to scale. In other aspects, the frequency of the first ultrasonic output signal 1902 is the same as the frequency of the second ultrasonic output signal 1904. In one aspect, the first and second ultrasonic output signals 1902, 1904 may be combined as a sum as described in connection with FIG. 25.

Figure 25:
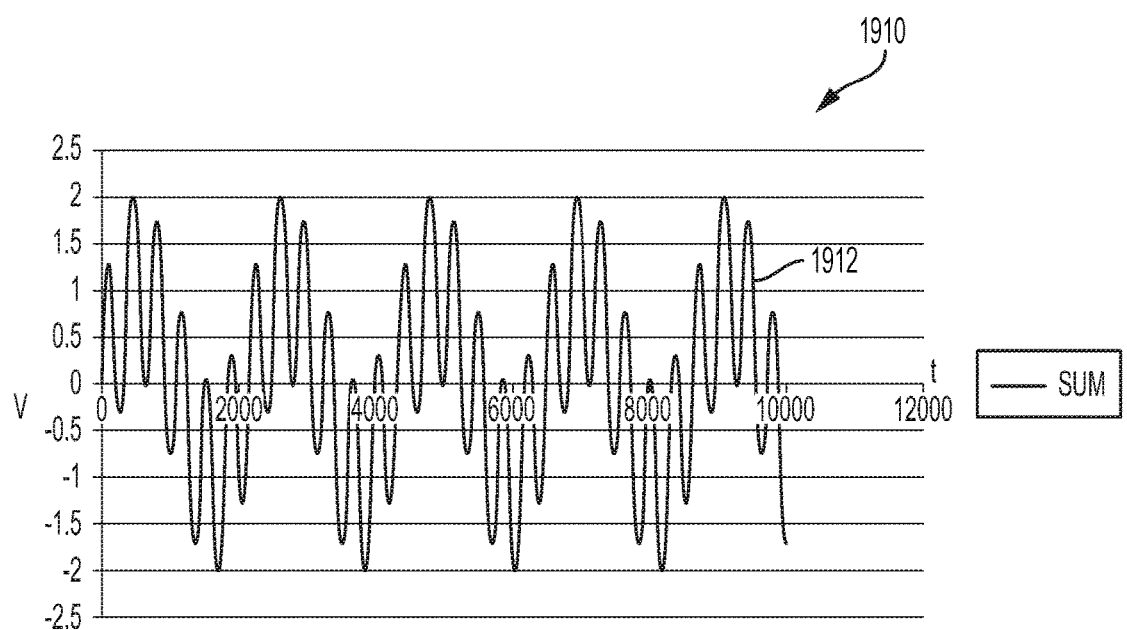
FIG. 25 is an example graph of the sum of the two ultrasonic waveforms of FIG. 24.

FIG. 25 illustrates an example graph 1910 showing the sum of the first and second ultrasonic output signals 1902, 1904 shown in FIG. 24. Time (t) is shown along the horizontal axis and voltage (V) is shown along the vertical axis. The sum of the first ultrasonic output signal 1902 and the second ultrasonic output signal 1904 shown in FIG. 24 produces a combined output signal 1912 having a 2V peak-to-peak voltage, which is twice the amplitude of the original first and second ultrasonic output signals 1902, 1904 shown (1V peak-to-peak) shown in FIG. 24. An amplitude of twice the original amplitude can cause problems with the output section of the generator, such as distortion, saturation, clipping of the output, or stresses on the output components. Thus, the management of a single combined output signal 1912 that has multiple treatment components is an important aspect of the generator 500 shown in FIG. 8. There are a variety of ways to achieve this management. In one form, one of the first and second ultrasonic output signals 1902, 1904 can be dependent on the peaks of the other output signal. In one aspect, the first and second ultrasonic output signals 1902, 1904 may be combined with one or more than one RF output signals.

Figure 26:
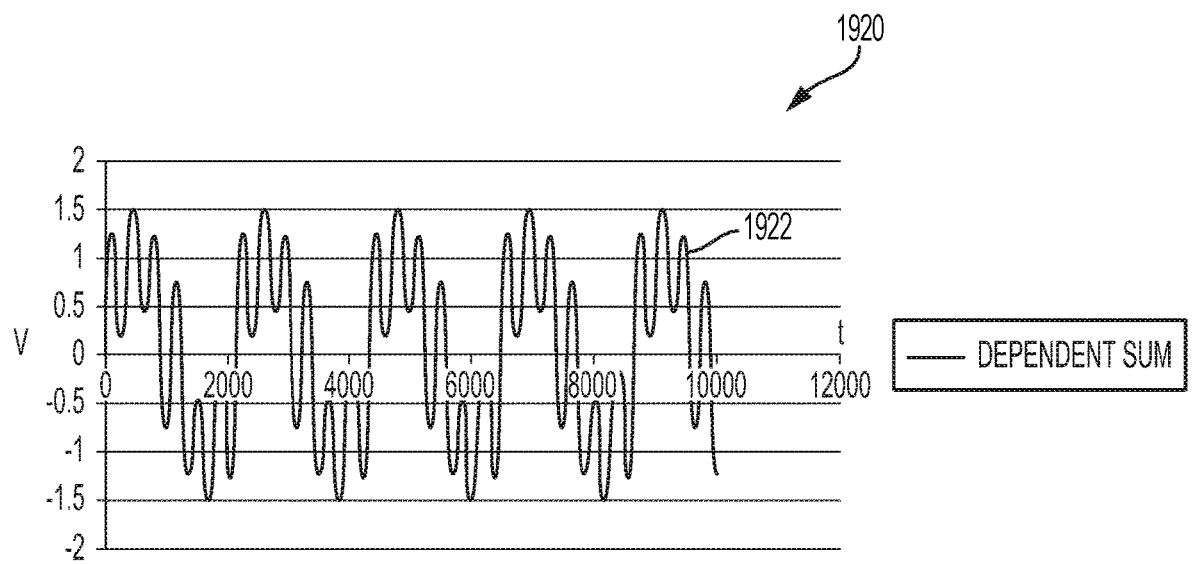
FIG. 26 is an example graph of sum of the waveforms of FIG. 24 with the higher frequency ultrasonic waveform dependent on the lower frequency ultrasonic waveform.

For example, FIG. 26 illustrates an example graph 1920 showing a combined output signal 1922 representative of a dependent sum of the first and second ultrasonic output signals 1902, 1904 shown in FIG. 24. Time (t) is shown along the horizontal axis and voltage (V) is shown along the vertical axis. As shown in FIG. 26, the first ultrasonic output signal 1902 component of FIG. 24 depends on the peaks of the second ultrasonic output signal 1904 component of FIG. 24 such that the amplitude of the first ultrasonic output signal component of the dependent sum combined output signal 1922 is reduced when a peak of the second ultrasonic signal is anticipated. As shown in the example graph 1920 in FIG. 26, the peaks have been reduced from 2 to 1.5. In another form, one of the output signals is a function of the other output signal. As previously discussed, in one aspect, the combined output signal may comprise RF signal components as well as ultrasonic signal components.

Figure 27:
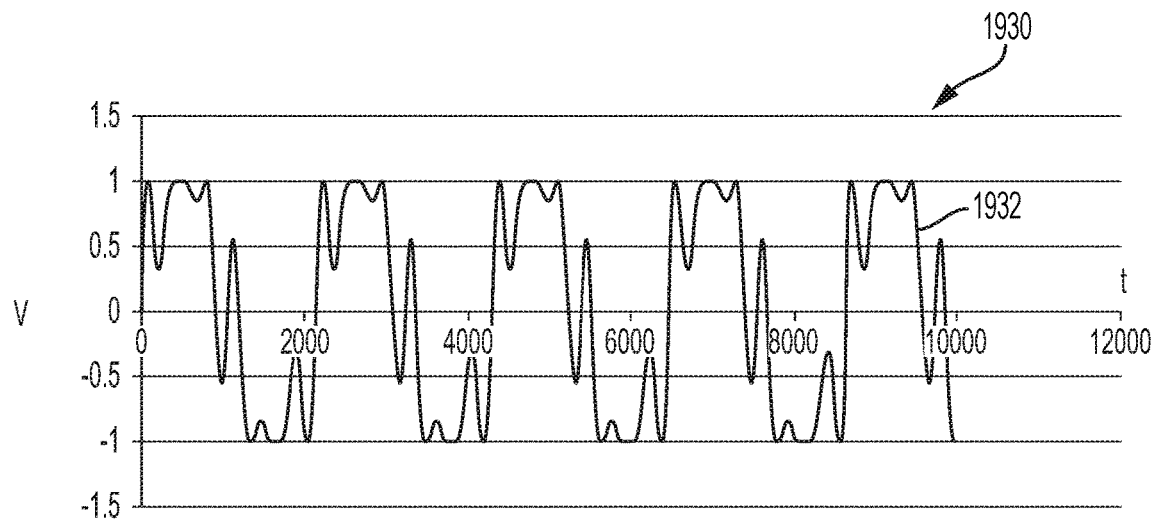
FIG. 27 is an example graph of the sum of the waveforms of FIG. 24 with the higher frequency ultrasonic waveform being a function of the lower frequency ultrasonic waveform.

For example, FIG. 27 illustrates an example graph of an analog waveform 1930 showing an output signal 1932 representative of a dependent sum of the first and second ultrasonic output signals 1902, 1904 shown in FIG. 24. Time (t) is shown along the horizontal axis and voltage (V) is shown along the vertical axis. As shown in FIG. 27, the first ultrasonic output signal 1902 is a function of the second ultrasonic output signal 1904. This provides a hard limit on the amplitude of the output. As shown in FIG. 27, the second ultrasonic output signal 1904 is extractable as a sine wave while the first ultrasonic output signal 1902 has distortion but not in a way to affect the coagulation performance of the first ultrasonic output signal 1902.

Figure 28:
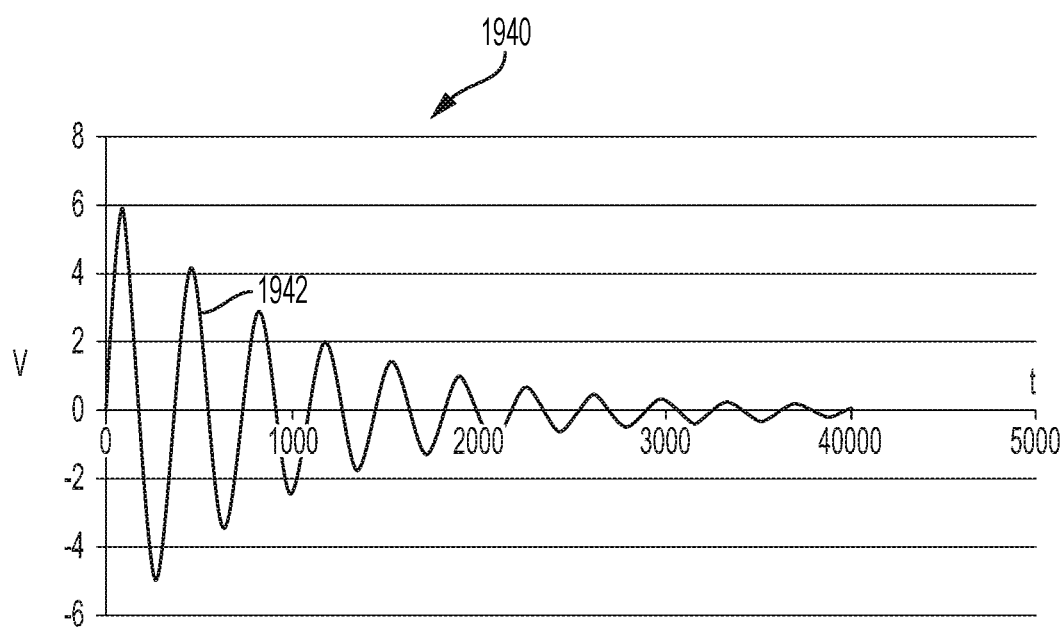
FIG. 28 is an example graph of a complex ultrasonic waveform.

A variety of other techniques can be used for compressing and/or limiting the waveforms of the output signals. It should be noted that the integrity of the second ultrasonic output signal 1904 (FIG. 24) can be more important than the integrity of the first ultrasonic output signal 1902 (FIG. 24) as long as the first ultrasonic output signal 1902 has low frequency components for safe patient levels so as to avoid neuro-muscular stimulation. In another form, the frequency of an ultrasonic waveform can be changed on a continuous basis in order to manage the peaks of the waveform. Waveform control is important as more complex ultrasonic waveforms, such as a coagulation-type waveform 1942, as illustrated in the graph 1940 shown in FIG. 28, are implemented with the system. Again, time (t) is shown along the horizontal axis and voltage (V) is shown along the vertical axis. The coagulation-type waveform 1942 illustrated in FIG. 28 has a crest factor of 5.8, for example.

Figure 29:
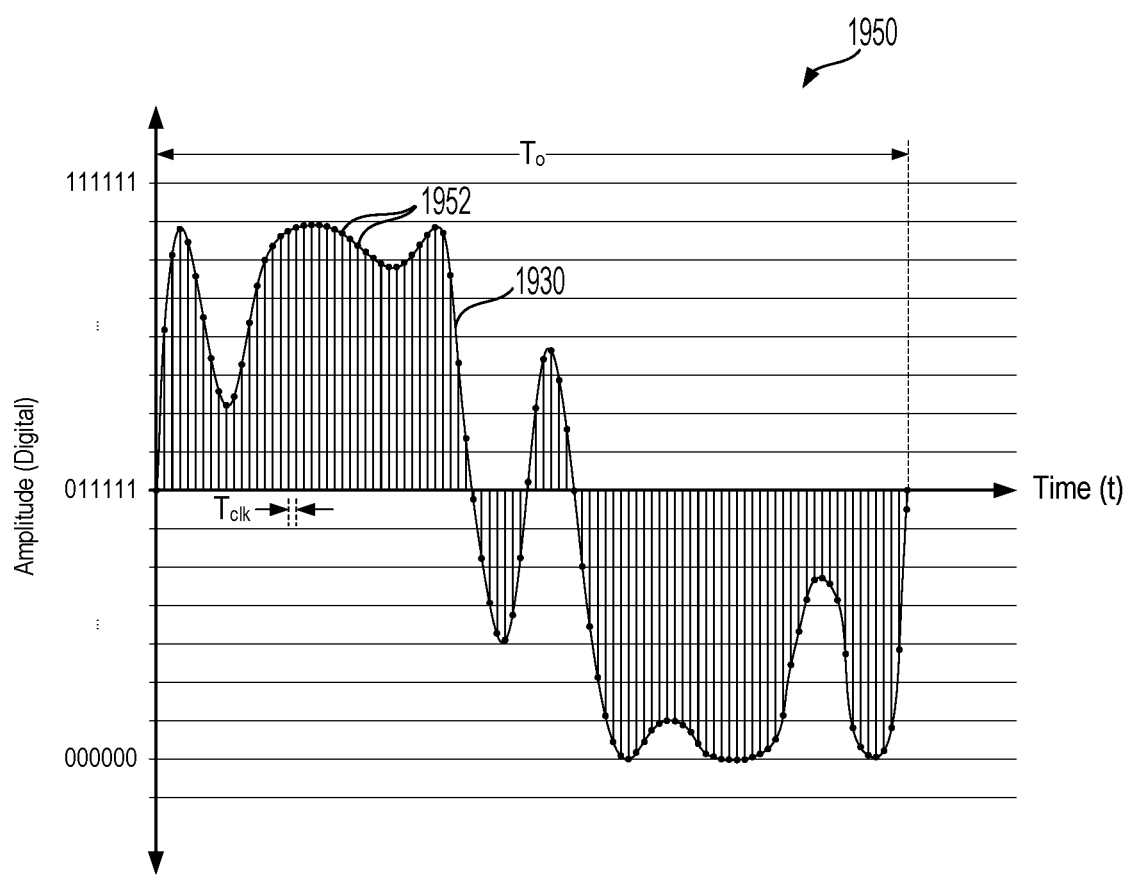
FIG. 29 illustrates one cycle of a digital electrical signal waveform shown in FIG. 27.

FIG. 29 illustrates one cycle of a digital electrical signal waveform 1950 of the analog waveform 1930 shown in FIG. 27. The horizontal axis represents Time (t) and the vertical axis represents digital phase points. The digital electrical signal waveform 1950 is a digital version of the desired analog waveform 1930 shown in FIG. 27, for example. The digital electrical signal waveform 1950 is generated by storing a phase point 1952 that represents the amplitude at each clock cycle $T_{clk}$ over one cycle or period $T_o$. The digital electrical signal waveform 1950 is generated over one period $T_o$ by any suitable digital processing circuit. The amplitude phase points are digital words stored in a memory circuit. In the example illustrated in FIG. 29, the digital word is a six-bit word that is capable of storing the amplitude phase points with a resolution of $2^6$ or 64 bits. It will be appreciated that the example shown in FIG. 29 is for illustrative purposes and in actual implementations the resolution can be much higher. The digital amplitude phase points 1952 over one cycle $T_o$ are stored in the memory as a string of string words in a lookup table 1304, 1410 as described in connection with FIGS. 13 and 14, for example. To generate the analog version of the waveform 1930, the amplitude phase points 1952 are read sequentially from the memory from 0 to $T_o$ at each clock cycle $T_{clk}$ and are converted by a DAC circuit 1308, 1412, also described in connection with FIGS. 13 and 14. Additional cycles can be generated by repeatedly reading the amplitude phase points 1952 of the digital electrical signal waveform 1950 the from 0 to $T_o$ for as many cycles or periods as may be desired. The smooth analog version of the waveform 1930 (also shown in FIG. 27) is achieved by filtering the output of the DAC circuit 1308, 1412 by a filter 1312, 1414 (FIGS. 13 and 14). The filtered output 1314, 1422 (FIGS. 13 and 14) is applied to the input of a power amplifier 212, 326, 426, 506 (FIGS. 5-8).

A variety of techniques can be used for compressing and/or limiting ultrasonic electrical signal waveforms. It should be noted that the integrity of an ultrasonic electrical signal waveform can be more important than the integrity of the RF electrical signal waveform as long as any low frequency components of the RF electrical signal waveform are limited to safe patient levels so as to avoid neuro-muscular stimulation. In another form, the frequency of an RF electrical signal waveform can be changed on a continuous basis in order to manage the peaks of the waveform. Waveform control is important as more complex RF waveforms, are implemented with the system.

The surgical instruments 104, 106, 108 described herein can include features to allow the energy being delivered by the generator 100 to be dynamically changed based on the type of tissue being treated by the end effector 122, 124, 125 of the surgical instrument 104, 106, 108 and various characteristics of the tissue. In one aspect, an algorithm for controlling the power output from a generator 100 that is delivered to the end effector 122, 124, 125 of the surgical instrument 104, 106, 108 can include an input that represents the tissue type to allow the energy profile from the generator 100 to be dynamically changed during the procedure based on the type of tissue being effected by the end effector 122, 124, 125 of the surgical instrument 104, 106, 108.

Figure 30:
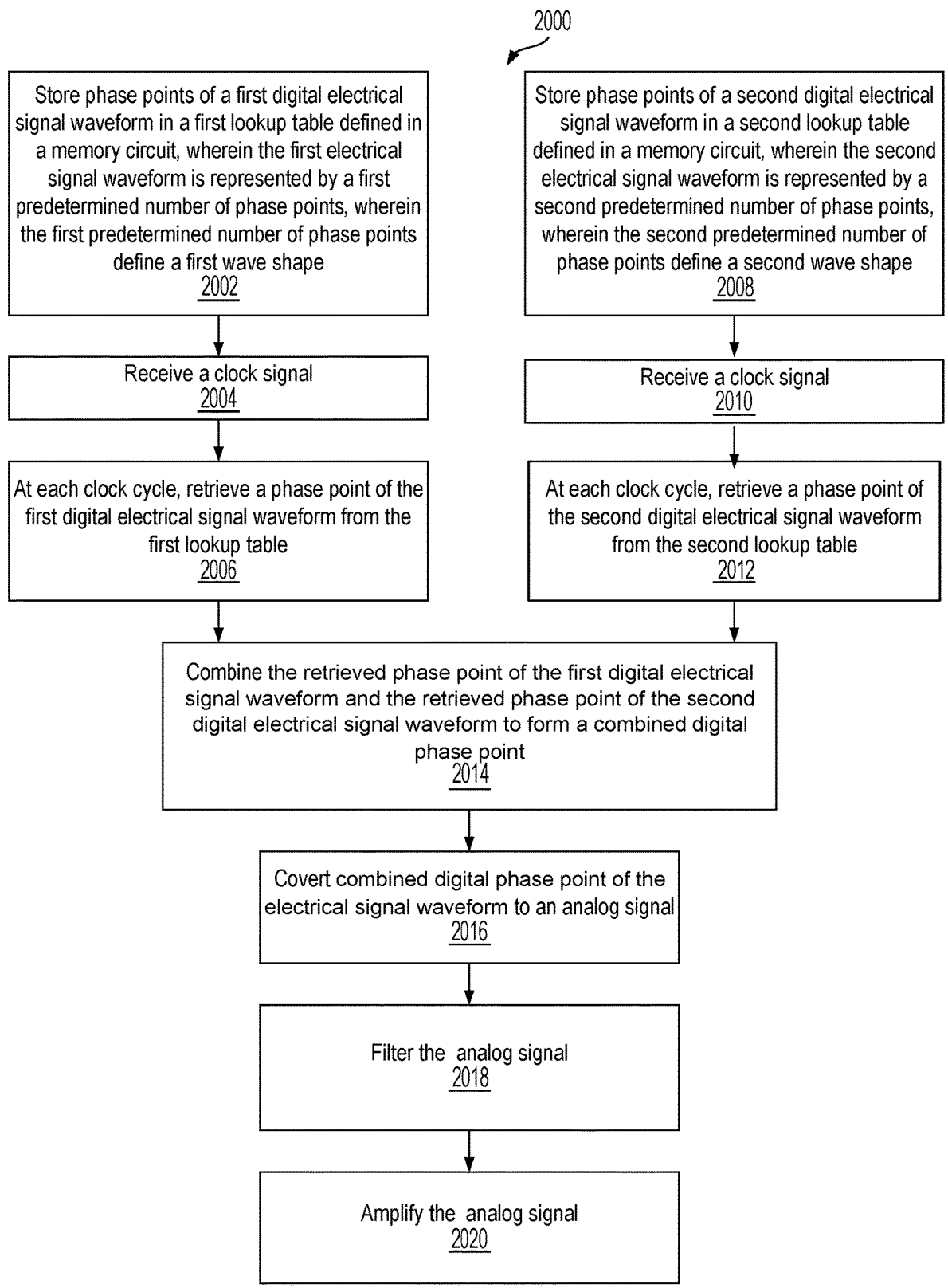
FIG. 30 is a logic flow diagram of a method of generating a digital electrical signal waveform according to one aspect.
Figure 31:
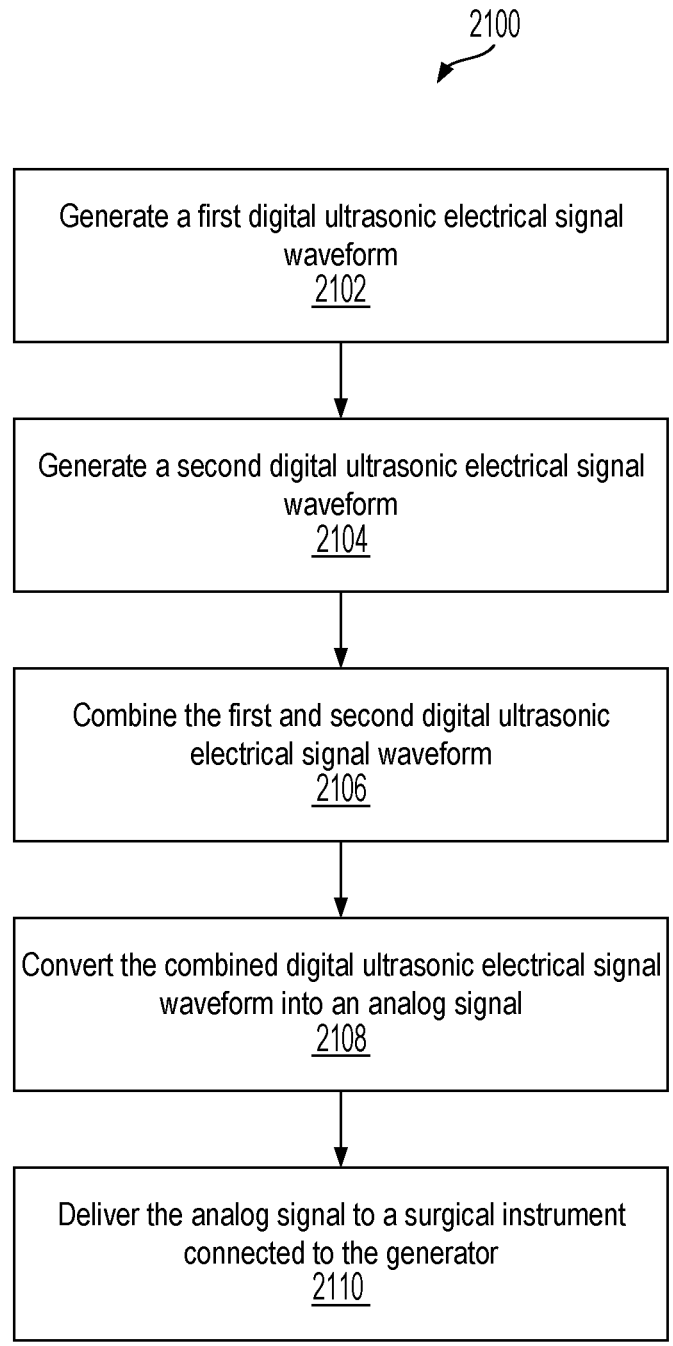
FIG. 31 is a logic flow diagram of a method of generating a digital electrical signal waveform according to one aspect.

FIGS. 30 and 31 are logic flow diagrams of methods 2000, 2100 of generating an electrical signal waveform by any of the generators 100, 200, 300, 400, 500, 9001, 1003, 1103, 1203 described herein. For conciseness and clarity the generators 100, 200, 300, 400, 500, 9001, 1003, 1103, 1203 will be referred to generally as the generator 100. The method 1500 will be described with reference to FIGS. 1, 13, 14, and 29 and FIGS. 5-8. In accordance with the methods 2000, 2100 described herein, the generator 100 is configured to generate one or more than one ultrasonic electrical signal waveform to drive the ultrasonic transducer 120 of at least two surgical instruments 104, 108 simultaneously or to drive two ultrasonic transducers 120 in one surgical instrument 104, 108 simultaneously. The surgical instruments 104, 108 may comprise instruments that operate the same modalities or different modalities of surgical treatment techniques. In one aspect, the surgical instruments 104, 108 comprise at least one ultrasonic transducer 120. Nevertheless, each surgical instrument 104, 108 may comprise multiple ultrasonic transducer 120. The ultrasonic transducer(s) 120 in each of the surgical instruments 104, 108 may be driven by a signal of different frequencies, voltages, and/or currents. For example, the ultrasonic transducer 120 of the ultrasonic surgical instrument 104 may be driven at a frequency of 55.5 kHz and the ultrasonic transducer 120 of the multifunction surgical instrument 108 may be driven at a frequency of 33 kHz. Generally, the ultrasonic transducer 120 can be driven at frequencies in excess of 20 kHz up to 100 kHz.

In accordance with the methods 2000, 2100, the generator 100 comprises a digital processing circuit, a DDS circuit 1300, 1400, a memory circuit defining a lookup table 1304, 1410, and DAC circuit 1308, 1412, as described herein. The digital processing circuit may comprise any digital processing circuit, microprocessor, microcontroller, digital signal processor, logic device comprising combinational logic or sequential logic circuits, or any suitable digital circuit. The memory circuit may be located either in the surgical instrument 104, 108 or the generator 100. In one aspect, the DDS circuit 1300, 1400 is coupled to the digital processing circuit and the memory circuit. In another aspect, the memory circuit is part of the DDS circuit 1300, 1400.

In various aspects, the generator 100 may be configured to drive multiple ultrasonic transducers 120 in one or more ultrasonic surgical instruments 104, 108 simultaneously. Thus the generator 100 may be configured to drive the surgical instruments 104, 108 in multiple vibration modes to achieve a longer active length at the ultrasonic blade 128, 149 and to create different tissue effects.

According to one of the present disclosure, the generator 100 may be configured to provide ultrasonic electrical signal waveforms defining a number of wave shapes to a surgical instrument 104, 108 so that the surgical instrument 104, 108 may apply a desired therapy to tissue at the end effector 122, 125.

In one aspect, the generator 100 may be configured to generate a digital electrical signal waveform such that the desired wave shape can be digitized by a number of phase points or samples which are stored in a lookup table 1304, 1410 defined in volatile or non-volatile memory as discussed above in connection with FIGS. 13 and 14, for example. The phase points or samples may be stored in the lookup table 1304, 1410 defined in a FPGA, for example. The wave shape may be digitized into a number of phase points or samples as shown in TABLE 1. In one aspect, the wave shape may be digitized into 1024 phase points, for example. The digital processing circuit of the generator 100 may control by software or digital control the FPGA to scan the addresses in the lookup table which in turn provides varying digital input values to the DAC circuit 1308, 1412 that feeds a power amplifier 1062, 422, 506. The addresses may be scanned according to a frequency of interest. Using such the lookup table 1304, 1410 enables generating various types of wave shapes that can be used to drive the ultrasonic transducers 120 of the surgical instruments 104, 108 simultaneously. Furthermore, multiple wave shape lookup tables 1304, 1410 can be created, stored, and applied to tissue for a single generator 100.

In one aspect, the electrical signal waveforms may be defined by an output current, an output voltage, an output power, or frequency suitable to drive the ultrasonic transducer 120 or multiple ultrasonic transducers (e.g. two or more ultrasonic transducers). In the case of the multifunction surgical instrument 108, in addition to driving the ultrasonic transducer 120, the electrical signal waveforms may be defined by an output current, an output voltage, an output power, or frequency suitable to drive the electrodes located in the end effector 125 of the multifunction surgical instrument 108.

Further, in one aspect where the surgical instrument 104, 108 comprises ultrasonic components, the electrical signal waveform may be configured to drive at least two vibration modes of the ultrasonic transducer 120. Accordingly, a generator 100 may be configured to provide a electrical signal waveform to at least one surgical instrument 104, 108 wherein the electrical signal waveform defines at least one wave shape selected out of a plurality of wave shapes stored in the lookup table 1304, 1410. Further, the electrical signal waveform provided to the two surgical instruments 104, 108 may define two or more wave shapes. The lookup table 1304, 1410 may comprise information associated with a plurality of wave shapes and the lookup table 1304, 1410 may be stored in a memory located either in the generator 100 or the surgical instruments 104, 108. In one embodiment or example, the lookup table 1304, 1410 may be a direct digital synthesis table, which may be stored in an FPGA located in the generator 100 or the surgical instruments 104, 108. The lookup table 1304, 1410 may be addressed using any suitable technique for categorizing wave shapes. According to one aspect, the DDS lookup table 1304, 1410 may be addressed according to the frequency of the electrical signal waveform. Additional information associated with the plurality of wave shapes also may be stored as digital information in the DDS lookup table 1304, 1410.

In one aspect, the generator 100 may comprise a DAC circuit 1308, 1412 and a power amplifier 1062, 422, 506. The DAC circuit 1308, 1412 is coupled to the power amplifier 212, 326, 426, 506 such that the DAC circuit 1308, 1412 provides the analog electrical signal waveform to a filter 1312, 1414 and the output of the filter 1312, 1414 is provided to the power amplifier 1062, 422, 506. The output of the power amplifier is provided to the surgical instrument 104, 108.

Further, in one aspect the generator 100 may be configured to provide the electrical signal waveform to at least two surgical instruments 104, 108 simultaneously. This may be accomplished through a single output port or channel of the generator 100. The generator 100 also may be configured to provide the electrical signal waveform, which may define two or more wave shapes, via a single output port or channel to the two surgical instruments 104, 108 simultaneously. The analog signal output of the generator 100 may define multiple wave shapes to one or more than one surgical instruments 104, 108. For example, in one aspect, the electrical signal waveform comprises multiple ultrasonic drive signals. In another aspect, the electrical signal waveform comprises multiple ultrasonic drive signals and one or more than one RF signals. Accordingly, an electrical signal waveform output of the generator 100 may comprise multiple ultrasonic drive signals, multiple RF signals, and/or a combination of multiple ultrasonic drive signals and a RF signals.

In one aspect, the generator 100 as described herein may allow for the creation of various types of direct digital synthesis lookup tables 1304, 1410 within an FPGA located in the generator 100. Some examples of the wave shapes that may be produced by the generator 100 include high crest factor signals (which may be used for surface coagulation), low crest factor signals (which may be used for deeper tissue penetration), and electrical signal waveforms that promote efficient touch-up coagulation. The generator 100 also may create multiple wave shape lookup tables 1304, 1410. The generator 100 can be configured to switch between different electrical signal waveforms for driving ultrasonic transducers 120 during a procedure (e.g., "on-the-fly" or in virtual real time based on user or sensor inputs) based on desired tissue effects or feedback signals associated with the state of the tissue located in the end effector 122, 125. Switching may be based on tissue impedance, tissue temperature, state of coagulation, state of dissection, and/or other factors.

In one aspect, the generator 100 as described herein also may provide, in addition to the traditional sine wave shape, wave shapes that maximizes the power into tissue per cycle (i.e. trapezoidal, square, or triangular wave shapes). It also may provide wave shapes that are synchronized in a manner that would maximize power delivery in the case of an electrical signal waveform comprises RF and ultrasonic signal components to drive ultrasonic and RF therapeutic energy simultaneously while maintaining ultrasonic frequency lock. Further, custom wave shapes specific to various types of surgical instruments 104, 108 and their tissue effects can be stored in a lookup table 1304, 1410 memory located in the generator 100 or the surgical instrument 104, 108, where the memory may be a volatile (RAM) or non-volatile (EEPROM) memory. The wave shape may be fetched from the lookup table 1304, 1410 memory upon connecting the surgical instrument 104, 108 to the generator 100.

With reference to FIG. 30, in accordance with the method 2000, the digital processing circuit instructs the DDS circuit 1300, 1400 to store 2002 a first digital electrical signal waveform in a first lookup table 1304, 1410 defined in the memory circuit. The first digital electrical signal waveform is represented by a first predetermined number of phase points or samples that are stored in the first lookup table 1304, 1410. The first predetermined number of phase points define a first wave shape. The DDS circuit 1300, 1400 receives 2004 a clock signal. At each clock cycle, the DDS circuit 1300, 1400 retrieves 1506 a phase point from the first lookup table 1304, 1410. In one aspect, the first digital electrical signal waveform is a digital version of a first ultrasonic electrical signal waveform.

Further, in accordance with the method 2000, the digital processing circuit also instructs the DDS circuit 1300, 1400 to store 2008 a second digital electrical signal waveform in a second lookup table 1304, 1410 defined in the memory circuit, or other memory circuit. The second digital electrical signal waveform is represented by a second predetermined number of phase points that are stored in the second lookup table 1304, 1410. The second predetermined number of phase points define a second wave shape. The DDS circuit 1300, 1400 receives 2010 a clock signal. At each clock cycle, the DDS circuit 1300, 1400 retrieves 2012 a phase point from the second lookup table 1304, 1410. In one aspect, the second digital electrical signal waveform represents a second ultrasonic electrical signal waveform.

The digital signal processing circuit combines 2014 the retrieved phase point of the first digital electrical signal waveform and the retrieved phase point of the second digital electrical signal waveform to form a combined digital phase point. The combined digital phase point of the electrical signal waveform is converted 2016 by a DAC circuit 1308, 1412 to a combined analog signal. The analog signal 1310, 1420 output of the DAC circuit 1308, 1412 is filtered 2018 by a filter 1312, 1414 and is amplified 2020 by a power amplifier 212, 326, 426, 506 before the combined analog electrical signal waveform is provided to a surgical instrument 104, 108 connected to the generator 100. The first and second digital electrical signal waveforms may be combined in a way, for example using an appropriate algorithm, which is specifically designed to provide a proper input to a surgical instrument 104, 108. This may include limiting peaks of the combined digital electrical signal waveform so that the surgical instrument 104, 108 and/or components of the generator 100 are not damaged. Damage is one consequence of overdriving the components, however, another consequence is undesired wave shapes that can affect the ultrasonic transducer 120 or cause undesired output, such as unintended frequency components, on the RF poles. Accordingly, in one aspect, the output components are not damaged but are operating in a non-linear fashion and produce undesirable wave shapes, distortions, or harmonic components that could affect the operation of the ultrasonic transducer 120 or be delivered to tissue through the RF electrodes.

In one aspect, the combined analog electrical signal waveform is configured to drive a plurality of ultrasonic transducers 120, either simultaneously or sequentially. In another aspect, the combined analog electrical signal waveform is configured to drive a plurality of ultrasonic operational modes of an ultrasonic surgical instrument 104, 108. In one aspect, the ultrasonic surgical instrument 104, 108 comprises an ultrasonic transducer 120 and an ultrasonic blade 128, 149. The combined analog electrical signal waveform may be configured to drive the ultrasonic transducer 120 to produce a predetermined active length of the ultrasonic blade 128, 149. In one aspect, the combined analog electrical signal waveform may be configured to drive the ultrasonic transducer 120 to produce a predetermined tissue effect by the ultrasonic blade 128, 149.

In one aspect, the first and second digital electrical signal waveforms represent first and second digital ultrasonic electrical signal waveforms and the method 2000 further comprises combining a RF electrical signal waveform with the first and second ultrasonic electrical signal waveforms.

In one aspect, the digital processing circuit stores phase points of a digital electrical signal waveform in the lookup table 1304, 1410 defined by the memory circuit. The digital processing circuit stores phase points of multiple digital electrical signal waveforms in corresponding multiple lookup tables 1304, 1410 defined by the memory circuit or other memory circuits. Each of the digital electrical signal waveforms is represented by a predetermined number of phase points. Each of the predetermined number of phase points defines a different wave shape.

In one aspect, the digital processing circuit receives a feedback signal associated with tissue parameters and modifying the predetermined wave shape according to the feedback signal.

In one aspect, the digital electrical signal waveform represents a combination of two waveforms having different amplitudes. In one aspect, the digital electrical signal waveform represents a combination of two waveforms having different frequencies. In one aspect, the digital electrical signal waveform represents a combination of two waveforms having of different amplitudes. In one aspect, the wave shape is a trapezoid, a sine or cosine wave, a square wave, a triangle wave, or any combinations thereof. In one aspect, the combined digital signal waveform is configured to maintain a predetermined ultrasonic frequency. In one aspect, the combined digital signal waveform is configured to deliver maximum power output.

With reference to FIG. 31, in accordance with the method 2100, the generator 100 generate 2102 a first digital ultrasonic electrical signal waveform, generates 2104 a second digital ultrasonic electrical signal waveform, and combines 2106 the first and second digital ultrasonic electrical signal waveforms. The DAC circuit 1308, 1412 converts 2108 the combined digital ultrasonic electrical signal waveform into an analog signal. The analog signal is delivered 2110 to a surgical instrument 104, 108 connected to the generator 100. The ultrasonic electrical signal waveform is configured to apply voltage, current, or power associated to an ultrasonic transducer 120 of a surgical instrument 104, 108 configured to receive the ultrasonic electrical signal waveform. In one aspect, each of the surgical instruments 104, 108 may comprise a plurality of ultrasonic transducers 120.

A digitized ultrasonic electrical signal waveform, including a combined digital ultrasonic electrical signal waveform may be stored in a memory circuit defining a lookup table 1304, 1410 located either in the generator 100 or the surgical instrument 104, 106. The lookup table 1304, 1410 may be a direct digital synthesis table, located in the generator 100. The ultrasonic electrical signal waveform(s) and/or the combined ultrasonic electrical signal waveform(s) may consist of a plurality of phase points or samples stored in the memory circuit. In order for the generator 100 to output an analog ultrasonic electrical signal waveform made by combining two or more ultrasonic electrical signal waveforms, or other ultrasonic electrical signal waveform, the phase points are retrieved from the memory circuit by a digital processing circuit associated with the generator 100 or the surgical instrument 104, 108. As previously discussed, the phase points define the digital combined ultrasonic electrical signal waveform. The phase points are retrieved from the memory circuit upon connection of the surgical instrument 104, 108 to the generator 100. The phase points or digital samples may comprise at least 1,024 phase points. In other aspects the digital samples may comprise any number of phase points as shown in TABLE 1. Further, the analog version of the combined ultrasonic electrical signal waveform may be output to a surgical instrument 104, 108 via a single port of the generator 100 through which the surgical instrument 104, 108 is connected to the generator 100.

In one aspect, the generator 100, as described herein, may be a single port or multiple port system and may include an output transformer with multiple taps to provide the power in the form that is required for the treatment. In one aspect, the form may be higher voltage and lower current, in order to drive an ultrasonic transducer 120. In another aspect, the form may be lower voltage and higher current to drive vessel sealing electrodes. Or it may be a coagulation or type waveform for touch-up or spot coagulation.

In addition, the generator 100 may comprise a FPGA. The generator 100 may be configured to scan, via the FPGA, a lookup table 1304, 1410 comprising samples the digital electrical signal waveform, retrieve, via the FPGA, the stored phase points from the lookup table 1304, 1410, and provide the phase points to a DAC circuit 1308, 1412. The analog signal 1310, 1420 output of the DAC circuit 1308, 1412 is filtered by a filter 1312, 1414, and amplified by a power amplifier 1062, 422, 506. The amplified analog ultrasonic electrical signal waveform is then output from the generator 100 to the surgical instrument 104, 108.

The analog ultrasonic electrical signal waveform may be configured for a particular treatment modality of the surgical instrument 104, 108 connected to the generator 100. Accordingly, the ultrasonic electrical signal waveform may be a single or composite ultrasonic electrical signal waveform. In one aspect, the ultrasonic electrical signal waveform or the composite ultrasonic electrical signal waveform may be combined with a RF waveform, which may be provided to at least two surgical instruments 104, 108 simultaneously. The surgical instruments 104, 108 may comprise instruments that operate in the same modalities or different modalities of surgical treatment techniques. In one aspect, the surgical instruments 104, 108 include at least one ultrasonic surgical instrument 104 and at least one combination RF electrosurgical/ultrasonic surgical instrument. The electrical signal waveform also may be a combined RF and ultrasonic electrical signal waveform configured to maintain a predetermined ultrasonic frequency. In one aspect, the predetermined ultrasonic frequency is frequency locked when the surgical instrument 104, 108 is connected to the generator 100. In another aspect, the combined RF and ultrasonic electrical signal waveform is configured to cause the surgical instrument 104, 108 to deliver maximum power to the tissue engaged in the end effector 122, 125 of the surgical instrument 104, 108. The maximum power application may be based on the maximum power output of a treatment modality of a surgical instrument 104, 108, such as, for example, an RF modality and/or an ultrasonic modality. According to further aspects, the electrical signal waveform may comprise a high crest factor signal, a low crest factor signal, or a combination thereof and/or the electrical signal waveform may comprise a sine wave shape, a trapezoidal wave shape, a square wave shape, a triangular wave shape, or a combination thereof. The electrical signal waveform also may be configured to provide a desired tissue effect or outcome to tissue engaged by the end effector 122, 125 of the surgical instrument 104, 108 when the electrical signal waveform is received by the surgical instrument 104, 108. In one aspect, the desired tissue effect is at least one of cutting, coagulation, and/or sealing.

The generator 100 also may be configured to switch between a first electrical signal waveform and a second electrical signal waveform based on predetermined criteria, such as, for example, a desired tissue effect and/or feedback from a surgical instrument 104, 108, which may include measured values of a tissue parameter. The tissue parameter may include a tissue type, a tissue amount, a tissue state, or a combination thereof. Accordingly, the methods described above also may include delivering the first electrical signal waveform and the second electrical signal waveform based on a desired tissue effect, tissue parameter, and/or other parameters associated with a surgical instrument 104, 108 connected to the generator 100.

Additionally, the first and second digital electrical signal waveforms stored in the generator 100 may be received by the generator 100 from a surgical instrument 104, 108 connected to the generator 100. The generator 100 may receive the first and second digital electrical signal waveforms following or upon connecting the surgical instrument 104, 108 to the generator 100. The samples of the first and second digital electrical signal waveforms may be stored in an EEPROM of the surgical instrument 104, 108, which is operable coupled to the generator 100 upon connection of the surgical instrument 104, 108 to the generator 100.

Figure 32:
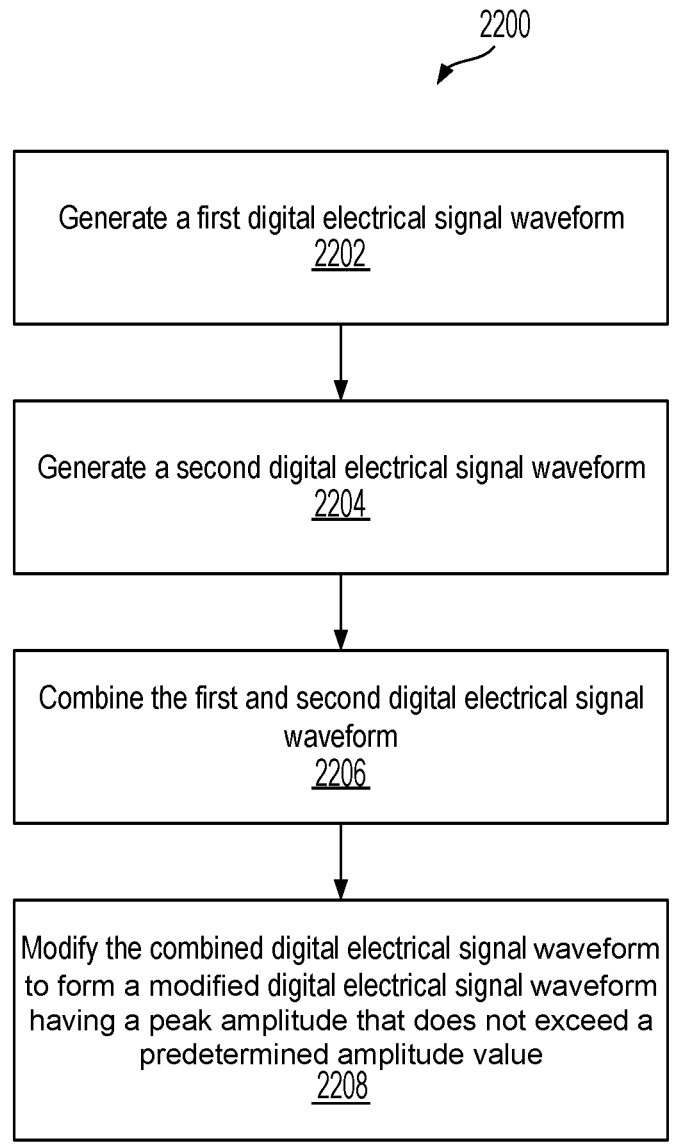
FIG. 32 is a logic flow diagram of a method of generating an electrical signal waveform configured to drive a surgical instrument and to protect output components of a generator according to one aspect.

FIGS. 32-34 are logic flow diagrams of methods 2200, 2300, 2400 of generating an electrical signal waveform configured to drive surgical instruments and to protect output components of any of the generators 100, 200, 300, 400, 500, 9001, 1003, 1103, 1203 described herein. For conciseness and clarity, the generators 100, 200, 300, 400, 500, 9001, 1003, 1103, 1203 will be referred to as the generator 100. Accordingly, the generator 100 is representative of the generators 200, 300, 400, 500, 9001, 1003, 1103, 1203 described herein. The method 1500 will be described with reference to FIGS. 1, 13, 14, and 20 and with reference to the generator circuits described in connection with FIGS. 5-8. The generator 100 comprises a digital processing circuit, a DDS circuit 1300, 1400, a memory circuit defining a lookup table 1304, 1410, and DAC circuit 1308, 1412, as described herein. The digital processing circuit may comprise any digital processing circuit, microprocessor, microcontroller, digital signal processor, logic device comprising combinational logic or sequential logic circuits, or any suitable digital circuit. The memory circuit may be located either in the surgical instrument 104, 106, 108 or the generator 100. In one aspect, the DDS circuit 1300, 1400 is coupled to the digital processing circuit and the memory circuit. In another aspect, the memory circuit is part of the DDS circuit 1300, 1400.

In accordance with the methods 2200, 2300, 2400 the digital processing circuit instructs the DDS circuit 1300, 1400 to store phase points or samples that define a digital electrical signal waveform in a lookup table 1304, 1410 defined in the memory circuit. The digital electrical signal waveform is represented by a predetermined number of phase points that are stored in the lookup table 1304, 1410. The predetermined number of phase points define a predetermined wave shape. The DDS circuit 1300, 1400 receives a clock signal. At each clock cycle, the DDS circuit 1300, 1400 retrieves a phase point from the lookup table 1304, 1410 and provides the phase point (e.g., sample) to the DAC circuit 1308, 1412. The DAC circuit 1308, 1412 converts the phase point of the digital electrical signal waveform into an analog electrical signal output (e.g., a sample/hold output of the DAC circuit 1308, 1412). The analog sample/hold output of the DAC circuit 1308, 1412 is filtered by the filter 1312, 1414 and amplified by a power amplifier 212, 326, 426, 506 (FIGS. 5-8), for example, before the analog electrical signal waveform is provided to the surgical instrument 104, 106, 108.

The one or more than one digital electrical signal waveforms may be generated from a one or more than one lookup tables 1304, 1410 as described in connection with FIGS. 13 and 14. The one or more than one digital electrical signal waveform may be defined by a plurality of wave shapes that are combined to form a complex waveform. The lookup tables 1304, 1410 may be defined in a memory circuit in communication with a digital processing circuit of the generator 100 or the surgical instrument 104, 106, 108. In one aspect, the lookup tables 1304, 1410 may be DDS lookup tables that can be addressed according to a desired frequency of the electrical signal waveforms. In one aspect, the digital electrical signal waveform is a combination of at least two wave shapes. The combined digital electrical signal waveform is provided to the DAC circuit 1308, 1410 and may be filtered by the filter 1312, 1414 and amplified by a power amplifier. The combined analog electrical signal waveform may be an ultrasonic drive signal having a frequency of 55 kHz or an RF signal having a frequency of 330 kHz or a combination of the ultrasonic drive signal and the RF signal.

Additionally, digital phase points of the digital electrical signal waveform may be received by the generator 100 from a surgical instrument 104, 106, 108 connected to the generator 100. The generator 100 may receive the phase points following or upon connection of the surgical instrument 104, 106, 108 to the generator 100. The phase points of the digital electrical signal waveform may be stored in an EEPROM of the surgical instrument 104, 106, 108, which is operable coupled to the generator 100 upon connection of the surgical instrument 104, 106, 108 to the generator 100.

According to various aspects, the electrical signal waveform also may be provided to at least two surgical instruments 104, 106, 108 simultaneously. The surgical instruments 104, 106, 108 may comprise instruments that operate the same modalities or different modalities of surgical treatment techniques. In one aspect, the surgical instruments include at least one ultrasonic surgical instrument and at least one RF surgical instrument.

In various aspects, the electrical signal waveforms may represent electrical signals having different wave shapes. In one aspect, the electrical signal waveforms may represent ultrasonic signals suitable for driving ultrasonic transducers 120 of an ultrasonic surgical instrument 104, RF signals suitable for driving an electrode of an electrosurgical instrument 106 or a multifunction surgical instrument 108. A plurality of the electrical signal waveforms can be delivered separately, simultaneously, individually, or combined in one signal.

With reference now to FIG. 32, in accordance with the method 2200, the generator 100 is configured to generate 2202 a first digital electrical signal waveform, generate 2204 a second digital electrical signal waveform, combine 2206 the first and second digital electrical signal waveform, and modify 2208 the combined digital electrical signal waveform to form a modified digital electrical signal waveform. A peak amplitude of the modified digital electrical signal waveform is configured not to exceed a predetermined value such that the amplitude remains within the normal operating rating of the amplifier 212, 326, 426, 506 and other output components of the generator 100. The modified digital electrical signal waveform is converted to an analog electrical signal waveform by the DAC circuit 1308, 1412, which is then applied to the amplifier 212, 326, 426, 506 and other output components of the generator 100. The analog electrical signal waveform is delivered to at least one surgical instrument 104, 106, 108 connected to the generator 100. The first digital electrical signal waveform and/or the second digital electrical signal waveform may be extractable from the combined digital electrical signal waveform. Further, either the first or the second digital electrical signal waveform may comprise an arbitrary function, a sine wave function, a square wave function, a triangular function, which are extractable from the combined digital electrical signal waveform. In one aspect, the second digital electrical signal waveform is an RF waveform and/or the first digital electrical signal waveform is an ultrasonic waveform.

The first digital electrical signal waveform may include a RF drive signal and the second digital electrical signal waveform may include an ultrasonic drive signal. The first and/or the second digital electrical signal waveform may be generated via the DDS circuit 1300, 1400 of the generator 100. In one aspect, the method 1500 further comprises determining that the peak maximum amplitude of the combined digital electrical signal waveform is approaching as the combined digital electrical signal waveform is being delivered or transmitted to the surgical instrument 104, 106, 108. In another aspect, the method 2200 further comprises determining a peak amplitude of the combined digital electrical signal waveform and modifying the combined digital electrical signal waveform based on the peak amplitude of the combined waveform. In addition, the generator 100 may be configured to modify the combined digital electrical signal waveform by reducing the amplitude of the combined digital electrical signal waveform upon determining that the peak amplitude of the combined digital electrical signal waveform is approaching during transmission or delivery of the analog electrical signal waveform to the surgical instrument 104, 106, 108.

With reference now to FIG. 33, in accordance with the method 2300, the generator 100 is configured to generate 2302 a first digital electrical signal waveform, generate 2304 a second digital electrical signal waveform, where the second digital electrical signal waveform is a function of the first digital electrical signal waveform. The generator 100 is configured to combine 2306 the first digital electrical signal waveform and the second digital electrical signal waveform to form a combined digital electrical signal waveform. The peak amplitude of the combined digital electrical signal waveform is configured not to exceed a predetermined value such that the amplitude remains within the normal operating rating of the amplifier 212, 326, 426, 506 and other output components of the generator 100. The generator 100 is configured to deliver 2308 the combined digital electrical signal waveform to at least one surgical instrument 104, 106, 108 connected to the generator 100. The first digital electrical signal waveform and/or the second digital electrical signal waveform may be extractable from the combined digital electrical signal waveform. Further, either the first or the second digital electrical signal waveform may comprise an arbitrary function, a sine wave function, a square wave function, a triangular function, which are extractable from the combined digital electrical signal waveform. In one aspect, the second digital electrical signal waveform is an RF waveform and/or the first digital electrical signal waveform is an ultrasonic waveform.

With reference now to FIG. 34, in accordance with the method 2400, the generator 100 is configured to generate 2402 a first digital electrical signal waveform, generate 2404 a second digital electrical signal waveform, where the second digital electrical signal waveform is a function of the first digital electrical signal waveform. The generator 100 is configured to modify 2404 a frequency of the first digital electrical signal waveform to form a frequency modified first digital electrical signal waveform. The generator 100 is configured to combine 2406 the frequency modified first digital electrical signal waveform and the second digital electrical signal waveform to form a combined digital electrical signal waveform. The generator 100 is configured to deliver 2408 the combined digital electrical signal waveform to at least one surgical instrument 104, 106, 108 connected to the generator 100. The combined digital electrical signal waveform may be configured such that a peak amplitude of the combined waveform does not exceed a predetermined value such that amplitude remains within the safe operating rating of the amplifier 212, 326, 426, 506 and other output components of the generator 100. The first digital electrical signal waveform and/or the second digital electrical signal waveform may be extractable from the combined digital electrical signal waveform. Further, either the first or the second digital electrical signal waveform may comprise an arbitrary function, a sine wave function, a square wave function, a triangular function, which are extractable from the combined digital electrical signal waveform. In one aspect, the second digital electrical signal waveform is an RF waveform and/or the first digital electrical signal waveform is an ultrasonic waveform.

In various aspects, the first and second electrical signal waveforms may represent electrical signals having different wave shapes. In one aspect, the first digital electrical signal waveform may represent an RF signal suitable for driving an electrode of an RF electrosurgical instrument 106 or a multifunction surgical instrument 108 and the second electrical signal waveform may represent an ultrasonic signal for driving an ultrasonic transducer of an ultrasonic surgical instrument 104 or a multifunction surgical instrument 108. The first and second electrical signal waveforms can be delivered separately, simultaneously, individually, or combined in one signal.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Aspects of the present disclosure have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, titled ROBOTIC SURGICAL TOOL WITH ULTRASOUND CAUTERIZING AND CUTTING INSTRUMENT, published Aug. 31, 2004, the disclosure of which is incorporated by reference herein.

Aspects of the devices disclosed herein can be designed to be disposed of after a single use, or they can be designed to be used multiple times. Various aspects may, in either or both cases, be reconditioned for reuse after at least one use. Reconditioning may include any combination of the steps of disassembly of the device, followed by cleaning or replacement of particular pieces, and subsequent reassembly. In particular, aspects of the device may be disassembled, and any number of the particular pieces or parts of the device may be selectively replaced or removed in any combination. Upon cleaning and/or replacement of particular parts, aspects of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various aspects of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, the examples, aspects, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

While various details have been set forth in the foregoing description, it will be appreciated that the various aspects of the techniques for operating a generator for digitally generating electrical signal waveforms and surgical instruments may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered clauses:

1. An apparatus comprising a generator configured to provide an electrical signal waveform to at least one surgical instrument; a table comprising information associated with a plurality of wave shapes; and wherein the electrical signal waveform corresponds to at least one wave shape of the plurality of wave shapes of the table.

2. The apparatus of clause 1, wherein the table is stored within the generator.

3. The apparatus of clauses 1 or 2, wherein the table is a direct digital synthesis table.

4. The apparatus of clause 3, wherein the direct digital synthesis table is addressed according to a frequency of the electrical signal waveform.

5. The apparatus of any of clauses 1-4, wherein the information associated with the plurality of wave shapes is stored as digital information.

6. The apparatus of any of clauses 1-5, wherein the generator comprises a DAC circuit and a power amplifier, and wherein the DAC circuit is coupled to the power amplifier and the DAC circuit provides digital input values to the power amplifier associated with a wave shape of the plurality of wave shapes for the electrical signal waveform.

7. The apparatus of any of clauses 1-6, wherein the generator is configured to provide the electrical signal waveform to at least two surgical instruments simultaneously.

8. The apparatus of clause 7, wherein the electrical signal waveform provided to the at least two surgical instruments comprises at least two wave shapes.

9. The apparatus of clause 8, wherein the generator is configured to provide the electrical signal waveform that comprises the at least two wave shapes via a single output channel.

10. The apparatus of any of clauses 1-9, wherein the electrical signal waveform comprises an ultrasonic signal.

11. The apparatus of clause 10, wherein the electrical signal waveform is configured to control at least one of an output current, an output voltage, or an output power of an ultrasonic transducer.

12. The apparatus of clause 10 or 11, wherein the electrical signal waveform is configured to drive at least two vibration modes of an ultrasonic transducer of the at least one surgical instrument.

13. The apparatus of any of clauses 1-12, wherein the generator is configured to provide the electrical signal waveform to at least two surgical instruments simultaneously, wherein the electrical signal waveform comprises an ultrasonic signal and an RF signal.

14. A method of operating a generator, comprising: generating an electrical signal waveform; providing the generated electrical signal waveform to at least one surgical instrument; and wherein generating the electrical signal waveform comprises reading electrical signal waveform information from a table comprising information associated with a plurality of wave shapes; and wherein the generated electrical signal waveform corresponds to at least one wave shape of the plurality of wave shapes of the table.

15. The method of clause 14, wherein the generated electrical signal waveform corresponds to at least two wave shapes of the plurality of wave shapes of the table.

16. The method of clause 14 or 15, wherein the electrical signal waveform comprises an ultrasonic signal.

17. The method of any of clauses 14-16, wherein providing the generated electrical signal waveform to the at least one surgical instrument comprises providing the electrical signal waveform to at least two surgical instruments simultaneously.

18. The method of clause 17, wherein the at least two surgical instruments comprise at least one ultrasonic surgical instrument and at least one RF surgical instrument.

19. The method of clauses 14-18, wherein providing the generated electrical signal waveform comprises providing the generated waveform via a single output channel.

20. The method of clauses 14-19, wherein the table is a direct digital synthesis table that is addressed according to a frequency of the electrical signal waveform.

21. An apparatus for operating a surgical instrument, comprising: at least one surgical instrument configured to receive an electrical signal waveform from a generator; wherein the electrical signal waveform corresponds to at least one wave shape of a plurality of wave shapes stored in a table of the generator.

22. The apparatus of clause 21, wherein the at least one surgical instrument comprises at least two surgical instruments that receive the electrical signal waveform simultaneously.

23. The apparatus of clause 22, wherein the electrical signal waveform provided to the at least two surgical instruments comprises at least two wave shapes.

24. The apparatus of clause 22 or 23, wherein each of the at least two surgical instruments receive the electrical signal waveform from a single output channel of the generator.

25. The apparatus of any one of clauses 22-24, wherein one of the at least two surgical instruments comprises an ultrasonic surgical component and wherein another of the at least two surgical instruments comprises an RF surgical component.

26. The apparatus of any one of clauses 21-25, wherein the electrical signal waveform comprises a ultrasonic signal.

27. The apparatus of any of clauses 21-26, wherein the electrical signal waveform is configured to control at least one of an output current, an output voltage, or an output power of an ultrasonic transducer of the at least one surgical instrument.

28. The apparatus of any one of clauses 21-27, wherein the electrical signal waveform is configured to drive at least two vibration modes of an ultrasonic transducer of the at least one surgical instrument.

29. The apparatus of any one of clauses 21-28, wherein the generator is configured to provide the electrical signal waveform to at least two surgical instruments simultaneously.

30. A method of generating electrical signal waveforms by a generator, the generator comprising a digital processing circuit, a memory circuit in communication with the digital processing circuit, a digital synthesis circuit in communication with the digital processing circuit and the memory circuit, and a digital-to-analog converter (DAC) circuit, the memory circuit defining a lookup table, the method comprising: storing, by the digital processing circuit, phase points of a digital electrical signal waveform in the lookup table defined by the memory circuit, wherein the digital electrical signal waveform is represented by a predetermined number of phase points, wherein the predetermined number phase points define a predetermined wave shape; receiving a clock signal by the digital synthesis circuit, and at each clock cycle: retrieving, by the digital processing circuit, a phase point from the lookup table; and converting, by the DAC circuit, the retrieved phase point to an analog signal.

31. The method of clause 30, comprising amplifying, by an amplifier, the analog signal from an output of the DAC circuit.

32. The method of any one of clause 30 or 31, wherein storing, by the digital processing circuit, phase points of a digital electrical signal waveform in the lookup table defined by the memory circuit, comprises: storing, by the digital processing circuit, phase points of multiple digital electrical signal waveforms in corresponding multiple lookup tables defined by the memory circuit or other memory circuits, wherein each of the digital electrical signal waveforms is represented by a predetermined number of phase points, and wherein each of the predetermined number of phase points defines a different wave shape.

33. The method of any one of clauses 30-32, comprising: receiving, by the digital processing circuit, a feedback signal associated with tissue parameters; and modifying the predetermined wave shape according to the feedback signal.

34. The method of any one of clauses 30-33, wherein the digital electrical signal waveform represents a RF signal waveform, an ultrasonic signal waveform, or a combination thereof.

35. The method of any one of clauses 30-34, wherein the digital electrical signal waveform represents a combination of two waveforms having different amplitudes.

36. The method of any one of clauses 30-35, wherein the digital electrical signal waveform represents a combination of two waveforms having different frequencies.

37. The method of clause 36, wherein the digital electrical signal waveform represents a combination of two waveforms having of different amplitudes.

38. The method of any one of clauses 30-37, wherein the predetermined wave shape is a trapezoid, a sine or cosine wave, a square wave, a triangle wave, or any combinations thereof.

39. The method of any one of clauses 30-38, wherein the digital electrical signal waveform is a combined RF and ultrasonic signal waveform configured to maintain a predetermined ultrasonic frequency.

40. The method of any one of clauses 30-39, wherein the first is a combined RF and ultrasonic waveform configured to deliver maximum power output.

41. A method of generating electrical signal waveforms by a generator, the generator comprising a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; receiving, by the digital synthesis circuit, a clock signal, and at each clock cycle: retrieving, by the digital synthesis circuit, a phase point from the first lookup table; retrieving, by the digital synthesis circuit, a phase point from the second lookup table; and determining, by the digital processing circuit, whether to switch between the phase points of the first and second electrical signal waveforms or to synchronize the phase points of the first and second electrical signal waveforms.

42. The method of clause 41, comprising receiving, by the digital processing circuit, a feedback signal associated with tissue parameters.

43. The method of clause 42, comprising: switching between the phase point of the first digital electrical signal waveform and the phase point of the second digital electrical signal waveform; and converting, by the DAC circuit, the retrieved phase point.

44. The method of clause 42, comprising: synchronizing the phase points of the first and second digital electrical signal waveforms to maximize power delivery per cycle; and converting, by the DAC circuit, the synchronized phase points.

45. The method of any one of clauses 41-44, wherein the first digital electrical signal waveform represents a RF waveform and the second digital electrical signal waveform represents an ultrasonic signal waveform.

46. A generator for generating electrical signal waveforms, the generator comprising: a digital processing circuit; a memory circuit in communication with the digital processing circuit, the memory circuit defining a lookup table; a digital synthesis circuit in communication with the digital processing circuit and the memory circuit, the digital synthesis circuit receiving a clock signal; and a digital-to-analog converter (DAC) circuit; the digital processing circuit configured to store phase points of a digital electrical signal waveform in the lookup table defined by the memory circuit, wherein the digital electrical signal waveform is represented by a predetermined number of phase points, wherein the predetermined number phase points define a predetermined wave shape; and retrieve a phase point from the lookup table at each clock cycle; and the DAC circuit configured to convert the retrieved phase point to an analog signal.

47. The generator of clause 46, comprising an amplifier coupled to the DAC circuit.

48. The generator of clause 46 or 47, wherein the digital synthesis circuit is a direct digital synthesis (DDS) circuit.

49. The generator of any one of clauses 46-48, comprising a filter coupled to the output of the DAC circuit.

50. A method of generating electrical signal waveforms by a generator, the generator comprising a digital processing circuit, a memory circuit in communication with the digital processing circuit, the memory circuit defining first and second lookup tables, a digital synthesis circuit in communication with the digital processing circuit and the memory circuit, and a digital-to-analog converter (DAC) circuit, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; and receiving a clock signal by the digital synthesis circuit, and at each clock cycle: retrieving, by the digital synthesis circuit, a phase point from the first lookup table; retrieving, by the digital synthesis circuit, a phase point from the second lookup table; combining, by the digital processing circuit, the phase point from the first lookup table with the phase point from the second lookup table to generate a combined phase point; and converting, by the DAC circuit, the combined phase point into an analog signal; wherein the analog signal is configured to drive a first and second ultrasonic transducer.

51. The method of clause 50, wherein the first and second digital electrical signal waveforms represent first and second digital ultrasonic electrical signal waveforms.

52. The method of clause 50 or 51, comprising combining a radio frequency (RF) electrical signal waveform with the first and second ultrasonic electrical signal waveforms.

53. The method of any one of clauses 50-52, wherein storing, by the digital processing circuit, phase points of a digital electrical signal waveform in the lookup table defined by the memory circuit, comprises: storing, by the digital processing circuit, phase points of multiple digital electrical signal waveforms in corresponding multiple lookup tables defined by the memory circuit or other memory circuits, wherein each of the digital electrical signal waveforms is represented by a predetermined number of phase points, and wherein each of the predetermined number of phase points defines a different wave shape.

54. The method of any one of clauses 50-53, comprising: receiving, by the digital processing circuit, a feedback signal associated with tissue parameters; and modifying the first or second predetermined wave shape according to the feedback signal.

55. The method of any one of clauses 50-54, wherein the first or second digital electrical signal waveform represents a combination of multiple waveforms having different amplitudes.

56. The method of any one of clauses 50-55, wherein the first or second digital electrical signal waveform represents a combination of multiple waveforms having different frequencies.

57. The method of clause 56, wherein the first or second digital electrical signal waveform represents a combination of multiple waveforms having different amplitudes.

58. The method of any one of clauses 50-57, wherein the first or second predetermined wave shape is a trapezoid, a sine or cosine wave, a square wave, a triangle wave, or any combinations thereof.

59. The method of any one of clauses 50-58, wherein the combined phase point is configured to maintain a predetermined ultrasonic frequency.

60. The method of any one of clauses 50-59, wherein the combined phase point is configured to deliver maximum power output.

61. A method of generating electrical signal waveforms by a generator, the generator comprising a digital processing circuit, a memory circuit in communication with the digital processing circuit, the memory circuit defining first and second lookup tables, a digital synthesis circuit in communication with the digital processing circuit and the memory circuit, and a digital-to-analog converter (DAC) circuit, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; and receiving a clock signal by the digital synthesis circuit, and at each clock cycle: retrieving, by the digital synthesis circuit, a phase point from the first lookup table; retrieving, by the digital synthesis circuit, a phase point from the second lookup table; combining, by the digital processing circuit, the phase point from the first lookup table with the phase point from the second lookup table to generate a combined phase point; and converting, by the DAC circuit, the combined phase point into an analog signal; wherein the analog signal is configured to drive a plurality of ultrasonic operational modes of an ultrasonic device.

62. The method of clause 61, wherein the analog signal is configured to provide a predetermined tissue effect.

63. The method of clauses 61 or 62, wherein the generator comprises a single output port and the method further comprises delivering the analog signal via the single output port.

64. A generator for generating electrical signal waveforms, the generator comprising: a digital processing circuit; a memory circuit in communication with the digital processing circuit, the memory circuit defining a lookup table; a digital synthesis circuit in communication with the digital processing circuit and the memory circuit, the digital synthesis circuit receiving a clock signal; and a digital-to-analog converter (DAC) circuit; the digital processing circuit configured to: store phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; and store phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; at each clock cycle the digital synthesis circuit is configured to: retrieve a phase point from the first lookup table; retrieve a phase point from the second lookup table; the digital processing circuit configured to: combine the phase point from the first lookup table with the phase point from the second lookup table to generate a combined phase point; and the DAC circuit is configured to convert the combined phase point into an analog signal; wherein the analog signal is configured to drive a first and second ultrasonic transducer.

65. The generator of clause 64, comprising a non-volatile memory.

66. The generator of clauses 64 or 65, comprising a field programmable gate array (FPGA).

67. The generator of any one of clauses 64-66, comprising an amplifier coupled to the DAC circuit.

68. The generator of any one of clauses 64-67, wherein the digital synthesis circuit is a direct digital synthesis (DDS) circuit.

69. The generator of any one of clauses 64-68, comprising a filter coupled to an output of the DAC circuit.

70. A method of generating electrical signal waveforms by a generator, the generator comprising a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape; receiving, by the digital synthesis circuit, a clock signal, and at each clock cycle; retrieving, by the digital synthesis circuit, a phase point from the first lookup table; retrieving, by the digital synthesis circuit, a phase point from the second lookup table; combining, by the digital processing circuit, the first and second digital electrical signal waveforms to form a combined digital electrical signal waveform; and modifying, by the digital processing circuit, the combined digital electrical signal waveform to form a modified digital electrical signal waveform, wherein a peak amplitude of the modified digital electrical signal waveform does not exceed a predetermined amplitude value.

71. The method of clause 70, comprising defining, by the digital processing circuit, the first or second digital electrical signal waveform as a radio frequency (RF) drive signal.

72. The method of clause 70 or 71, comprising defining, by the digital processing circuit, the first or second digital electrical signal waveform as an ultrasonic drive signal.

73. The method of any one of clauses 70-72, comprising determining, by the digital processing circuit, the peak amplitude of the combined digital electrical signal waveform while the combined digital electrical signal waveform is being delivered.

74. The method of clause 73, wherein modifying the combined digital electrical signal waveform comprises reducing an amplitude of the combined digital electrical signal waveform upon determining that the peak amplitude of the combined digital electrical signal waveform is approaching while the combined digital electrical signal waveform is being delivered.

75. The method of any one of clauses 70-74, wherein the generator comprises a direct digital synthesis (DDS) circuit and wherein generating the first or second digital electrical signal waveform comprises generating the first or second digital electrical signal waveform via the DDS circuit.

76. The method of any one of clauses 70-75, comprising determining a peak amplitude of the combined waveform and wherein modifying the combined waveform comprises modifying the combined waveform based on the peak amplitude of the combined waveform.

77. The method of any one of clauses 70-76, comprising converting, by the DAC circuit, the digital electrical signal waveform to an analog signal and outputting the analog signal.

78. The method of clause 77, wherein the generator comprises a transformer with a plurality of taps, the method comprises outputting the analog signal via a single port of the generator.

79. A method of generating electrical signal waveforms by a generator, the generator comprising a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape, wherein the second digital electrical signal waveform is a function of the first digital electrical signal waveform;

receiving, by the digital synthesis circuit, a clock signal, and at each clock cycle; retrieving, by the digital synthesis circuit, a phase point from the first lookup table; retrieving, by the digital synthesis circuit, a phase point from the second lookup table; combining, by the digital processing circuit, the first and second digital electrical signal waveforms to form a combined digital electrical signal waveform; and modifying, by the digital processing circuit, the combined digital electrical signal waveform to form a modified digital electrical signal waveform, wherein a peak amplitude of the modified digital electrical signal waveform does not exceed a predetermined amplitude value.

80. The method of clause 79, comprising extracting, by the digital processing circuit, the first or second digital electrical signal waveform from the combined digital electrical signal waveform.

81. The method of clause 80, wherein the first or second digital electrical signal waveform comprises a wave function, the method comprising extracting the wave function from the combined digital electrical signal waveform.

82. The method of any one of clauses 80-81, comprising outputting the combined digital electrical signal waveform via a single port of the generator.

83. The method of any one of clauses 80-82, comprising defining, by the digital processing circuit, the first or second digital electrical signal waveform as an ultrasonic drive signal.

84. The method of any one of clauses 80-83, comprising defining, by the digital processing circuit, the first or second digital electrical signal waveform as a radio frequency (RF) drive signal.

85. A method of generating electrical signal waveforms by a generator, the generator comprising a digital processing circuit, a memory circuit in communication with the digital processing circuit, a digital synthesis circuit in communication with the digital processing circuit and the memory circuit, and a digital-to-analog converter (DAC) circuit, the memory circuit defining first and second lookup tables, the method comprising: storing, by the digital processing circuit, phase points of a first digital electrical signal waveform in a first lookup table defined by the memory circuit, wherein the first digital electrical signal waveform is represented by a first predetermined number of phase points, wherein the first predetermined number of phase points define a first predetermined wave shape; storing, by the digital processing circuit, phase points of a second digital electrical signal waveform in a second lookup table defined by the memory circuit, wherein the second digital electrical signal waveform is represented by a second predetermined number of phase points, wherein the second predetermined number of phase points define a second predetermined wave shape, wherein the second digital electrical signal waveform is a function of the first digital electrical signal waveform; receiving, by the digital synthesis circuit, a clock signal, and at each clock cycle; retrieving, by the digital synthesis circuit, a phase point from the first lookup table; retrieving, by the digital synthesis circuit, a phase point from the second lookup table; modifying, by the digital processing circuit, a frequency of the first digital electrical signal waveform to form a frequency modified first digital electrical signal waveform; and combining, by the digital processing circuit, the frequency modified first digital electrical signal waveform and the second digital electrical signal waveform to form a combined digital electrical signal waveform.

86. The method of clause 85, comprising defining, by the digital processing circuit, the first or second digital electrical signal waveform as a radio frequency (RF) drive signal.

87. The method of clauses 85-86, comprising defining, by the digital processing circuit, the first or second digital electrical signal waveform as an ultrasonic drive signal.

88. The method of any one of clauses 85-87, comprising outputting the combined digital electrical signal waveform via a single port of the generator.

89. The method of any one of clauses 85-88, wherein the generator comprises a direct digital synthesis (DDS) circuit, wherein generating the first digital electrical signal waveform comprises generating the first or second digital electrical signal waveform via the DDS circuit.

90. A method of generating electrical signal waveforms by a generator, the generator comprising a processor and a memory in communication with the processor, the memory defining a first and second table, the method comprising: retrieving, by the processor, information from the first table defined the memory, wherein the information is associated with a first wave shape of a first electrical signal waveform for performing a surgical procedure; retrieving, by the processor, information from the second table defined in the memory, wherein the information is associated with a second wave shape of a second electrical signal waveform for performing a surgical procedure; combining, by the processor, the first and second wave shapes to create a combined wave shape of an electrical signal waveform for performing a surgical procedure; and delivering the combined wave shape electrical signal waveform for performing a surgical procedure to a surgical instrument.

91. The method of clause 90, wherein the first table is defined by the first memory and the second table is defined by a second memory.

92. The method of clause 90 or 91, wherein the first wave shape is associated with a radio frequency (RF) electrical signal waveform and the second wave shape is associated with an ultrasonic electrical signal waveform.

93. The method of any one of clauses 90-92, wherein the first wave shape is associated with a first ultrasonic electrical signal waveform and the second wave shape is associated with a second ultrasonic electrical signal waveform.

94. The method of any one of clauses 90-93, comprising creating the first and second table by a direct digital synthesis circuit coupled to the processor.

95. The method of clause 94, comprising: addressing, by the processor, the first table according to a frequency of the first electrical signal waveform; and addressing, by the processor, the second table according to a frequency of the second electrical signal waveform.

96. The method of clause 94, comprising: storing, by the processor, the information associated with the first wave shape in the memory; and storing, by the processor, the information associated with the second wave shape 97. The method of any one of clauses 90-96, comprising: receiving, by the processor, a feedback signal associated with tissue parameters; and modifying the first and second wave shapes according to the feedback signal.

98. A method of generating electrical signal waveforms by a generator, the generator comprising a processor and a memory in communication with the processor, the memory defining a first and second table, the method comprising: retrieving, by the processor, information from the first table defined the memory, wherein the information is associated with a first wave shape of a first electrical signal waveform for performing a surgical procedure; retrieving, by the processor, information from the second table defined in the memory, wherein the information is associated with a second wave shape of a second electrical signal waveform for performing a surgical procedure; and delivering the first and second electrical signal waveforms for performing a surgical procedure to a surgical instrument.

99. The method of clause 98, comprising switching between the first and second electrical signal waveforms.

100. The method of clause 98 or 99, comprising: synchronizing the first and second electrical signal waveforms; and maximizing power delivered to the surgical instrument.

101. The method of any one of clauses 98-100, wherein the first digital electrical signal waveform represents a RF waveform and the second digital electrical signal waveform represents an ultrasonic signal waveform.

102. The method of any one of clauses 98-101, wherein the first wave shape is associated with a first ultrasonic electrical signal waveform and the second wave shape is associated with a second ultrasonic electrical signal waveform.

103. A method of generating electrical signal waveforms by a generator, the generator comprising a processor and a memory in communication with the processor, the memory defining a first and second table, the method comprising: retrieving, by the processor, information from the first table defined the memory, wherein the information is associated with a first wave shape of a first electrical signal waveform for performing a surgical procedure; retrieving, by the processor, information from the second table defined in the memory, wherein the information is associated with a second wave shape of a second electrical signal waveform for performing a surgical procedure; and combining, by the processor, the first and second wave shapes to create a combined wave shape of an electrical signal waveform for performing a surgical procedure; delivering the combined wave shape electrical signal waveform for performing a surgical procedure to a surgical instrument; and modifying, by the processor, the combined wave shape of the electrical signal waveform to form a modified electrical signal waveform, wherein a peak amplitude of the modified electrical signal waveform does not exceed a predetermined amplitude.

104. The method of clause 103, wherein the first wave shape is associated with a first radio frequency (RF) electrical signal waveform and the second wave shape is associated with a second RF electrical signal waveform.

105. The method of clause 103 or 104, wherein the first wave shape is associated with a first ultrasonic electrical signal waveform and the second wave shape is associated with a second ultrasonic electrical signal waveform.

106. The method of any one of clauses 103-105, wherein the first wave shape is associated with a RF electrical signal waveform and the second wave shape is associated with an ultrasonic electrical signal waveform.

107. The method of any one of clauses 103-106, comprising determining, by the processor, the peak amplitude of the combined electrical signal waveform while delivering the combined electrical signal waveform to the surgical instrument.

108. The method of any one of clauses 103-107, comprising reducing an amplitude of the combined electrical signal waveform when the peak amplitude of the combined electrical signal waveform is approaching.

109. The method of any one of clauses 103-108, comprising determining a peak amplitude of the combined electrical signal waveform and modifying the combined electrical signal waveform comprises based on the determined peak amplitude of the combined electrical signal waveform.

The invention claimed is:

1. A generator comprising:
a processor;
a memory in communication with the processor, the memory defining a first and second table; and
an electrical output port;
wherein the processor is configured to:
retrieve phase points defining a first digital electrical signal wave shape of a first electrical signal waveform from the first table defined in the memory;
retrieve phase points defining a second digital electrical signal wave shape of a second electrical signal waveform from the second table defined in the memory;
combine the phase points of the first digital electrical signal wave shape and the phase points of the second digital electrical signal wave shape to create a combined wave shape of a combined electrical signal waveform for performing a surgical procedure; and
deliver the combined wave shape of the combined electrical signal waveform for performing the surgical procedure to a surgical instrument via the electrical output port.

2. The generator of claim 1, wherein the memory is a first memory, and the generator comprises a second memory; and wherein the first table is defined by the first memory, and the second table is defined by a second memory.

3. The generator of claim 1, wherein the first digital electrical signal wave shape is associated with a radio frequency (RF) electrical signal waveform and the second digital electrical signal wave shape is associated with an ultrasonic electrical signal waveform.

4. The generator of claim 1, wherein the first digital electrical signal wave shape is associated with a first ultrasonic electrical signal waveform and the second digital electrical signal wave shape is associated with a second ultrasonic electrical signal waveform.

5. The generator of claim 1, further comprising a direct digital synthesis circuit coupled to the processor and configured to create the first and second table.

6. The generator of claim 5, wherein the processor is further configured to:
address the first table according to a frequency of the first electrical signal waveform; and
address the second table according to a frequency of the second electrical signal waveform.

7. The generator of claim 5, wherein the processor is further configured to:
store information associated with the first digital electrical signal wave shape in the memory; and
store information associated with the second digital electrical signal wave shape.

8. The generator of claim 1, wherein the processor is further configured to:
receive a feedback signal associated with tissue parameters; and
modify the first and second digital electrical wave shapes according to the feedback signal.

9. A generator comprising:
a processor;
a memory in communication with the processor, the memory defining a first and second table; and
an electrical output port;
wherein the processor is configured to:
retrieve information from the first table defined in the memory, wherein the information from the first table is associated with a first wave shape of a first electrical signal waveform for performing a surgical procedure;

retrieve information from the second table defined in the memory, wherein the information from the second table is associated with a second wave shape of a second electrical signal waveform for performing a surgical procedure;

deliver the first and second electrical signal waveforms for performing a surgical procedure to a surgical instrument via the electrical output port; wherein delivering the first and second electrical signal waveforms comprises at least one of: switching between the first and second electrical signal waveforms or synchronizing the first and second electrical signal waveforms;

receive a feedback signal associated with tissue parameters; and based on the feedback signal, and while delivering the first and second electrical signal waveforms, determine whether to:

switch from a first phase point of the first electrical signal waveform to a second phase point of the second electrical signal waveform and convert the second phase point to a first analog signal; or synchronize delivery of the first and the second phase points and convert the synchronized first and the second phase points to a second analog signal.

10. The generator of claim 9, wherein the processor is further configured to maximize power delivered to the surgical instrument.

11. The generator of claim 9, wherein the first electrical signal waveform represents a radio frequency (RF) waveform and the second electrical signal waveform represents an ultrasonic signal waveform.

12. The generator of claim 9, wherein the first wave shape is associated with a first ultrasonic electrical signal waveform and the second wave shape is associated with a second ultrasonic electrical signal waveform.

13. A generator comprising:
a processor;
a memory in communication with the processor, the memory defining a first and second table; and
an electrical output port;
wherein the processor is configured to:
retrieve information from the first table defined in the memory, wherein the information from the first table is associated with a first wave shape of a first electrical signal waveform for performing a surgical procedure;
retrieve information from the second table defined in the memory, wherein the information from the second table is associated with a second wave shape of a second electrical signal waveform for performing a surgical procedure; and
combine the first and second wave shapes to create a combined wave shape of a combined electrical signal waveform for performing a surgical procedure;
deliver the combined wave shape of the combined electrical signal waveform for performing the surgical procedure to a surgical instrument via the electrical output port; and
modify the combined wave shape of the combined electrical signal waveform to form a modified electrical signal waveform, the modified electrical signal waveform comprising a peak amplitude that does not exceed a predetermined amplitude and is less than a peak amplitude of the combined electrical signal waveform.

14. The generator of claim 13, wherein the first wave shape is associated with a first radio frequency (RF) electrical signal waveform and the second wave shape is associated with a second RF electrical signal waveform.

15. The generator of claim 13, wherein the first wave shape is associated with a first ultrasonic electrical signal waveform and the second wave shape is associated with a second ultrasonic electrical signal waveform.

16. The generator of claim 13, wherein the first wave shape is associated with a radio frequency (RF) electrical signal waveform and the second wave shape is associated with an ultrasonic electrical signal waveform.

17. The generator of claim 13, wherein the processor is further configured to determine the peak amplitude of the combined electrical signal waveform while delivering the combined electrical signal waveform to the surgical instrument.

18. The generator of claim 13, wherein the processor is further configured to reduce an amplitude of the combined electrical signal waveform prior to an occurrence of the peak amplitude of the combined electrical signal waveform.

19. The generator of claim 13, wherein the processor is further configured to:
determine the peak amplitude of the combined electrical signal waveform; and
modify the combined electrical signal waveform based on the determined peak amplitude of the combined electrical signal waveform.

* * * * *